US009745589B2

(12) United States Patent
Glimcher et al.

(10) Patent No.: US 9,745,589 B2
(45) Date of Patent: Aug. 29, 2017

(54) METHODS FOR MODULATING SKELETAL REMODELING AND PATTERNING BY MODULATING SHN2 ACTIVITY, SHN3 ACTIVITY, OR SHN2 AND SHN3 ACTIVITY IN COMBINATION

(75) Inventors: Laurie H. Glimcher, New York, NY (US); Dallas C. Jones, Brookline, MA (US); Marc Wein, Brookline, MA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/521,709

(22) PCT Filed: Jan. 13, 2011

(86) PCT No.: PCT/US2011/021056
§ 371 (c)(1),
(2), (4) Date: Oct. 24, 2012

(87) PCT Pub. No.: WO2011/088163
PCT Pub. Date: Jul. 21, 2011

(65) Prior Publication Data
US 2013/0202533 A1    Aug. 8, 2013

Related U.S. Application Data

(60) Provisional application No. 61/295,092, filed on Jan. 14, 2010.

(51) Int. Cl.
| | | |
|---|---|---|
| C12N 15/11 | (2006.01) | |
| C12N 15/113 | (2010.01) | |
| A61K 31/713 | (2006.01) | |
| A61K 35/28 | (2015.01) | |
| C07K 16/18 | (2006.01) | |
| C12N 15/63 | (2006.01) | |
| G01N 33/68 | (2006.01) | |
| A61K 31/7088 | (2006.01) | |
| A61K 38/17 | (2006.01) | |
| G01N 33/50 | (2006.01) | |

(52) U.S. Cl.
CPC .......... *C12N 15/63* (2013.01); *A61K 31/7088* (2013.01); *A61K 31/713* (2013.01); *A61K 38/1709* (2013.01); *G01N 33/5044* (2013.01); *G01N 33/6893* (2013.01); *G01N 2500/00* (2013.01); *G01N 2800/105* (2013.01); *G01N 2800/108* (2013.01)

(58) Field of Classification Search
CPC .. C12N 15/1136; C12N 2310/11; A61K 35/28
See application file for complete search history.

(56) References Cited

U.S. PATENT DOCUMENTS

| | | | |
|---|---|---|---|
| 6,761,887 B1 | 7/2004 | Kavalkovich et al. | |
| 7,592,177 B2 | 9/2009 | Chen et al. | |
| 7,615,380 B2 | 11/2009 | Glimcher et al. | |
| 8,293,477 B2 | 10/2012 | Glimcher et al. | |
| 8,357,637 B2 | 1/2013 | Glimcher et al. | |
| 2002/0022021 A1 | 2/2002 | Emerson | |
| 2003/0087259 A1 | 5/2003 | Clancy et al. | |
| 2003/0092603 A1 | 5/2003 | Mundy et al. | |
| 2004/0191220 A1 | 9/2004 | Einat et al. | |
| 2005/0026285 A1 | 2/2005 | Glimcher et al. | |
| 2007/0224653 A1* | 9/2007 | Glimcher et al. ........... 435/7.31 |
| 2008/0318987 A1 | 12/2008 | Glimcher | |
| 2009/0053189 A1 | 2/2009 | Glimcher et al. | |
| 2009/0300790 A1* | 12/2009 | Aharoni ............. C12N 15/8273 800/278 |
| 2009/0318338 A1 | 12/2009 | Glimcher et al. | |
| 2010/0055678 A1 | 3/2010 | Jaatinen et al. | |
| 2010/0183514 A1 | 7/2010 | Glimcher et al. | |
| 2010/0204053 A1 | 8/2010 | Glimcher | |
| 2010/0330085 A1 | 12/2010 | Coussens et al. | |
| 2011/0008779 A1 | 1/2011 | Liew | |
| 2011/0183866 A1 | 7/2011 | Clarke et al. | |

FOREIGN PATENT DOCUMENTS

| | | |
|---|---|---|
| WO | 00/77168 A2 | 12/2000 |
| WO | 01/16604 A1 | 3/2001 |
| WO | 02/086443 A2 | 10/2002 |
| WO | 02/090595 A1 | 11/2002 |
| WO | 03/066048 A2 | 8/2003 |
| WO | 2004/020458 A2 | 3/2004 |
| WO | 2004/060304 A2 | 7/2004 |
| WO | 2005/001482 A1 | 1/2005 |
| WO | 20051042726 A2 | 5/2005 |
| WO | 20051113588 A2 | 12/2005 |
| WO | 20051124343 A2 | 12/2005 |
| WO | 2006/113559 A2 | 10/2006 |
| WO | 20061132248 A1 | 12/2006 |
| WO | 20081103314 A2 | 8/2008 |
| WO | 20081133936 A2 | 11/2008 |
| WO | 20081153814 A2 | 12/2008 |
| WO | 2011/088163 A1 | 7/2011 |
| WO | 20131119893 A1 | 8/2013 |

OTHER PUBLICATIONS

Blitz et al Developmental Dynamics Finding partners: How BMPs select their targets vol. 238, Issue 6, pp. 1321-1331, Jun. 2009.*
Buckwalter et al Bone Joint Surg Am, 1995—pp. 1257-1275 Bone Biology.*
Wu et al Gene Expr. 2002;10(4):137-52. ZAS: C2H2 zinc finger proteins involved in growth and development. Abstract.*

(Continued)

*Primary Examiner* — Maria Leavitt
(74) *Attorney, Agent, or Firm* — Schwegman Lundberg & Woessner, P.A.

(57) ABSTRACT

This invention is based, at least in part, on the discovery that Shn2 and Shn3 play an important role in skeletal remodeling and skeletal patterning. Accordingly, the present invention provides methods for identifying medulators of Shn2 activity and methods for modulating bone formation and mineralization and Shn2-associated disorders using agents that modulate Shn2 expression and/or activity, in addition to methods for modulating Shn2 and Shn3.

8 Claims, 20 Drawing Sheets

(56) References Cited

OTHER PUBLICATIONS

JOnes et al Regulation of Adult Bone Mass by theZinc Finger Adapter Protein Schnurri-3 Science vol. 312 May 26, 2006 pp. 1223-1227.*
Jones, Dallas C. et al., "Regulation of Adult Bone Mass by the Zinc Finger Adapter Protein Schnurri-3," Science, vol. 312:1223-1227 (2006).
Jones, Dallas C. et al., "Uncoupling of growth plate maturation and bone formation in mice lacking both Schnurri-2 and Schnurri-3," PNAS, vol. 107(18):8254-8258 (2010).
Saita, Yoshitomo et al., "Lack of Schnurri-2 Expression Associates with Reduced Bone Remodeling and Osteopenia," The Journal of Biological Chemistry, vol. 282(17):12907-12915 (2007).
Takagi, Tsuyoshi et al., "Murine Schnurri-2 is required for positive selection of thymocytes," Nature Immunology, vol. 2(11):1048-1053 (2001).
Tamma, Roberto et al., "Oxytocin is an anabolic bone hormone," PNAS, vol. 106(17):7149-7154 (2009).
International Search Report and Written Opinion for Application No. PCT/US2011/021056, 17 pages, dated Jul. 4, 2011.
International Preliminary Report on Patentability and Written Opinion for Application No. PCT/US2011/021056, 10 pages, dated Jul. 17, 2012.
Invitation to Pay Additional Fees for Application No. PCT/US2011/021056, 9 pages, dated May 18, 2011.
International Search Report for Application No. PCT/US2008/006783, dated Dec. 9, 2008.
U.S. Appl. No. 10/578,402, filed Nov. 21, 2006, Laurie H. Glimcher.
U.S. Appl. No. 10/701,401, filed Nov. 3, 2003, Laurie H. Glimcher.
U.S. Appl. No. 11/918,503, filed Feb. 23, 2009, Laurie H. Glimcher.
U.S. Appl. No. 12/032,609, filed Feb. 15, 2008, Laurie H. Glimcher.
U.S. Appl. No. 12/156,008, filed May 29, 2008, Laurie H. Glimcher.
U.S. Appl. No. 11/416,799, filed May 3, 2006, Laurie H. Glimcher.
U.S. Appl. No. 12/614,832, filed Nov. 9, 2009, Laurie H. Glimcher.
U.S. Appl. No. 12/595,911, filed Apr. 15, 2010, Laurie H. Glimcher.
U.S. Appl. No. 12/598,495, filed Mar. 29, 2010, Laurie H. Glimcher.
U.S. Appl. No. 10/578,402, Feb. 2, 2012, Kevin Kai Hill.
U.S. Appl. No. 10/578,402, Jun. 24, 2011, Kevin Kai Hill.
U.S. Appl. No. 10/578,402, Apr. 15, 2010, Kevin Kai Hill.
U.S. Appl. No. 10/578,402, Oct. 7, 2009, Kevin Kai Hill.
U.S. Appl. No. 10/578,402, Jan. 30, 2009, Kevin Kai Hill.
U.S. Appl. No. 10/701,401, Apr. 10, 2009, Kevin Kai Hill.
U.S. Appl. No. 10/701,401, Dec. 16, 2008, Kevin Kai Hill.
U.S. Appl. No. 10/701,401, Jul. 24, 2008, Kevin Kai Hill.
U.S. Appl. No. 10/701,401, Oct. 16, 2007, Kevin Kai Hill.
U.S. Appl. No. 10/701,401, Jan. 23, 2007, Kevin Kai Hill.
U.S. Appl. No. 10/701,401, May 11, 2006, Kevin Kai Hill.
U.S. Appl. No. 11/918,503, Jun. 22, 2012, David S. Romeo.
U.S. Appl. No. 11/918,503, Nov. 17, 2011, David S. Romeo.
U.S. Appl. No. 11/918,503, Jun. 7, 2011, David S. Romeo.
U.S. Appl. No. 12/032,609, Nov. 4, 2014, Sara Elizabeth Townsley.
U.S. Appl. No. 12/032,609, Apr. 2, 2014, Sara Elizabeth Townsley.
U.S. Appl. No. 12/032,609, May 17, 2011, Sara Elizabeth Townsley.
U.S. Appl. No. 12/032,609, Nov. 15, 2010, Sara E. Clark.
U.S. Appl. No. 12/032,609, Jun. 30, 2010, Sara E. Clark.
U.S. Appl. No. 12/156,008, Jul. 3, 2012, Teresa D. Wessendorf.
U.S. Appl. No. 12/156,008, Dec. 6, 2011, Teresa D. Wessendorf.
U.S. Appl. No. 12/156,008, Mar. 30, 2011, Teresa D. Wessendorf.
U.S. Appl. No. 12/595,911, Sep. 18, 2012, David S. Romeo.
U.S. Appl. No. 12/595,911, Apr. 24, 2012, David S. Romeo.
U.S. Appl. No. 12/598,495, Sep. 20, 2012, Christian C. Boesen.
Affolter, et al., "Nuclear interpretation of Dpp signaling in *Drosophila*," EMBO J., vol. 20(13):3298-305 (2001).
Allen, Carl E. et al., "KRC controls cell growth by regulating the transcription of c-myc," Presented at the American Society of Biochemistry and Molecular Biology Annual Meeting, Washington, D.C., p. A1391, Abstract No. 473 (1998).

Allen, et al., "Developmental anomalies and neoplasia in animals and cells deficient in the large zinc finger protein KRC," Genes Chromosomes Cancer, vol. 35(4):287-98 (2002).
Allen, et al., "Downregulation of KRC induces proliferation, anchorage independence, and mitotic cell death in HeLa cells," Exp Cell Res., vol. 260(2):346-56 (2000).
Allen, et al., "The kappa B transcriptional enhancer motif and signal sequences of V(D)J recombination are targets for the zinc finger protein HIVEP3/KRC: a site selection amplification binding study," BMC Immunol., vol. 22;3(1):10 (2002).
Alliston, Tamara et al., "TGF-b-induced repression of CBFA1 by Smad3 decreases cbfa1 and osteocalcin expression and inhibits osteoblast differentiation," The EMBO Journal, vol. 20(9):2254-2272 (2001).
Anders, Hans-Joachim et al., "Murine Models of Renal Disease: Possibilities and Problems in Studies Using Mutant Mice," Exp. Nephrol., vol. 8:181-193 (2000).
Angel P. et al., "Phorbol ester-inducible genes contain a common cis element recognized by a TPA-modulated trans-acting factor," Cell, vol. 49(6):729-39 (1987).
Arch, et al., "Tumor necrosis factor receptor-associated factors (TRAFs)—a family of adapter proteins that regulates life and death," Genes Dev., vol. 12(18):2821-30 (1998).
Arias, et al., "Activation of cAMP and mitogen responsive genes relies on a common nuclear factor," Nature, vol. 370 (6486):226-9 (1994).
Arora, et al., "The *Drosophila schnurri* gene acts in the Dpp/TGF beta signaling pathway and encodes a transcription factor homologous to the human MBP family," Cell, vol. 81(5):781-90 (1995).
Bachmeyer, et al., "Regulation by phosphorylation of the zinc finger protein KRC that binds the kappaB motif and V (D)J recombination signal sequences," Nucleic Acids Res., vol. 27(2):643-8 (1999).
Behre, et al., "C-Jun is a JNK-independent coactivator of the PU.1 transcription factor," J. Biol. Chem., vol. 274 (8):4939-46 (1999).
Behrens, et al., "Jun N-terminal kinase 2 modulates thymocyte apoptosis and T cell activation through c-Jun and nuclear factor of activated T cell (NF-AT)," Proc. Natl. Acad. Sci. USA, vol. 98(4):1769-74 (2001).
Bellows, C.G. et al., "Mineralized Bone Nodules Formed In Vitro from Enzymatically Released Rat Calvaria Cell Populations," Calcif. Tissue Int., vol. 38:143-154 (1986).
Bianchi, et al., "Integrin LFA-1 interacts with the transcriptional co-activator JAB1 to modulate AP-1 activity," Nature, vol. 404(6778):617-21 (2000).
Binetruy, et al., "Ha-Ras augments c-Jun activity and stimulates phosphorylation of its activation domain," Nature, vol. 351(6322):122-7 (1991).
Bio-Rad, "Nucleic Acids, Nucleosides, and Nucleotides Database," Bio-Rad Laboratories, obtained online at: http://www.biorad.fi/pages/SAD/indices/index4393.pdf, 13 pages, 2006 catalog.
Bishop, Jo, "Chromosomal insertion of foreign DNA," Reprod. Nutr. Dev., vol. 36:607-618 (1996).
Blokzijl, Andries et al., "Physical and Functional Interaction between GATA-3 and Smad3 Allows TGF-b Regulation of GATA Target Genes," Current Biology, vol. 12:35-45 (2002).
Borden, et al., "The solution structure of the RING finger domain from the acute promyelocytic leukaemia proto-oncoprotein PML," EMBO J., vol. 14(7):1532-41 (1995).
Bork, Peer, "Powers and Pitfalls in Sequence Analysis: The 70% Hurdle," Genome Research, vol. 10:398-400 (2000).
Cameron, Ewan R., "Recent Advances in Transgenic Technology," Molecular Biotechnology, vol. 7:253-265 (1997).
Cao, et al., "TRAF6 is a signal transducer for interleukin-1," Nature, vol. 383(6599):443-6 (1996).
Castellanos, et al., "Expression of the leukocyte early activation antigen CD69 is regulated by the transcription factor AP-1," J. Immunol., vol. 159(11):5463-73 (1997).
Claret, et al., "A new group of conserved coactivators that increase the specificity of AP-1 transcription factors," Nature, vol. 383(6599):453-7 (1996).
Cleland, Jeffrey L. et al., "Emerging protein delivery methods," Current Opinion in Biotechnology, vol. 12:212-219 (2001).

(56) References Cited

OTHER PUBLICATIONS

Cohn, et al., "Characterization of Sp1, AP-1, CBF and KRC binding sites and minisatellite DNA as functional elements of the metastasis-associated mts1/S100A4 gene intronic enhancer," Nucleic Acids Res., vol. 29(16):3335-46 (2001).
Coquelle, Frederic M. et al., "Common and Divergent Roles for Members of the Mouse DCX Superfamily," Cell Cycle, vol. 5(9):976-983 (2006).
Cubadda, Yolande et al., "u-shaped encodes a zinc finger protein that regulates the proneural genes achaete and scute during the formation of bristles of Drosophila," Genes & Development, vol. 11:3083-3095 (1997).
Daga, Andrea et al., "Patterning of cells in the Drosophila eye by Lozenge, which shares homologous domains with AML1," Genes & Development, vol. 10:1194-1205 (1996).
Dai, et al., "The zinc finger protein schnurri acts as a Smad partner in mediating the transcriptional response to decapentaplegic," Dev. Biol., vol. 227(2):373-87 (2000).
Deng, et al., "c-Fos transcriptional activity stimulated by H-Ras-activated protein kinase distinct from JNK and ERK," Nature, vol. 371(6493):171-5 (1994).
Denning, C. et al., "Deletion of the a(1,3)galactosyl transferase (GGTA1) gene and the prion protein (PrP) gene in sheep," Nature Biotechnology, vol. 19:559-562 (2001).
Deonarain, Mahendra P., "Ligand-targeted receptor-mediated vectors for gene delivery," Exp. Opin. Ther. Patents, vol. 8(1):53-69 (1998).
Derynck, Rik et al., "Smads: Transcriptional Activators of TGF-b Responses," Cell, vol. 95:737-740 (1998).
Doerks, Tobias et al., "Protein annotation: detective work for function prediction," TIG, vol. 14(6):248-250 (1998).
Dong, et al., "JNK is required for effector T-cell function but not for T-cell activation," Nature, vol. 405(6782):91-4 (2000).
Ducy, Patricia et al., "A Cbfa1-dependent genetic pathway controls bone formation beyond embryonic development," Genes & Development, vol. 13:1025-1036 (1999).
Dumitru, et al., "TNF-alpha induction by LPS is regulated post-transcriptionally via a Tpl2/ERK-dependent pathway," Cell, vol. 103(7):1071-83 (2000).
Durand, et al., "A 275 basepair fragment at the 5' end of the interleukin 2 gene enhances expression from a heterologous promoter in response to signals from the T cell antigen receptor," J. Exp. Med., vol. 165(2):395-407 (1987).
Eck, Stephen L. et al., "Gene-Based Therapy," Goodman & Gilman's The Pharmacological Basis of Therapeutics, Ninth Edition, McGraw-Hill, Chpt. 5, pp. 77-101 (1996).
Gerlai, Robert, "Gene-targeting studies of mammalian behavior: is the mutation or the background genotype," Trends Neurosci., vol. 19:177-181 (1996).
Ghosh, et al., "NF-KappaB and Rel Proteins: Evolutionarily conserved mediators of immune responses," Annu. Rev. Immunol., vol. 16:226-260 (1998).
Giner-Sorolla, Alfredo et al., "Synthesis and Properties of 5-Mercaptomethyluracil and Related Derivatives," J. Med. Chem., vol. 9(1):97-101 (1966).
Glimcher, Laurie H. et al., "Control of Postnatal Bone Mass by the Zinc Finger Adapter Protein Schnurri-3," Ann. N. Y. Acad. Sci., vol. 1116:174-181 (2007).
Gorecki, Dariusz C., "Prospects and problems of gene therapy: an update," Expert Opinion Emerging Drugs, vol. 6 (2):187-198 (2001).
Grieder, et al., "Schnurri is required for Drosophila Dpp signaling and encodes a zinc finger protein similar to the mammalian transcription factor PRDII-BF1," Cell, vol. 81(5):791-800 (1995).
Guo, Haiwei H. et al., "Protein tolerance to random amino acid change," PNAS, vol. 101(25):9205-9210 (2004).
Haenlin, Marc et al., "Transcriptional activity of Pannier is regulated negatively by heterodimerization of the GATA DNA-binding domain with a cofactor encoded by the u-shaped gene of Drosophila," Genes & Development, vol. 11:3096-3108 (1997).

Hicar, et al., "Embryonic expression and regulation of the large zinc finger protein KRC," Genesis, vol. 33(1):8-20 (2002).
Hicar, et al., "Structure of the human zinc finger protein HIVEP3: molecular cloning, expression, exon-intron structure, and comparison with paralogous genes HIVEP1 and HIVEP2," Genomics, vol. 71(1):89-100 (2001).
Rimes, et al., "High mobility group protein I(Y) is required for function and for c-Rel binding to CD28 response elements within the GM-CSF and IL-2 promoters," Immunity, vol. 5(5):479-89 (1996).
Hjelmsoe, et al., "The kappaB and V(D)J recombination signal sequence binding protein KRC regulates transcription of the mouse metastasis-associated gene S100A41mts1," J. Biol. Chem., vol. 275(2):913-20 (2000).
Hofstaetter, J.G. et al., "High Bone Mass and Increased Degree of Mineralization in Schnurri-3 Null Mice," Bone, vol. 39(5):S18 (2006).
Houdebine, Louis-Marie, "Production of pharmaceutical proteins from transgenic animals," Journal of Biotechnology, vol. 34:269-287 (1994).
Hult, Karl et al., "Engineered enzymes for improved organic synthesis," Current Opinion in Biotechnology, vol. 14:395-400 (2003).
Humpherys, David et al., "Epigenetic Instability in ES Cells and Cloned Mice," Science, vol. 293:95-97 (2001).
Ip, et al., "Signal transduction by the c-Jun N-terminal kinase (JNK)—from inflammation to development," Curr. Opin. Cell Biol., vol. 10(2):205-19 (1998).
Isakov, et al., "Protein kinase C(theta) in T cell activation," Annu. Rev. Immunol., vol. 20:761-94 (2002).
Jain, et al., "Nuclear factor of activated T cells contains Fos and Jun," Nature, vol. 356(6372):801-4 (1992).
Jain, et al., "Transcriptional regulation of the IL-2 gene," Curr. Opin. Immunol., vol. 7(3):333-42 (1995).
Jochum, et al., "AP-1 in mouse development and tumorigenesis," Oncogene, vol. 20(19):2401-12 (2001).
Jones, Dallas C. et al., "Schnurri-3 is an essential regulator of osteoblast function and adult bone mass," Ann. Rheum. Dis, vol. 66(Suppl. III):iii49-iii51 (2007).
Jones, Dallas C. et al., "Schnurri-3: A Key Regulator of Postnatal Skeletal Remodeling," Adv. Exp. Med. Biol., Osteoimmunology, Interactions of the Immune and Skeletal Systems, Yongwon Choi, Ed., Springer, vol. 602, Chapter 1, pp. 1-13 (2007).
Kamei, et al., "A CBP integrator complex mediates transcriptional activation and AP-1 inhibition by nuclear receptors," Cell, vol. 85(3):403-14 (1996).
Kaneki, Hiroyuki et al., "Tumor Necrosis Factor Promotes Runx2 Degradation through Up-regulation of Smurf1 and Smurf2 in Osteoblasts," J. Biol. Chem., vol. 281(7):4326-4333 (2006).
Kappel, Catherine A. et al., "Regulating gene expression in transgenic animals," Current Opinion in Biotechnology, vol. 3:548-553 (1992).
Karin M., "The NF-kappa B activation pathway: its regulation and role in inflammation and cell survival," Cancer J. Sci. Am., vol. 4 Suppl 1:892-9 (1998).
Karin, et al., "AP-1 function and regulation," Curr. Opin. Cell Biol., vol. 9(2):240-6 (1997).
Krishnan, Venkatesh et al., "Parathyroid Hormone Bone Anabolic Action Requires Cbfa1/Runx2-Dependent Signaling," Molecular Endocrinology, vol. 17(3):423-435 (2003).
Kuroiwa, Yoshimi et al., "Sequential targeting of the genes encoding immunoglobulin-m and prion protein in cattle," Nature Genetics, vol. 36(7):775-780 (2004).
Lee, et al., "Activating protein-1, nuclear factor-kappaB, and serum response factor as novel target molecules of the cancer-amplified transcription coactivator ASC-2," Mol. Endocrinol., vol. 14(6):915-25 (2000).
Lee, Hyun Jun et al., "Characterization of cis-Regulatory Elements and Nuclear Factors Conferring Th2-Specific Expression of the IL-5 Gene: A Role for a GATA-Binding Protein," The Journal of Immunology, vol. 160:2343-2352 (1998).

(56) References Cited

OTHER PUBLICATIONS

Lee et al "Steroid receptor coactivator-1 coactivates activating protein-1-mediated transactivations through interaction with the c-Jun and c-Fos subunits," J. Biol. Chem., vol. 273(27):16651-4 (1998).
Lee, et al., "TRAF2 is essential for JNK but not NF-kappaB activation and regulates lymphocyte proliferation and survival," Immunity, vol. 7(5):703-13 (1997).
Leppa, et al., "Diverse functions of JNK signaling and c-Jun in stress response and apoptosis," Oncogene, vol. 18 (45):6158-62 (1999).
Liberati, et al., "Smads bind directly to the Jun family of AP-1 transcription factors," Proc. Natl. Acad. Sci. USA, vol. 96(9):4844-9 (1999).
Liew, Chu Kong et al., "Solution Structures of Two CCHC Zinc Fingers from the FOG Family Protein U-Shaped that Mediate Protein-Protein Interactions," Structure, vol. 8:1157-1166 (2000).
Lindsten, et al., "Regulation of lymphokine messenger RNA stability by a surface-mediated T cell activation pathway," Science, vol. 244(4902):339-43 (1989).
Lowry, Jason A. et al., "Molecular Evolution of the GATA Family of Transcription Factors: Conservation Within the DNA-Binding Domain," Journal of Molecular Evolution, vol. 50:103-115 (2000).
Lund, Anders H. et al., "RUNX: A triology of cancer genes," Cancer Cell, vol. 1:213-215 (2002).
Lutterbach, B. et al., "Role of the transcription factor AML-1 in acute leukemia and hematopoietic differentiation," Gene, vol. 245:223-235 (2000).
Macian, et al., "Transcriptional mechanisms underlying lymphocyte tolerance," Cell, vol. 109(6):719-31 (2002).
Mak, et al., "KRC transcripts: identification of an unusual alternative splicing event," Immunogenetics, vol. 48(1):32-9 (1998).
Mak, et al., "The V(D)J recombination signal sequence and kappa B binding protein Rc binds DNA as dimers and forms multimeric structures with its DNA ligands," Nucleic Acids Res., vol. 22(3):383-90 (1994).
Massague, Joan et al., "Transcriptional control by the TGF-b/Smad signaling system," The EMBO Journal, vol. 19 (8):1745-1754 (2000).
Matthews, Jacqueline et al., "A class of zinc fingers involved in protein-protein interactions. Biophysical characterization of CCHC fingers from Fog and U-shaped," Eur. J. Biochem., vol. 267:1030-1038 (2000).
Matunis, et al., "Punt and schnurri regulate a somatically derived signal that restricts proliferation of committed progenitors in the germline," Development, vol. 124(21):4383-91 (1997).
Mobasheri, A. et al., "Expression of Cation Exchange NHE and Anion Exchanger AE Isoforms in Primary Human Bone-Derived Osteoblasts," Cell Biology International, vol. 22(718):551-562 (1998).
Mondino, et al., "Defective transcription of the IL-2 gene is associated with impaired expression of c-Fos, FosB, and JunB in anergic T helper 1 cells," J. Immunol., vol. 157(5):2048-57 (1996).
Moreadith, Randall Wade et al., "Gene targeting in embryonic stem cells: the new physiology and metabolism," J. Mol. Med., vol. 75:208-216 (1997).
Moreau, et al., "Bone-specific expression of the alpha chain of the nascent polypeptide-associated complex, a coactivator potentiating c-Jun-mediated transcription," Mol. Cell Biol., vol. 18(3):1312-21 (1998).
Mullins, John J. et al., "Transgenesis in Nonmurine Species," Hypertension, vol. 22(4):630-633 (1993).
Mullins, Linda J. et al., "Molecular Medicine in Genetically Engineered Animals," J. Clin. Invest., vol. 97 (7):1557-1560 (1996).
Murphy, et al., "Molecular interpretation of ERK signal duration by immediate early gene products," Nat. Cell Biol., vol. 4(8):556-64 (2002).
Nakano, et al., "TRAF5, an activator of NF-kappaB and putative signal transducer for the lymphotoxin-beta receptor," J. Biol. Chem., vol. 271(25):14661-4 (1996).

Ngo, J. Thomas et al., "Computational Complexity Protein Structure Prediction, and the Levinthal Paradox," The Protein Folding Problem and Tertiary Structure Prediction, Chpt. 14, pp. 491-495 (1994).
Oukka, et al., "A mammalian homolog of Drosophila schnurri, KRC, regulates TNF receptor-driven responses and interacts with TRAF2," Mol. Cell., vol. 9(1)121-31 (2002).
Oukka, Mohamed et al., "Schnurri-3 (KRC) Interacts with c-Jun to Regulate the IL-2 Gene in T Cells," J. Exp. Med., vol. 199(1):15-24 (2004).
Jones et al., "Regulation of adult bone mass by the zinc finger adapter protein Schnurri-3," Science, vol. 312, 1223-1227 (2006).
Kawamata, A. et al., "JunD suppresses bone formation and contributes to low bone mass induced by estrogen depletion," J Cell Biochem., vol. 103(4):1037-1045 (2008).
Mak et al., "The V(D)J recombination signal sequence and kappa B binding protein Rc binds DNA as dimers and forms multimeric structures with its DNA ligands," Nucleic Acids Research, vol. 22(3): 383-390 (1994).
Makino et at., "Cloning and characterization of a c-myc intron binding protein (MIBP1)," Nucleic Acids Research, vol. 22(25): 5679-5685 (1994).
Oukka et at., "A mammalian homolog of Drosophila schnurri, KRC, regulates TNF receptor-driven responses and Interacts with TRAF2,"Molecular Cell, vol. 9:121-131 (2002).
Reimold, A et al., "Chondrodysplasia and neurological abnormalities in ATF-2-deficient mice," Nature, vol. 379: 262-265 (1996).
Sabatakos, G. et al., "Overexpression of alphaFosB transcription factor(s) increases bone formation and inhibits adipogenesis," Nature Medicine, vol. 6, 985-990 (2000).
Salta et al., "Lack of Schnurri-2 expression associates with reduced bone remodeling and osteopenia," J. Biol. Chem., vol. 282(17): 12907-12915 (2007).
Shim, JH et al., "Schnurri-3 regulates ERK downstream of WNT signaling in osteoblasts," J Clin Invest., vol. 123 (9):4010-4022 (2013).
van't Veer et al., "Structure and expression of major histocompatibility complex-binding protein 2, a 275-kDa zinc finger protein that binds to an enhancer of major histocompatibility complex class I genes," Proc. Natl. Acad. Sci., vol. 89: 8971-8975 (1992).
Wagner, E., "Functions of AP1 (Fos/Jun) in bone development," Ann Rheum Dis., vol. 61(Suppl 2): ii40-ii42. (2002).
Wu et at., "Molecular cloning of a zinc finger protein which binds to the heptamer of the signal sequence for V(D)J recombination," Nucleic Acids Research, vol. 21(22): 5067-5073 (1993).
Wu et at., "The mouse DNA binding protein Rc for the kappa B motif of transcription and for the V(D)J recombination signal sequences contains composite DNA-protein interaction domains and belongs to a new family of large transcriptional proteins," Genomics, vol. 35: 415-424 (1996).
Zajac-Kaye et at., "Induction of Myc-intron-binding polypeptides MIBP1 and RFX1 during retinoic acid-mediated lifferentiation of haemopoietic cells," Biochem. J., vol. 345: 535-541 (2000).
Allen, C. et al., "ZAS Zinc Finger Proteins: The Other kB-binding Protein Family," Landes Bioscience, Chapter 29: 213-220 (2005).
Bruning, JC et al., "Ribosomal subunit kinase-2 is required for growth factor-stimulated transcription of the c-Fos gene," Proc Natl Acad Sci USA., vol. 97(6):2462-2467 (2000).
Iwamura, C. et al., "Schnurri-2 regulates Th 2-dependent airway inflammation and airway hyperresponsiveness," International Immunology, vol. 19(6): 755-762 (2007).
Jin, W. et al., "Schnurri-2 Controls BMP-Dependent Adipogenesis via Interaction with Smad Proteins," Developmental Cell, vol. 10: 461-471 (2006).
Kimura, M. et al., "Regulation of T helper type 2 cell differentiation by murine Schnurri-2," JEM, vol. 201(3): 397-408 (2005).
Kimura, M. et al., "Schnurri-2 Controls Memory Th1 and Th2 Cell Numbers in Vivo 1," The Journal of Immunology, 4926-4936 (2007).
Liu, S. et al., "The large zinc finger protein ZAS3 is a critical modulator of osteoclastogenesis," PLoS One, vol. 6(3): e17161:12 pages (2011).

(56) References Cited

OTHER PUBLICATIONS

Takagi a, T. et al., "Schnurri-2 mutant mice are hypersensitive to stress and hyperactive," Brain Research, vol. 1108: 88-97 (2006).
Takao, K. et al., "P2-j37 Deletion of Schnurri-2 causes multiple behavioral abnormalities related to psychiatric disorders in mice," Neuroscience Research, Abstract, vol. 585: S1-S244 (2007).
Vickers, K.C. et al., "Lyso-phosphatidylcholine induces osteogenic gene expression and phenotype in vascular smooth muscle cells," Atherosclerosis, vol. 211(1):122-129 (2010).
Wu, Lai-Chu, "ZAS: C 2 H 2 Zinc Finger Proteins Involved in Growth and Development," Gene Expressions, vol. 10: 137-152, (2002).
Yao, L. et al., "Schnurri transcription factors from *Drosophila* and vertebrates can mediate Bmp signaling through a phylogenetically conserved mechanism," Development, vol. 133: 4025-4034 (2006).
Patient, Roger K. et al., "The GATA Family (vertebrates and invertebrates)," Current Opinion in Genetics & Development, vol. 12:416-422 (2002).
Pearson, Helen, "Surviving a knockout blow," Nature, vol. 415:8-9 (2002).
Pessah, et al., "C-Jun associates with the oncoprotein Ski and suppresses Smad2 transcriptional activity," J. Biol. Chem., vol. 277(32):29094-100 (2002).
Polejaeva, I.A. et al., "New Advances in Somatic Cell Nuclear Transfer: Application in Transgenesis," Theriogenology, vol. 53:117-126 (2000).
Rayter, et al., "p21ras mediates control of IL-2 gene promoter function in T cell activation," EMBO J., vol. 11 (12):4549-56 (1992).
Reiner, Orly et al., "The evolving doublecortin (DCX) superfamily," BMC Genomics, vol. 7(188) doi:10.1186/1471-2164-7-188 (2006).
Rooney, et al, "Coordinate and cooperative roles for NF-AT and AP-1 in the regulation of the murine IL-4 gene," Immunity, vol. 2(5):473-83 (1995).
Rothe, et al., "A novel family of putative signal transducers associated with the cytoplasmic domain of the 75 kDa tumor necrosis factor receptor," Cell, vol. 78(4):681-92 (1994).
Rudinger J., "Characteristics of the amino acids as components of a peptide hormone sequence," Peptide Hormones, University Park Press, J.A. Parsons, Ed., Chpt. 1, pp. 1-7 (1976).
Rulicke, T. et al., "Germ line transformation of mammals by pronuclear microinjection," Experimental Physiology, vol. 85(6):589-601 (2000).
Schalkwyk, L.C. et al., "Interpretation of knockout experiments: the congenic footprint," Genes, Brain and Behavior, vol. 6:299-303 (2007).
Shi, Meng-Jiao et al., "CBFa3 (AML2) Is Induced by TGF-b1 to Bind and Activate the Mouse Germline Ig a Promoter," The Journal of Immunology, vol. 161:6751-6760 (1998).
Sigmund, Curt D., "Viewpoint: Are Studies in Genetically Altered Mice Out of Control?" Arterioscler. Thromb. Vasc. Biol., vol. 20:1425-1429 (2000).
Skolnick, Jeffrey et al., "From genes to protein structure and function: novel applications of computational approaches in the genomic era," TibTech, vol. 18:34-39 (2000).
Smith, Temple F. et al., "The challenges of genome sequence annotation or 'The devil is in the details,'" Nature Biotechnology, vol. 15:1222-1223 (1997).
Staehling-Hampton, et al., "A *Drosophila* protein related to the human zinc finger transcription factor PRDII/MBPI/HIV-EP1 is required for dpp signaling," Development, vol. 121(10):3393-403 (1995).
Sun, et al., "PKC-theta is required for TCR-induced NF-kappaB activation in mature but not immature T lymphocytes," Nature, vol. 404(6776):402-7 (2000).
Szabo, et al., "A novel transcription factor, T-bet, directs Th1 lineage commitment," Cell, vol. 100(6):655-69 (2000).
Takagi, et al., "Murine Schnurri-2 is required for positive selection of thymocytes," Nat. Immunol., vol. 2(11):1048-53 (2001).
Ting, Chao-Nan et al., "Transcription factor GATA-3 is required for development of the T-cell lineage," Nature, vol. 384:474-478 (1996).
Torres-Vazquez, et al., "Schnurri is required for dpp-dependent patterning of the *Drosophila* wing," Dev. Biol., vol. 227(2):388-402 (2000).
Torres-Vazquez, et al., "The transcription factor Schnurri plays a dual role in mediating Dpp signaling during embryogenesis," Development, vol. 128(9):1657-70 (2001).
Tsai, Fong-Ying et al., "Knock-in Mutation of Transcription Factor GATA-3 into the GATA-1 Locus: Partial Rescue of GATA-1 Loss of Function in Erythroid Cells," Developmental Biology, vol. 196:218-227 (1998).
Udagawa, et al., "Schnurri interacts with Mad in a Dpp-dependent manner," Genes Cells, vol. 5(5):359-69 (2000).
Ullman, Katharine S. et al., "Jun family members are controlled by a calcium-regulated, cyclosporin A-sensitive signaling pathway in activated T lymphocytes," Genes & Development, vol. 7(2):188-196 (1993).
Verma, Inder M. et al., "Gene therapy—promises, problems and prospects," Nature, vol. 389:239-242 (1997).
Wajant, et al., "TNF receptor associated factors in cytokine signaling," Cytokine Growth Factor Rev., vol. 10 (1):15-26 (1999).
Wall, R.J. et al., "Transgenic Dairy Cattle: Genetic Engineering on a Large Scale," J. Dairy Sci., vol. 80(9):2213-2224 (1997).
Wall, R.J., "Transgenic Livestock: Progress and Prospects for the Future," Thenogenology, vol. 45:57-68 (1996).
Wallach, et al., "Tumor necrosis factor receptor and Fas signaling mechanisms," Annu. Rev. Immunol., vol. 17:331-67 (1999).
Weiss, et al., "Regulation of c-Jun NH(2)-terminal kinase (Jnk) gene expression during T cell activation," J. Exp. Med., vol. 191(1):139-46 (2000).
Wells, James A. et al., "Additivity of Mutational Effects in Proteins," Biochemistry, vol. 29(37):8509-8517 (1990).
Wu, Xu et al., "A Small Molecule with Osteogenesis-Inducing Activity in Multipotent Mesenchymal Progenitor Cells," J. Am. Chem. Soc., vol. 124:14520-14521 (2002).
Wu, Jing et al., "HCO3-/Cl-anion exchanger SLC4A2 is required for proper osteoclast differentiation and function," Proceedings of the National Academy of Sciences, vol. 105(44):16934-16939 (2008).
Wu, et al., "IEX-1L, an apoptosis inhibitor involved in NF-kappaB-mediated cell survival," Science, vol. 281 (5379):998-1001 (1998).
Wu, Lai-Chu et al., "Molecular cloning of a zinc finger protein which binds to the heptamer of the signal sequence of V (D)J recombination," Nucleic Acids Research, vol. 21(22):5067-5073 (1993).
Wu, et al., "The DNA-binding ability of HIVEP3/KRC decreases upon activation of V(D)J recombination," Immunogenetics, vol. 53(7):564-71 (2001).
Wu, et al., "The mouse DNA binding protein Rc for the kappa B motif of transcription and for the V(D)J recombination signal sequences contains composite DNA-protein interaction domains and belongs to a new family of large transcriptional proteins," Genomics, vol. 35(3):415-24 (1996).
Wu, Lai-Chu et al., "The DNA-binding activity ability of HIVEP3/KRC decreases upon activation of V(D)J recombination," Immunogenetics, vol. 53:564-571 (2001).
Yanagimachi, R., "Cloning: experience from the mouse and other animals," Molecular and Cellular Endocrinology, vol. 187:241-248 (2002).
Yang, Xiangli et al., "ATF4 Is a Substrate of RSK2 and an Essential Regulator of Osteoblast Biology: Implication for Coffin-Lowry Syndrome," Cell, vol. 117:387-398 (2004).
Yeh, et al., "Early lethality, functional NF-kappaB activation, and increased sensitivity to TNF-induced cell death in TRAF2-deficient mice," Immunity, vol. 7(5):715-25 (1997).
Zhang, et al., "Smad3 and Smad4 cooperate with c-Jun/c-Fos to mediate TGF-beta-induced transcription," Nature, vol. 394(6696):909-13 (1998).

(56) References Cited

OTHER PUBLICATIONS

Zhang, Ying et al., "Transcriptional Regulation of the Transforming Growth Factor-b-inducible Mouse Germ Line Ig a Constant Region Gene by Functional Cooperation of Smad, CREB, and AML Family Members," The Journal of Biological Chemistry, vol. 275(22):16979-16985 (2000).

European Office Action for Application No. 08725690.5, 3 pages, dated Nov. 23, 2009.

International Preliminary Report on Patentability for Application No. PCT/US2004/036641, 4 pages, dated May 8, 2006.

International Preliminary Report on Patentability and Written Opinion for Application No. PCT/US2008/002082, 7 pages, dated Aug. 19, 2009.

International Preliminary Report on Patentability and Written Opinion for Application No. PCT/US2008/006783, dated Dec. 1, 2009.

International Search Report for Application No. PCT/US2008/002082, 9 pages, dated Mar. 23, 2009.

International Search Report for Application No. PCT/US04/36641, 2 pages, dated May 18, 2005.

\* cited by examiner

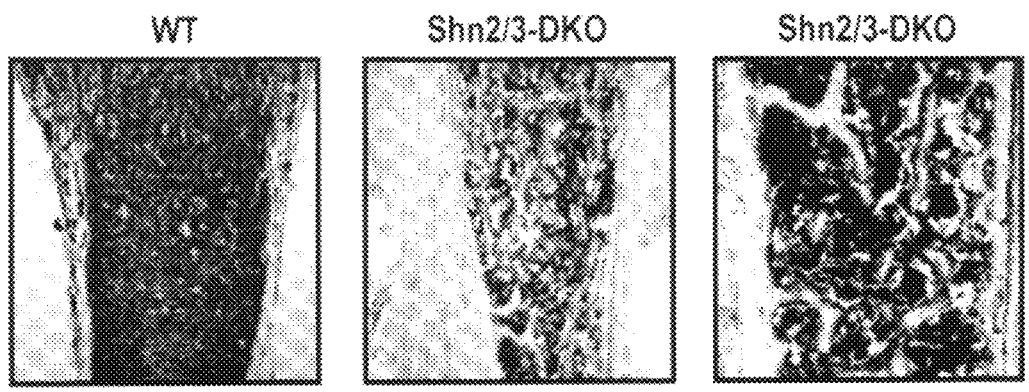
*Fig. 3F*  *Fig. 3G*  *Fig. 3H*
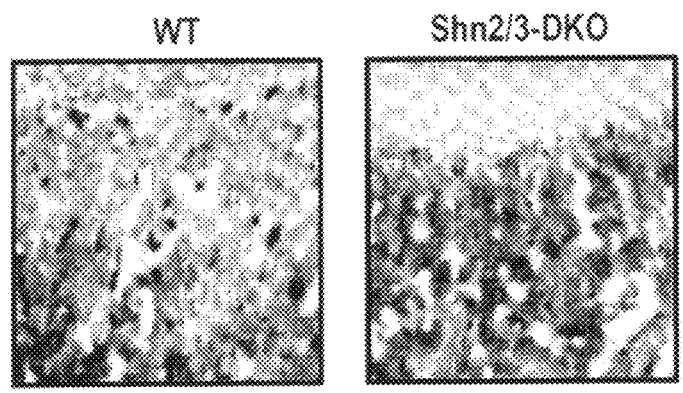
*Fig. 3I*  *Fig. 3J*

```
                       SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 1
gcaauaucca ccgcaucgut t                                                 21

<210> SEQ ID NO 2
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 2
acgaugcggu ggauauugct t                                                 21

<210> SEQ ID NO 3
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 3
ggaggguaca aaucgaaugt t                                                 21

<210> SEQ ID NO 4
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 4
cauucgauuu guacccucct t                                                 21

<210> SEQ ID NO 5
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 5
guauuugguc uuaugugaat t                                                 21
```

```
<210> SEQ ID NO 6
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 6
uucacauaag accaaauact t                                                 21

<210> SEQ ID NO 7
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 7
gaccaagagu aaucucuact t                                                 21

<210> SEQ ID NO 8
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 8
guagagauua cucuugguct t                                                 21

<210> SEQ ID NO 9
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 9
aucugauucu cucgagcagt t                                                 21

<210> SEQ ID NO 10
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 10
cugcucgaga gaaucagaut t                                                 21

<210> SEQ ID NO 11
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 11
gccaaaucac auccagcaut t                                                 21

<210> SEQ ID NO 12
<211> LENGTH: 21
<212> TYPE: DNA
<213> ORGANISM: Artificial Sequence
<220> FEATURE:
<223> OTHER INFORMATION: Synthetic siRNA sequence
```

```
<400> SEQUENCE: 12
augcuggaug ugauuuggct t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 13
uaauucauga agaaggggct t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 14
gccccuucuu caugaauuat t                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 15
uucaugaaga aggggcuggt t                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 16
ccagccccuu cuucaugaat t                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 17
gaaggggcug gauccguggt t                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 18
ccacggaucc agccccuuct t                                              21
```

METHODS FOR MODULATING SKELETAL REMODELING AND PATTERNING BY MODULATING SHN2 ACTIVITY, SHN3 ACTIVITY, OR SHN2 AND SHN3 ACTIVITY IN COMBINATION

RELATED APPLICATIONS

This application is a 35 U.S.C. §371 filing of International Application Number PCT/US2011/021056 which was filed on Jan. 13, 2011, which claims priority to, and the benefit of, Application No. 61/295,092, filed on Jan. 14, 2010. This application is related to U.S. application Ser. No. 11/918,503, entitled "Methods of Modulating Bone Formation and Mineralization by Modulating KRC Activity", Filed Oct. 12, 2007, PCT Patent Application No. PCT/US2008/005280, entitled "Assays for the Identification of Compounds that Modulate Bone Formation and Mineralization", filed Apr. 24, 2008, and U.S. patent application Ser. No. 12/156,008, entitled "Molecules Involved in the Regulation of Osteoblast and Osteoclast Activity and Methods of Use Thereof", filed May 29, 2008. The contents of each of these applications are hereby incorporated herein by reference.

BACKGROUND OF THE INVENTION

Transcription factors are a group of molecules within the cell that function to connect the pathways from extracellular signals to intracellular responses. Immediately after an environmental stimulus, these proteins which reside predominantly in the cytosol are translocated to the nucleus where they bind to specific DNA sequences in the promoter elements of target genes and activate the transcription of these target genes. One family of transcription factors, the ZAS (zinc finger-acidic domain structures) DNA binding protein family is involved in the regulation of gene transcription, DNA recombination, and signal transduction (Mak, C. H., et al. 1998. *Immunogenetics* 48: 32-39).

Zinc finger proteins are identified by the presence of highly conserved Cys2His2 zinc fingers (Mak, C. H., et al. 1998. *Immunogenetics* 48: 32-39). The zinc fingers are an integral part of the DNA binding structure called the ZAS domain. The ZAS domain is comprised of a pair of zinc fingers, a glutamic acid/aspartic acid-rich acidic sequence and a serine/threonine rich sequence (Mak, C. H., et al. 1998. *Immunogenetics* 48: 32-39). The ZAS domains have been shown to interact with the kB like cis-acting regulatory elements found in the promoter or enhancer regions of genes. The ZAS proteins recognize nuclear factor kB binding sites which are present in the enhancer sequences of many genes, especially those involved in immune responses (Bachmeyer, et al. 1999. *Nuc. Acid Res.* 27, 643-648). The ZAS DNA binding proteins have been shown to be transcription regulators of these target genes (Bachmeyer, et al. 1999. *Nuc. Acid Res.* 27, 643-648; Wu et al. 1998. *Science* 281, 998-1001).

The Schnurri family of large zinc-finger proteins consists of three mammalian homologues (Shn1/HIVEP1/MBP-1/PRDII-BF1/ZAS1, Shn2/HIVEP2/MBP-2/ZAS2 and Shn3/HIVEP3/KRC/ZAS3) (Liang, J., et al. (2003). Development 130, 6453-6464; Wu, L. C. (2002). Gene Expr. 10, 137-152) that are distantly related to Drosophila Shn, a protein that acts during embryogenesis as an essential nuclear cofactor for signaling by Decapentaplegic (Dpp), the Drosophila homologue of BMP/TGFβ. The broad expression pattern of the three mammalian Schnurri genes results in overlapping expression in multiple tissue and cell types. However, analysis of individual Schnurri-deficient mice has established that each Schnurri protein possesses unique roles in regulating multiple physiological processes including lymphocyte development, adipogenesis and bone formation.

One member of the mammalian Schnurri family is the zinc finger transcription factor Kappa Recognition Component (KRC) (also known as Shn3, schnurri 3 or Shn3, and human immunodeficiency virus type I enhancer-binding protein 3 (HIVEP3)). Shn3 is a member of the ZAS DNA binding family of proteins (Bachmeyer, et al. 1999. *Nuc. Acid Res.* 27, 643-648; Wu et al. 1998. *Science* 281, 998-1001) and has recently been identified as a key regulator of osteoblast function (Jones, et al. (2006) *Science* 312:1223-1227). Shn3−/− mice exhibit a pronounced high-bone mass phenotype that arises through augmentation of osteoblast synthetic activity. The osteosclerotic phenotype presents postnatally in the Shn3−/− mice, with onset of the phenotype occurring at 3-weeks of age and progressing in magnitude as the mice age.

Another member of the mammalian Schnurri family is Shn2. Shn2 deficiency has been shown to result in an overall reduction of bone remodeling by suppressing both osteoblastic bone formation and osteoclastic bone resorption activities, with a temporally limited mild increase in bone volume/tissue volume in the cancellous bone envelope in the metaphysis of 8- and 12-week-old mice. Shn2 deficiency was also been shown to suppress osterix and osteocalcin expression as well as bone mineralization in vitro (Siata, et al. (2007) J. Biol. Chem., 282:12907-12).

Further elucidation of the factors influencing skeletal patterning and remodeling and the identification of agents capable of modulating these pathways and methods of using such agents would be of great benefit in the treatment of bone disorders.

SUMMARY OF THE INVENTION

Shn3 has recently been identified as a key regulator of osteoblast function. Shn3$^{-/-}$ mice exhibit a pronounced high-bone mass phenotype that arises through augmentation of osteoblast synthetic activity. In contrast, Shn2 deficiency results in an overall reduction of bone remodeling by suppressing both osteoblastic bone formation and osteoclastic bone resorption activities Surprisingly, mice bearing a null mutation in Shn2 in combination with a null mutation in Shn3 exhibit a pronounced osteosclerotic phenotype. This phenotype results from augmented osteoblast activity and bone formation and displays accelerated onset and progression as compared to mice lacking only the Shn3 gene. This type of osteochondrodysplasia seen in mice bearing null mutations in both Shn2 and Shn3 is unique. Specifically, the deletion of Shn2 and Shn3 impairs growth plate maturation during endochondral ossification, but simultaneously results in massively elevated trabecular bone formation. These findings indicate that growth plate maturation and bone formation can be uncoupled under certain circumstances. Furthermore, the presence of this phenotype in the Shn2/3⁻ DKO mice but its absence in either Shn2$^{-/-}$Shn3$^{+/+}$ or Shn2$^{+/+}$Shn3$^{-/-}$ mice suggests that a compensatory role for Shn2 and Shn3 exists within the skeletal system. Therefore, the instant invention provides, inter alia, methods for modulating Shn2 activity alone, or in combination with modulation of Shn3 activity to effect modulation of bone remodeling and patterning.

In addition, although Shn3 was previously thought to play a role only in osteoblast regulation, the Examples presented herein demonstrate that Shn3 regulates osteoclasts in calvarie and diaphyseal bone. Specifically, reduction in Shn3 reduces osteoclast numbers and/or activity in these types of bone, but not in metaphyseal regions. In addition, it is demonstrated herein that Shn 3 binds to CREB and directly regulates its transcriptional activity and that Shn3 associates with RANKL gene regulatory elements.

Accordingly, in one aspect, the invention provides methods of identifying compounds useful in increasing trabecular bone formation and mineralization in a diaphysis of a bone comprising, a) providing an indicator composition comprising a Shn2 polypeptide, or biologically active portion thereof; b) contacting the indicator composition with each member of a library of test compounds; c) determining the ability of a compound to directly decrease the activity of the Shn2 polypeptide, or biologically active portion thereof, d) selecting from the library of test compounds a compound of interest that decreases the activity of the Shn2 polypeptide, or biologically active portion thereof, as compared to an appropriate control, thereby identifying compounds useful in increasing trabecular bone formation and mineralization in a diaphysis of a bone.

In another aspect, the invention provides methods of identifying compounds useful in decreasing trabecular bone formation and mineralization in a diaphysis of a bone comprising, a) providing an indicator composition comprising a Shn2 polypeptide, or biologically active portion thereof; b) contacting the indicator composition with each member of a library of test compounds; c) determining the ability of a compound to directly increase the expression and/or activity of the Shn2 polypeptide, or biologically active fragment thereof, d) selecting from the library of test compounds a compound of interest that increases the expression and/or activity of the Shn2 polypeptide, or biologically active portions thereof, as compared to an appropriate control, thereby identifying compounds useful in decreasing trabecular bone formation and mineralization in a diaphysis of a bone.

In one embodiment, the indicator composition is a cell that expresses the Shn2 polypeptide.

In one embodiment, the cell has been engineered to express the Shn2 polypeptide by introducing into the cell an expression vector encoding the Shn2 polypeptide.

In one embodiment, the indicator composition is a cell free composition.

In one embodiment, the indicator composition comprises an indicator cell, wherein the indicator cell comprises a Shn2 polypeptide and a reporter gene responsive to the Shn2 protein.

In one embodiment, the indicator cell contains: a recombinant expression vector encoding the Shn2 polypeptide; and a vector comprising a Shn2-responsive regulatory element operatively linked a reporter gene; and said method comprises: a) contacting the indicator cell with a test compound; b) determining the level of expression of the reporter gene in the indicator cell in the presence of the test compound;

c) comparing the level of expression of the reporter gene in the indicator cell in the presence of the test compound with the level of expression of the reporter gene in the indicator cell in the absence of the test compound.

In one embodiment, the method further comprises administering the compound to a non-human animal and determining the effect of test compound on bone formation and mineralization in the presence and absence of the test compound, wherein an increase in bone formation and mineralization in the non-human animal confirms the test compound of interest as a compound that increases bone formation and mineralization.

In one embodiment, the method further comprises administering the compound to a non-human animal and determining the effect of test compound on bone formation and mineralization in the presence and absence of the test compound, wherein a decrease in bone formation and mineralization in the non-human animal confirms the test compound of interest as a compound that decreases bone formation and mineralization.

In one embodiment, the non-human animal is a mouse deficient in Shn3.

In one embodiment, the method further comprises administering an agent which inhibits Shn3 activity to the non-human animal.

In one embodiment, the indicator cell is a mesenchymal stem cell.

In one embodiment, the indicator cell is a hematopoietic stem cell.

In one embodiment, the indicator cell is an osteoblast.

In one embodiment, the osteoblast is a mature osteoblast.

In one embodiment, the indicator cell is an osteoclast.

In one embodiment, bone formation and mineralization is determined by measuring trabecular number.

In one embodiment, bone formation and mineralization is determined by measuring trabecular thickness.

In one embodiment, bone formation and mineralization is determined by measuring trabecular spacing.

In one embodiment, bone formation and mineralization is determined by measuring bone volume.

In one embodiment, bone formation and mineralization is determined by measuring volumetric bone mineral density.

In one embodiment, bone formation and mineralization is determined by measuring trabecular number, measuring trabecular thickness, measuring trabecular spacing, measuring bone volume, and measuring volumetric bone mineral density.

In one embodiment, the effect of the test compound on bone formation and mineralization is determined by evaluating the ability of the test compound to decrease the differentiation of the mesenchymal stem cell into an osteoblast.

In one embodiment, the effect of the test compound on mesenchymal stem cell differentiation is determined by determining the level of cellular alkaline phosphatase (ALP).

In one embodiment, the effect of the test compound of interest on the level of cellular alkaline phosphatase (ALP) is evaluated by a colorimetric assay.

In one embodiment, the method further comprises normalizing cell number to the level of cellular alkaline phosphatase (ALP) by Alamar blue staining.

In one embodiment, the effect of the compound on bone formation and mineralization is determined by evaluating the ability of the test compound to increase the differentiation of the hematopoietic stem cell into an osteoclast.

In one embodiment, the effect of the test compound of interest on hematopoietic stem cell differentiation is evaluated by determining the level of TRAP.

In one embodiment, the effect of the test compound of interest on the level of TRAP is evaluated by a colorimetric assay.

In one embodiment, the method further comprises normalizing cell number to the level of TRAP by Alamar blue staining.

In one embodiment, the method further comprises evaluating the effect of the test compound of interest on the formation of resorption lacunae.

In one embodiment, the step of evaluating the effect of the test compound of interest on the formation of resorption lacunae is determined by von Kossa staining.

In one embodiment, the step of evaluating the effect of the test compound of interest on mineralization is determined by xylenol orange staining.

In one embodiment, the step of determining the serum levels of Trabp5b and deoxypyridinoline (Dpd).

In another aspect, the invention pertains to a method for increasing trabecular bone formation and mineralization in the diaphysis of a bone, comprising contacting an osteoblast with an agent that decreases the expression and/or biological activity of Shn2 in the osteoblast such that bone formation and mineralization is increased, wherein the agent is selected from the group consisting of: a nucleic acid molecule that is antisense to a Shn2 molecule, a Shn2 siRNA molecule, a dominant negative Shn2 molecule, or combinations thereof.

In one embodiment, the method further comprises contacting the osteoblast with an agent that decreases the biological activity of Shn3 in the osteoblast, wherein the agent is selected from the group consisting of: a nucleic acid molecule that is antisense to a Shn3 molecule, a Shn3 siRNA molecule, a dominant negative Shn3 molecule, or combinations thereof.

In another aspect, the invention pertains to methods for treating or preventing a disease, disorder, condition, or injury that would benefit from increased trabecular bone formation and mineralization in the diaphysis of a bone in a subject, comprising contacting an osteoblast from the subject with an agent that decreases the expression and/or biological activity of Shn2 in the osteoblast such that the trabecular bone formation and mineralization in the diaphysis of the bone in the subject is increased, wherein the agent is selected from the group consisting of: a nucleic acid molecule that is antisense to a Shn2 molecule, a Shn2 siRNA molecule, a dominant negative Shn2 molecule, or combinations thereof.

In one embodiment, the method further comprises contacting the osteoblast with an agent that decreases the biological activity of Shn3 in the osteoblast, wherein the agent is selected from the group consisting of: a nucleic acid molecule that is antisense to a Shn3 molecule, a Shn3 siRNA molecule, a dominant negative Shn3 molecule, or combinations thereof.

In one embodiment, the step of contacting occurs in vitro.

In one embodiment, the step of contacting occurs in vivo.

In one embodiment, the agent is present on a surface.

In one embodiment, the disease, disorder, condition, or injury is selected from the group consisting of: osteoporosis, osteopenia, osteomalacia, and osteitis deformans (Paget's disease of bone), osteoarthritis and inflammatory arthritides characterized by bone loss or excess bone formation including for example rheumatoid arthritis, ankylosing spondylitis, psoriatic arthritis In another aspect, the invention pertains to methods of identifying compounds useful in selectively decreasing osteoclast activity in calvariae and diaphyseal bone comprising,
a) providing an indicator composition comprising a Shn3 polypeptide, or biologically active portion thereof;
b) contacting the indicator composition with each member of a library of test compounds;
c) determining the ability of a compound to directly decrease the expression and/or activity of the Shn3 polypeptide, or biologically active fragment thereof,
d) selecting from the library of test compounds a compound of interest that decreases the expression and/or activity of the Shn3 polypeptide, or biologically active portions thereof, as compared to an appropriate control;
e) testing the ability of the compound to reduce osteoclast activity in at least one of calvariae and diaphyseal bone
thereby identifying compounds useful in selectively decreasing osteoclast activity in calvariae and diaphyseal bone.

In one embodiment, the indicator composition is a cell that expresses the Shn3 polypeptide.

In one embodiment, the cell has been engineered to express the Shn3 polypeptide by introducing into the cell an expression vector encoding the Shn3 polypeptide.

In one embodiment, the indicator composition is a cell free composition.

In another embodiment, the indicator composition comprises an indicator cell, wherein the indicator cell comprises a Shn3 polypeptide and a reporter gene responsive to the Shn3 protein.

In yet another embodiment, the indicator cell contains: a recombinant expression vector encoding the Shn3 polypeptide; and a vector comprising a Shn3-responsive regulatory element operatively linked a reporter gene; and said method comprises:
a) contacting the indicator cell with a test compound;
b) determining the level of expression of the reporter gene in the indicator cell in the presence of the test compound;
c) comparing the level of expression of the reporter gene in the indicator cell in the presence of the test compound with the level of expression of the reporter gene in the indicator cell in the absence of the test compound.

In one embodiment, the Shn3-responsive regulatory element comprises the RANKL gene regulatory element.

In another embodiment, the invention pertains to methods of identifying compounds useful in selectively decreasing osteoclast activity in calvariae and diaphyseal bone comprising
a) providing an indicator composition comprising a Shn3 polypeptide, or biologically active portion thereof and a CREB popypeptide;
b) contacting the indicator composition with each member of a library of test compounds;
c) determining the ability of a compound to directly decrease the interaction of the Shn3 polypeptide, or biologically active fragment thereof, with the CREB polypeptide or biologically active portion thereof;
d) selecting from the library of test compounds a compound of interest that decreases the interaction of the Shn3 polypeptide, or biologically active portion thereof, with the CREB polypeptide or biologically active portion thereof as compared to an appropriate control, to thereby identify compounds useful in selectively decreasing osteoclast activity in calvariae and diaphyseal bone.

In another aspect, the invention pertains to methods for treating or preventing a disease, disorder, condition, or injury associated with osteoclastic bone destruction in calvariae or diaphyseal bone in a subject, comprising administering to the subject an agent that decreases the expression and/or biological activity of Shn3 in an amount sufficient to decrease expression of RANKL, wherein the agent is selected from the group consisting of: a nucleic acid molecule that is antisense to a Shn3 molecule, a Shn3 siRNA molecule, a dominant negative Shn3 molecule, or combinations thereof, to thereby treat or preventing a disease, disorder, condition, or injury associated with osteoclastic bone destruction in calvariae or diaphyseal bone in a subject.

Figure 10A:
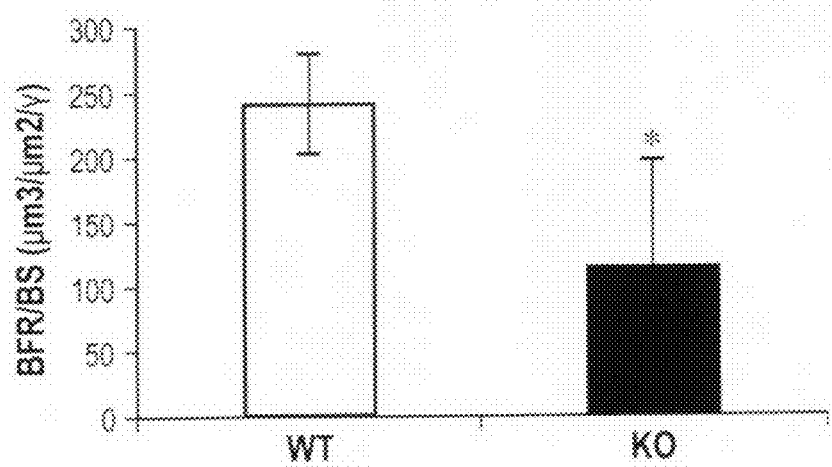
Figure 10B:
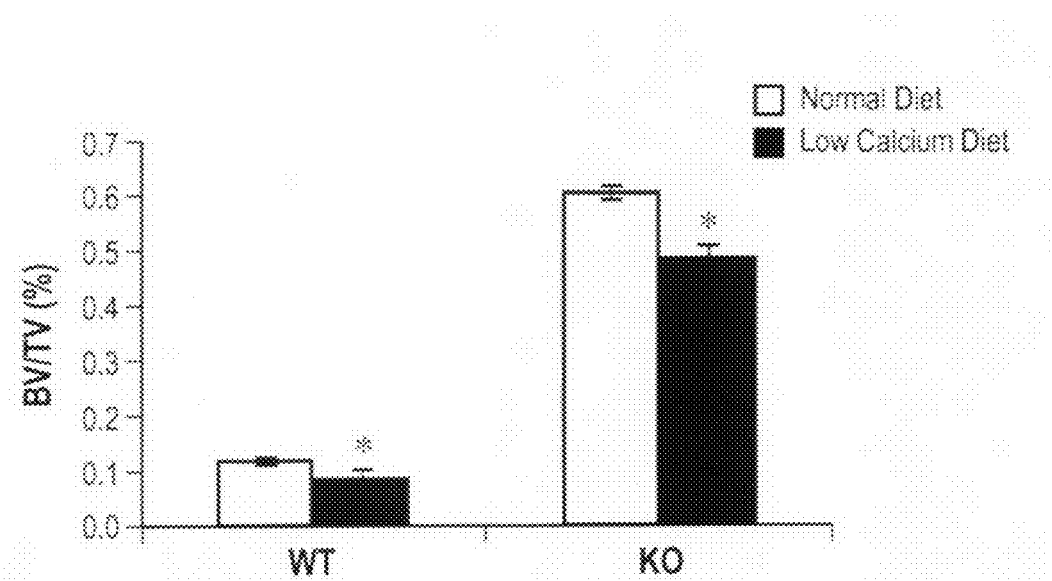

FIG. 10. In vivo analysis of Shn3-deficient mice challenged with resorptive stimuli. (A) Dynamic histomorphometry was performed to quantify bone formation rate in 12 week old WT and Shn3−/− (KO) animals, n=5 mice/group. * denotes p<0.05. (B) 11 week old WT and Shn3−/− (KO) mice were fed with a normal or low calcium diet for 2 weeks. BV/TV in the distal femoral metaphysis was determined by μCT, n=5 mice/group. * denotes p<0.05. (C) 6 month old WT (n=6) or Shn3−/− (KO, n=8) mice were injected with botulinum toxin in the calf hindlimb. At day 0 (just before toxin injection) and day 21, the indicated parameters were determined by μCT at metaphyseal region of the proximal tibia. Data are expressed as percent change of the indicated parameter due to calf paralysis. * denotes p<0.05.

DETAILED DESCRIPTION OF THE INVENTION

Shn2 deficiency has been shown to result in an overall reduction of bone remodeling by suppressing both osteoblastic bone formation and osteoclastic bone resorption activities, with a temporally limited mild increase in bone volume/tissue volume in the cancellous bone envelope in the metaphysis of 8- and 12-week-old mice (Siata, et al. (2007) J. Biol. Chem., 282:12907-12). Surprisingly, as described herein, mice that lack both Shn2 and Shn3 have a phenotype more similar to Shn3 null mice in that they develop an osteosclerotic phenotype. However, analysis of the diaphyses of trabecular bone isolated from mice bearing null mutations in both Shn2 and Shn3 revealed an accelerated and progressive development of an osteosclerotic phenotype at each age analyzed when compared to age and sex matched $Shn3^{+/-}$ and $Shn3^{-/-}$ mice. The growth plate defects that are observed in the Shn2/3–DKO mice share similarities with other mouse models of chondrodysplasia, however, the Shn2/3-null (double knock out (DKO)) mice are unique in that an increased trabecular bone mass is observed in the same skeletal elements where chondrocyte proliferation and maturation is disrupted. Furthermore, the presence of this phenotype in the Shn2/3–DKO mice but its absence in either $Shn2^{-/-}Shn3^{+/+}$ or $Shn2^{+/+}Shn3^{-/-}$ mice suggests that a compensatory role for Shn2 and Shn3 exists within the skeletal system.

Accordingly, the present invention provides methods for decreasing trabecular bone formation and mineralization in a diaphysis of a bone, methods for decreasing growth plate maturation during endochondral ossification, methods of treating or preventing a disease, disorder, condition, or injury that would benefit from increased trabecular bone formation and mineralization in a diaphysis of a bone, methods for increasing growth plate maturation during endochondral ossification as well as methods of identifying compounds useful in modulating (e.g., increasing or decreasing) trabecular bone formation and mineralization in a diaphysis of a bone or for decreasing growth plate maturation during endochondral ossification. The agents identified as useful for modulating Shn2 activity using the methods described herein may be used alone or may be particularly effective when used in combination with agents that modulate Shn3 activity.

In addition, the Examples presented herein demonstrate that Shn3 regulates osteoclasts in calvarie and diaphyseal bone. Specifically, reduction in Shn3 reduces osteoclast numbers and/or activity in these types of bone, but not in metaphyseal regions. In addition, it is demonstrated herein that Shn3 binds to CREB and directly regulates its transcriptional activity and that Shn3 associates with RANKL gene regulatory elements.

Various aspects of the invention are described in further detail in the following subsections:

I. Definitions

As used herein, the term "Shn2" is used interchangeably with "Shn2" or "Schnurri 2", and is also known as HIV-EP2, MBP-2, MIBP1, ZAS2, Human immunodeficiency virus type I enhancer-binding protein 2, MHC binding protein-2, MHC-binding protein 2, c-myc intron binding protein 1. "Shn2" is a DNA binding protein and is a member of a family of the "ZAS zinc finger protein family". ZAS zinc finger protein family members have each been shown to bind to the kB like cis-acting regulatory elements found in the promoter or enhancer regions of genes (e.g., a consensus sequence 5'-GGG(N4-5)CC-3') and have been implicated in cell growth, signal transduction and lymphocyte development (Allen and Wu (2005) in Zinc Finger Proteins: From Atomic Contact to Cellular Function eds. Iuchi and Kuldell, pages 213-220).

ZAS family members contain a ZAS domain, which is a modular protein structure consisting of four C2H2 zinc fingers, which are divided into two pairs with an acidic-rich region and a serine/threonine-rich sequence. Shn2 also contains a leucine zipper motif.

The nucleotide and amino acid sequences of human Shn2 are known and may be found in, for example, GenBank entry gi:110347462. The nucleotide and amino acid sequences of mouse and rat Shn2 are also known and may be found in, for example, GenBank entries gi:85861240 and gi:13162313, respectively.

The C2H2 zinc finger domains of Shn2 are at amino acid residues 189-211, 217-239, 1799-1821, and 1827-1851 of gi:110347462. The Glu/Asp rich region of Shn2 is located at amino acid residues 1899-1923 of gi:110347462. The SPXK motifs of Shn2 are at amino acid residues 2053-2148 of gi:110347462.

The C2H2 zinc finger domains of mouse Shn2 are at amino acid residues 189-211, 217-239, 1783-1805, 1811-1835 of gi:85861240. The Glu/Asp rich region of Shn2 is located at amino acid residues 2037-2132 of gi:85861240. The SPXK motifs of Shn2 are at amino acid residues 2053-2148 of gi:85861240.

The C2H2 zinc finger domains of rat Shn2 are at amino acid residues 189-211, 217-239, 1790-1812, 1818-1842 of gi:13162313. The Glu/Asp rich region of Shn2 is located at amino acid residues 1890-1914 of gi:13162313. The SPXK motifs of Shn2 are at amino acid residues 2044-2139 of gi:13162313.

In one embodiment, Shn2 polypeptides comprise one or more of the following Shn2 characteristics: a pair of Cys2-His2 zinc fingers followed by a Glu- and Asp-rich acidic domain and ten copies of the Ser/Thr-Pro-X-Arg/Lys (SPXK motif) sequence thought to bind DNA.

Accordingly, as used herein, the term "Shn2 activity", "Shn2 biological activity" or "activity of a Shn2 polypeptide" includes the ability to modulate an activity regulated by Shn2. For example, in one embodiment a Shn2 biological activity includes modulation of bone formation and mineralization. In one embodiment, a Shn2 biological activity is modulation of trabecular bone formation and mineralization.

In one embodiment, modulation of trabecular bone formation and mineralization is modulation of trabecular bone formation and mineralization in the diaphysis of a bone. In one embodiment, Shn2 activity can be modulated by modulating the level of expression of Shn2 in a cell.

In one embodiment, the Shn2 activity is a direct activity, such as an association with a Shn2-target molecule or binding partner, e.g., NF-kB, Smad1, Smad4, Cebpa, PPAR-gamma (promoter). As used herein, a "target molecule", "binding partner" or "Shn2 binding partner" is a molecule with which a Shn2 protein binds or interacts in nature such that Shn2 mediated function is achieved.

As used herein, the term "KRC", used interchangeably with "Shn3" or "Schnurri 3", refers to κB binding and putative recognition component of the V(D)J. Rss. The nucleotide and amino acid sequence of human, mouse and rat KRC are known and can be found in, for example, GenBank Accession No.: gi: 189181749 (human), gi:189181748 (human), gi:124107624 (mouse), and gi:15781850 (rat). Biological activities of Shn3 include, modulation of TNFα production, modulation of IL-2 production, modulation of an NFkB signaling pathway, modulation of a TGFβ signaling pathway, modulation of degradation of GATA3, modulation of effector T cell function, modulation of apoptosis, or modulation of T cell differentiation, modulation of IgA germline transcription, modulation of bone formation and mineralization, modulation of osteoclastogenesis, modulation of osteoblast activity, modulation of osteocalcin gene transcription, modulation of the degradation of Runx 2, e.g., modulation of Runx2 protein levels, modulation of the ubiquitination of Runx2, modulation of WWP1 activity, e.g., ubiquitination activity of WWP1, modulation of the expression of RSK2, degradation of RSK2, e.g., modulation of RSK2 protein levels, ubiquitination of RSK2, modulation of the phosphorylation of RSK2, modulation of RSK2 kinase activity, modulation of the expression of BSP, ColI(α)1, OCN, Osterix, RANKL, and ATF4, modulation of ATF4 protein levels, and/or modulation of the phosphorylation of ATF4. The expression and/or activity of Shn3 may be determined as described in, for example, PCT International Application Nos. PCT/US2008/005280 and PCT/US2008/06783, the contents of which are expressly incorporated herein by reference.

Bone is a dynamic tissue whose matrix components are continuously being remodeled to preserve the structural integrity of the skeleton. For example, bone formation and/or growth takes place at the epiphyseal growth plate of long bones by a finely balanced cycle of cartilage growth, matrix formation and calcification of cartilage that acts as a scaffold for bone formation. This sequence of cellular events constitutes endochondral ossification. In addition bone is being continuously resorbed and replaced by new bone. This process is referred to as modeling (also referred to herein as "remodeling"). Modelling is most active during childhood and adolescence, and enables long bones to increase in diameter, to change shape and develop a marrow cavity. Modelling continues throughout adult life with bone resorption equally balanced by bone formation in a healthy skeleton. "Bone remodeling" is a cyclical process where under normal physiological conditions, bone formation occurs only at sites where bone resorption has previously taken place.

As used herein, the term "bone formation and mineralization" or "bone growth and mineralization" refers to the cellular activity of osteoblasts to synthesize the collagenous precursors of bone extracellular matrix, e.g., ossification, e.g., endochondral ossification, intramembranous ossification, regulate mineralization of the matrix to form bone, as well as their function in bone remodeling and reformation, e.g., bone mass is maintained by a balance between the activity of osteoblasts that form bone and the osteoclasts that break it down. In one embodiment, bone formation and mineralization is ossification. In another embodiment, bone formation and mineralization is remodeling. In another embodiment, bone formation and mineralization is ossification and remodeling.

The mineralization of bone occurs by deposition of carbonated hydroxyapetite crystals in an extracellular matrix consisting of type I collagen and a variety of non-collagenous proteins.

Bone is an organ composed of cortical and trabecular bone, cartilage, haemopoetic and connective tissues (Ham, 1974). These tissues enable the skeleton to serve its main functions that include the protection of internal organs, movement of parts of the body, and the provision of a site for haematopoesis. All bones are derived from mesenchyme by two different processes, endochondral ossification (e.g., the process used to make long bones, the pelvic bones and the vertebrae) (from cartilage derived from mesenchyme) and intramembranous ossification (e.g., the process used to make flat bones such as the mandible and flat bones of the skull) (directly from mesenchyme).

More specifically, during endochondral ossification, the embryonic primordiae of the appendicular skeleton are the limb buds, which are mesodermal structures covered by ectoderm. The first visible outline of the embryonic limb follows a condensation of mesenchymal cells which subsequently differentiate into cartilage cells, the chondrocytes. These cells secrete a matrix and so produce cartilaginous models of the future bones. Surrounding this cartilage is the perichondrium, the outer layer of which becomes a connective tissue sheath while the inner cells remain pluripotential. This cartilage rudiment grows by interstitial and appositional growth, and a vascular system develops to invade the perichondrium. A collar of bone is then laid down around the mid-shaft of the bone. This ossification is a result of the inner perichondrial cells differentiating into bone forming cells, the osteoblasts. At the same time the osteoblasts, together with capillaries, invade the centre of the shaft to form a primary, or diaphyseal ossification centre, at a site where the cartilage cells and matrix have begun to disintegrate. Trabecular bone is then deposited on cartilaginous remnants. The embryonic bone increases in width by appositional growth, and the central cancellous bone core gradually becomes resorbed to form a marrow cavity. The shaft of the bone ossified from the primary ossification center is the "diaphysis", which grows as the bone develops.

Secondary ossification centers also appear in other parts of the developing bone after birth. The parts of the bone ossified from these centers are the "epiphyses". The flared part of the diaphysis nearest the epiphysis is the "metaphysis" where the diaphyseal diameter increases to that of the epiphyses. The flared region corresponds to the level where bony trabeculae are present on the diaphyseal side of the epiphyseal plate. Throughout bone formation and mineralization, the metaphyses retain the same general shape because osteoclasts resorb bone from the periphery of the metaphysis until its diameter is reduced to that of the shaft. New bone concurrently built on the medullary surface of the metaphysis compensates for bone removal from the periphery. For growth to continue, the bone formed from the primary center in the diaphsysis does not fuse with that formed from the secondary centers in the epiphysis until the bone reaches adult size. Thus, during growth of a long bone, epiphyseal plates intervene between the diaphysis and epiphysis. This process also occurs during, e.g., remodeling, fracture repair of, e.g., long bones.

During intramembranous ossification, embryologic mesenchymal cells (MSC) condense into layers of vascularized primitive connective tissue. Certain mesenchymal cells group together, usually near or around blood vessels, and differentiate into osteogenic cells which deposit bone matrix constitutively. These aggregates of bony matrix are called bone spicules. Separate mesenchymal cells differentiate into osteoblasts, which line up along the surface of the spicule and secrete more osteoid, which increases the size of the spicule.

As the spicules continue to grow, they fuse with adjacent spicules and this results in the formation of trabeculae. When osteoblasts become trapped in the matrix they differentiate into osteocytes. Osteoblasts continue to line up on the surface which increases the size. As growth continues, trabeculae become interconnected and woven bone is formed. The term primary spongiosa is also used to refer to the initial trabecular network.

The periosteum is formed around the trabeculae by differentiating mesenchymal cells. The primary center of ossification is the area where bone growth occurs between the periosteum and the bone. Osteogenic cells that originate from the periosteum increase appositional growth and a bone collar is formed. The bone collar is eventually mineralized and lamellar bone is formed.

Osteons are units or principal structures of compact bone. During the formation of bone spicules, cytoplasmic processes from osteoblasts interconnect. This becomes the canaliculi of osteons. Since bone spicules tend to form around blood vessels, the perivascular space is greatly reduced as the bone continues to grow. When replacement to compact bone occurs, this blood vessel becomes the central canal of the osteon. This process also occurs during, e.g., remodeling, fracture repair of, e.g., flat bones.

Bone is not a uniformly solid material, but rather has some spaces between its hard elements. There are two main types of bone or osseous tissue.

The hard outer layer of bones is composed of "compact bone" tissue, so-called due to its minimal gaps and spaces. It is extremely hard, formed of multiple stacked layers with few gaps. Its main function is to support the body, protect organs, provide levers for movement, and (shared with cancellous bone) store minerals. This tissue gives bones their smooth, white, and solid appearance, and accounts for 80% of the total bone mass of an adult skeleton. Compact bone may also be referred to as "dense bone" or "cortical bone".

Filling the interior of bones, such as long bones, the pelvis and vertebrae, is the "trabecular bone" tissue (an open cell porous network also called "cancellous bone" or "spongy bone") which is composed of a network of rod- and plate-like elements that make the overall organ lighter and allows room for blood vessels and marrow. Trabecular bone accounts for the remaining 20% of total bone mass, but has nearly ten times the surface area of compact bone.

In one embodiment bone formation and mineralization is trabecular bone formation and mineralization. In another embodiment, bone formation and mineralization is cortical bone formation and mineralization.

As described above, bones, e.g., long bones, are divided into regions including the diaphysis, epiphysis, and metaphysis. "Epiphysis" is the name for a rounded end of a long bone. The epiphysis is filled with red bone marrow, which produces erythrocytes, or red blood cells.

The "metaphysis" is the portion of a long bone between the epiphyses and the diaphysis. The "growth plate", or "physis", or "epiphyseal plate", although it precedes the development of the ossified metaphysis, may also be referred to as the metaphysis. It is this part of the bone that grows during childhood; as it grows, it ossifies near the diaphysis and the epiphyses. At roughly 18 to 25 years of age, the metaphysis stops growing altogether and completely ossifies into solid bone. "Epiphyseal plates" ("growth plates") are located in the metaphysis and are responsible for growth in the length of the bone.

The "diaphysis" is the main or mid section (shaft) of a long bone. It is made up of cortical bone and usually contains bone marrow and adipose tissue.

Each of these regions of bone may be identified histologically and/or morphologically by, e.g., radiography, using techniques known in the art and described herein.

There are several types of cells constituting the bone. For example, osteogenic cells respond to traumas, such as fractures, by giving rise to osteoblasts and osteoclasts. Osteoblasts synthesize and secrete unmineralized ground substance and are found in areas of high metabolism within the bone. Osteocytes are mature bone cells made from osteoblasts that have made bone tissue around themselves. These cells maintain healthy bone tissue by secreting enzymes and controlling the bone mineral content; they also control the calcium release from the bone tissue to the blood. Osteoclasts are large cells that break down bone tissue. They are very important to bone growth, healing, and remodeling. The last type of cells are bone-lining cells. These are made from osteoblasts along the surface of most bones in an adult. Bone-lining cells regulate the movement of calcium and phosphate into and out of the bone. However, homeostatic remodeling of the skeleton is mediated primarily, if not exclusively, by the osteoclast and the osteoblast (Erlebacher, A., et al. (1995). *Cell* 80, 371-378).

As used herein, an "osteoclast" is a large multinucleated cell of hematopoietic origin with abundant acidophilic cytoplasm, functioning in the absorption and removal of osseous tissue ("bone resorption"). Osteoclasts become highly active in the presence of parathyroid hormone, causing increased bone resorption and release of bone salts (phosphorus and, especially, calcium) into the extracellular fluid.

As used herein, an "osteoblast" is a bone-forming cell that is derived from mesenchymal osteoprognitor cells and forms an osseous the matrix constituents on bone forming surfaces in which it becomes enclosed as an osteocyte. A mature osteoblast is is one capable of forming bone extracellular matrix in vivo, and can be identified in vitro by its capacity to form mineralized nodules which reflects the generation of extracellular. An immature osteoblast is not capable of forming mineralized nodules in vitro.

Proliferation, differentiation and bone remodeling activities of these cells involve a complex temporal network of growth factors, signaling proteins, and transcription factors (Karsenty, G., and Wagner, E. F. (2002). *Dev Cell* 2, 389-406). Dysregulation of any one component may disrupt the remodeling process and contribute to the pathogenesis of certain skeletal disorders, such as osteoporosis and Paget's disease. Rare single gene disorders resulting in elevated bone mass due to osteoclast defects, collectively termed osteopetrosis, have been identified. Rarer are single gene disorders, exemplified by Camerati-Engelman syndrome, collectively termed osteosclerosis, in which elevated bone mass is due to intrinsically-elevated osteoblast activity.

As used herein, the various forms of the term "modulate" are intended to include stimulation (e.g., increasing or upregulating a particular response or activity) and inhibition (e.g., decreasing or downregulating a particular response or activity).

The term "interact" as used herein is meant to include detectable interactions between molecules, such as can be detected using, for example, a yeast two hybrid assay or coimmunoprecipitation. The term interact is also meant to include "binding" interactions between molecules. Interactions may be protein-protein or protein-nucleic acid in nature.

As used herein, the term "contacting" (i.e., contacting a cell e.g. an immune cell, with an compound) is intended to include incubating the compound and the cell together in vitro (e.g., adding the compound to cells in culture) or administering the compound to a subject such that the compound and cells of the subject are contacted in vivo. The term "contacting" is not intended to include exposure of cells to a Shn2 modulator that may occur naturally in a subject (i.e., exposure that may occur as a result of a natural physiological process).

As used herein, the term "test compound" includes a compound that has not previously been identified as, or recognized to be, a modulator of Shn2 activity and/or expression and/or a modulator of bone growth and/or mineralization.

The term "library of test compounds" is intended to refer to a panel or pool comprising a multiplicity of test compounds.

As used herein, the term "cell free composition" refers to an isolated composition which does not contain intact cells. Examples of cell free compositions include cell extracts and compositions containing isolated proteins.

As used herein, the term "indicator composition" refers to a composition that includes a protein of interest (e.g., Shn2 or Shn3), for example, a cell that naturally expresses the protein, a cell that has been engineered to express the protein by introducing an expression vector encoding the protein into the cell, or a cell free composition that contains the protein (e.g., purified naturally-occurring protein or recombinantly-engineered protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, nucleic acid molecule of the invention is an siRNA molecule. In one embodiment, a nucleic acid molecule of the invention mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described herein for use in antisense RNA can be employed in molecules that mediate RNAi.

As used herein, the term "transgenic cell" refers to a cell containing a transgene.

As used herein, a "transgenic animal" includes an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

In one embodiment, small molecules can be used as test compounds. The term "small molecule" is a term of the art and includes molecules that are less than about 7500, less than about 5000, less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., Cane et al. 1998. Science 282:63), and natural product extract libraries. In another embodiment, the compounds are small, organic non-peptidic compounds. In a further embodiment, a small molecule is not biosynthetic. For example, a small molecule is preferably not itself the product of transcription or translation.

II. Screening Assays

Modulators of Shn2 and/or Shn3 activity can be known (e.g., dominant negative inhibitors of Shn2 or Shn3 activity, antisense Shn2 or Shn3 intracellular antibodies that interfere with activity, peptide inhibitors derived from Shn2 or Shn3) or can be identified using the methods described herein. The invention provides methods (also referred to herein as "screening assays") for identifying other modulators, i.e., candidate or test compounds or agents (e.g., peptidomimetics, small molecules or other drugs) which modulate Shn2 or Shn3 activity and for testing or optimizing the activity of other agents.

NF-kB, GATA3, SMAD4, SMAD1, Cebpa, osterix, osteocalcin, PPAR-gamma function in a signal transduction pathway involving Shn2. CREB, TRAF, NF-kB, JNK, GATA3, SMAD2, SMAD3, CBFβ, JNK, TGFβ, ATF4, RSK2, and/or AP-1 function in a signal transduction pathway involving Shn3. Therefore, in one embodiment, any of these molecules can be used in the subject screening assays. Although the specific embodiments described below in this section and in other sections may list one of these molecules as an example, other molecules in a signal transduction pathway involving Shn2 or Shn3 can also be used in the subject screening assays.

In one embodiment, the ability of a compound to directly modulate the expression or activity of Shn2 or Shn3 is measured in an indicator composition using a screening assay of the invention.

The indicator composition can be a cell that expresses the Shn protein (Shn2 and/or Shn3), for example, a cell that naturally expresses or, more preferably, a cell that has been engineered to express the protein by introducing into the cell an expression vector encoding the protein. Preferably, the cell is a mammalian cell, e.g., a human cell. In one embodiment, the cell is an osteoblast. In another embodiment, the cell is a mature osteoblast. In one embodiment, the cell is a hematopoietic stem cell. In one embodiment the cell is a mesenchymal stem cell. In one embodiment, the cell is a prenatal cell. In one embodiment, the cell is a postnatal cell. Alternatively, the indicator composition can be a cell-free composition that includes the protein (e.g., a cell extract or a composition that includes e.g., either purified natural or recombinant protein).

Compounds identified using the assays described herein can be useful for treating disorders associated with aberrant expression, post-translational modification, or activity of Shn 2 or 3 or a molecule in a signaling pathway involving Shn2 or 3 e.g.: disorders that would benefit from modulation of trabecular bone formation and mineralization in the diaphysis of a bone, modulation of osteoclastogenesis, modulation of osteoblast versus osteoclast activity.

Conditions that can benefit from modulation of a signal transduction pathway involving Shn2 include diseases, disorders, conditions, or injuries in which modulation of trabecular bone formation and mineralization in the diaphysis of a bone would be beneficial.

In another aspect, the invention pertains to a combination of two or more of the assays described herein. For example, a modulating agent can be identified using a cell-based or a cell-free assay, and the ability of the agent to modulate the activity of Shn2 or Shn3 can be confirmed in vivo, e.g., in an animal, such as, for example, an animal model for, e.g., osteoporosis or osteopetrosis.

Moreover, a modulator of Shn2 or Shn3 or identified as described herein (e.g., an antisense nucleic acid molecule, or a specific antibody, or a small molecule) can be used in an animal model to determine the efficacy, toxicity, or side effects of treatment with such a modulator. Alternatively, a modulator identified as described herein can be used in an animal model to determine the mechanism of action of such a modulator.

In another embodiment, it will be understood that similar screening assays can be used to identify compounds that indirectly modulate the activity and/or expression of Shn2 or Shn3 e.g., by performing screening assays such as those described above using molecules with which Shn2 or Shn3 interacts, e.g., molecules that act either upstream or downstream of Shn2 or Shn3 in a signal transduction pathway.

The cell based and cell free assays of the invention are described in more detail below.

1. Cell Based Assays

The indicator compositions of the invention can be cells that express at least one of a Shn2 protein, Shn3 protein, or non-Shn2 or Shn3 protein in the Shn2 or Shn3 signaling pathway (such as, e.g., NF-kB, GATA3, SMAD4, SMAD1, Cebpa, osterix, osteocalcin, and/or PPAR-gamma for Shn2 or CREB, TRAF, NF-kB, JNK, GATA3, SMAD2, SMAD3, CBFβ, JNK, TGFβ, ATF4, RSK2, and/or AP-1 for Shn3. For example, a cell that naturally expresses the endogenous molecule or, more preferably, a cell that has been engineered to express an exogenous protein by introducing into the cell an expression vector encoding the protein(s). Alternatively, the indicator composition can be a cell-free composition that includes at least one of a Shn2 or Shn3 or a non-Shn2 or Shn3 protein, either natural or recombinant protein).

Compounds that modulate expression and/or activity of Shn2 and/or Shn3 can be identified using various "readouts."

For example, an indicator cell can be transfected with an expression vector, incubated in the presence and in the absence of a test compound, and the effect of the compound on the expression of the molecule or on a biological response regulated by can be determined. The biological activities include activities determined in vivo, or in vitro, according to standard techniques. Activity can be a direct activity, such as an association with a target molecule or binding partner.

Alternatively, the indicator composition can be a cell-free composition that includes at least one of a Shn2 or a Shn3 protein. Alternatively, the activity is an indirect activity, such as a cellular signaling activity occurring downstream of the interaction of the protein with a target molecule or a biological effect occurring as a result of the signaling cascade triggered by that interaction. For example, biological activities of Shn2 include: modulation of bone growth, modulation of trabecular bone formation, modulation of bone mineralization, modulation of trabecular bone mineralization, modulation of trabecular bone formation in the diaphysis of a bone, modulation of trabecular bone mineralization in the diaphysis of a bone, modulation of osteoclastogenesis, modulation of osteoblast versus osteoclast activity, e.g., in bone formation and/or remodeling of bone.

In one embodiment, the invention provides methods for identifying compounds that modulate cellular responses in which Shn2 or Shn3 is involved.

In one embodiment, the ability of the compound to modulate bone formation and mineralization can be measured. For example, as described herein, animals deficient in Shn2 and Shn3 develop an osteosclerotic phenotype, e.g., an abundance of trabecular bone in the diaphysis of a long bone, with a simultaneous decrease in growth plate maturation.

Various in vitro techniques for determining the ability of compound to modulate bone formation and mineralization are known to the skilled artisan. For example, skeletal architecture can be assayed by digital radiography of, trabeculation (i.e., the anastomosing bony spicules in cancellous bone which form a meshwork of intercommunicating spaces that are filled with bone marrow) can be determined by three-dimensional μ-QCT imaging, and by analyses of bone cross-sections. In addition, trabecular number, trabecular thickness, bone volume per tissue volume (BV/TV), and bone mineral density (BMD) can also be determined by μ-QCT imaging. These analyses can be performed on whole skeleton preparations or individual bones. Mineralized bone and non-mineralized cartilage formation can be determined by histochemical analyses, such as by alizarin red/alcian blue staining. To assay a compound for an effect on osteoblast function versus osteoclast function, in vitro osteoclast differentiation assays are performed by culturing bone marrow (BM) in the presence of M-CSF and RANKL to generate TRAP+ osteoclasts. In vivo determinations of whether a compound effects osteoblast function or osteoclast can be performed by, for example, bone marrow transfers. In addition, various histomorphometric parameters can be analyzed to determine bone formation rates. For example, dual calcein-labeling of bone visualized with fluorescent micrography allows the determination of bone formation rate (BFR), which is calculated by multiplying the mineral apposition rate (MAR), which is a reflection of the bone formation capabilities of osteoblasts, by the area of mineralized surface per bone surface (MS/BS). In addition, the total osteoblast surface, which a reliable indicator of osteoblast population, can be measured, as can osteoid thickness, i.e., the thickness of bone that has not undergone calcification. Sections of bone can also be analyzed by staining with Von Kossa and Toluidine Blue for analysis of in vivo bone formation. The ex vivo culturing of osteoblast precursors and immature osteoblasts can also be performed to determine if cells possess the capacity to form mineralized nodules, which reflects the generation of extracellular matrix, i.e., the mineralized matrix of bone. Furthermore, these cultures can be assayed for their proliferative ability, e.g., by cell counting, and can be stained for the presence of various markers of bone formation, such as for example, alkaline phosphatase. These same cultures can also be used for various analyses of mRNA and protein production of numerous molecules known to be involved in bone formation and mineralization, and osteoclastogenesis, such as, for example, BSP, ColI($\alpha$)1, and OCN, ALP, LRP5, Osterix, Runx2, RANKL, RSK2, and ATF4, as well as ADAMTS4, ADM, GADD45B, IBSP, MMP25, MT2A, STC1, MEPE, TWIST1, IGFBP3, S100A4, AKT3, COL4A1, ADAM8, CCR2, CSTA, RAC2, CRYAB and CYP1B.

In one embodiment, a compound that has been identified as a Shn3 modulating compound can be tested for its ability to reduce osteoclast activity in at least one of calvariae and diaphyseal bone as described in the appended Examples.

To determine whether a test compound modulates Shn2 or Shn3 protein expression, or the expression of a protein in a signal transduction pathway involving Shn2 or Shn3 as described herein, in vitro transcriptional assays can be performed. In one example of such an assay, a regulatory sequence (e.g., the full length promoter and enhancer) of Shn2 or Shn3 can be operably linked to a reporter gene such as chloramphenicol acetyltransferase (CAT), GFP, or luciferase, e.g., OSE2-luciferase, and introduced into host cells. Other techniques are known in the art.

To determine whether a test compound modulates Shn2 or Shn3 mRNA expression, or the expression of genes modulated by Shn2 or Shn3, various methodologies can be performed, such as quantitative or real-time PCR.

"GATA3" is a Th2-specific transcription factor that is required for the development of Th2 cells. GATA-binding proteins constitute a family of transcription factors that recognize a target site conforming to the consensus WGA-TAR (W=A or T and R=A or G). The nucleotide sequence and amino acid sequence of human GATA3, is described in, for example, GenBank Accession Nos. gi:4503928, gi:50541957, and gi:4503929. The nucleotide sequence and amino acid sequence of murine GATA3, is described in, for example, GenBank Accession No. gi:40254638 and gi:6679951. The domains of GATA3 responsible for specific DNA-binding site recognition (amino acids 303 to 348) and trans activation (amino acids 30 to 74) have been identified. The signaling sequence for nuclear localization of human GATA-3 is a property conferred by sequences within and surrounding the amino finger (amino acids 249 to 311) of the protein. Exemplary genes whose transcription is regulated by GATA3 include IL-5, IL-12, IL-13, and IL-12R$\beta$2.

The peroxisome proliferator-activated receptors (PPARs) are members of the nuclear hormone receptor subfamily of transcription factors. PPARs form heterodimers with retinoid X receptors (RXRs) and these heterodimers regulate transcription of various genes. There are 3 known subtypes of PPARs, PPAR-alpha, PPAR-delta, and PPAR-gamma. There are four isoforms of human PPAR-gamma, the nucleotide and amino acid sequence of which can be found in, for example, GenBank Accession No.: 116284367, gi:116284371, 116284372, and 116284372. The nucleotide and amino acid sequence of mouse and rat PPAR-gamma are known and can be found in, for example, GenBank Accession No.: gi:187960102 and gi:6981385, respectively.

In one embodiment, the activity of Shn3 can be determined by measuring the expression level of a gene that is regulated by Shn3, e.g., RANKL.

In one embodiment, the methods of the invention comprise determining the level of expression or activity of molecules shown to be involved in the differentiation and/or activity of osteoblasts and osteoclasts (See, e.g., PCT/US2008/06783 which describes such molecules, the contents of which are expressly incorporated herein by this reference).

As used interchangeably herein, the terms "operably linked" and "operatively linked" are intended to mean that the nucleotide sequence is linked to a regulatory sequence in a manner which allows expression of the nucleotide sequence in a host cell (or by a cell extract). Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

A variety of reporter genes are known in the art and are suitable for use in the screening assays of the invention. Examples of suitable reporter genes include those which encode chloramphenicol acetyltransferase, beta-galactosidase, alkaline phosphatase, green fluorescent protein, or luciferase. Standard methods for measuring the activity of these gene products are known in the art.

A variety of cell types are suitable for use as an indicator cell in the screening assay. Preferably a cell line is used which expresses low levels of endogenous Shn2 or Shn3 and is then engineered to express recombinant protein. Cells for use in the subject assays include both eukaryotic and prokaryotic cells. For example, in one embodiment, a cell is a bacterial cell. In another embodiment, a cell is a fungal cell, such as a yeast cell. In another embodiment, a cell is a vertebrate cell, e.g., an avian cell or a mammalian cell (e.g., a murine cell, or a human cell).

In one embodiment, the level of expression of the reporter gene in the indicator cell in the presence of the test compound is higher than the level of expression of the reporter gene in the indicator cell in the absence of the test compound and the test compound is identified as a compound that stimulates the expression of Shn2 or Shn3. In another embodiment, the level of expression of the reporter gene in the indicator cell in the presence of the test compound is lower than the level of expression of the reporter gene in the indicator cell in the absence of the test compound and the test compound is identified as a compound that inhibits the expression of Shn2 or Shn3.

Furthermore, given the ability of Shn2 to interact with a SMAD1/4 and Cebpa and drive the transcription of a Pparg promoter reporter construct in response to BMP-2 (as described in Jin, supra), the ability of a compound to modulate BMP-2 signaling in MEF cells can be measured by measuring the transcriptional ability of Pprag. In one embodiment, a Pprag promoter, or a fragment thereof, e.g., nucleotides −615 to +64 of the murine pprag gene, is operably linked to a luciferase reporter gene. Similarly, the ability of Shn2 to transactivate an NF-kB reporter construct may be determined.

The ability of the test compound to modulate Shn2 binding to a substrate or target molecule (e.g., NF-kB, SMAD4, SMAD1, Cebpa, and/or PPAR-gamma) can also be determined.

In another embodiment, the ability of a compound to modulate Shn3 binding to a substrate or target molecule can be determined. For example, the ability of Shn3 to bind to CREB can be measured.

Determining the ability of the test compound to modulate Shn2 or Shn3 binding to a target molecule (e.g., a binding partner such as a substrate) can be accomplished, for example, by coupling the target molecule with a radioisotope or enzymatic label such that binding of the target molecule to Shn2 or Shn3 or a molecule in a signal transduction pathway involving Shn2 can be determined by detecting the labeled Shn2 or Shn3 target molecule in a complex. Alternatively, Shn2 or Shn3 may be coupled with a radioisotope or enzymatic label to monitor the ability of a test compound to modulate Shn2 or Shn3 binding to a target molecule in a complex. Determining the ability of the test compound to bind to Shn2 or Shn3 can be accomplished, for example, by coupling the compound with a radioisotope or enzymatic label such that binding of the compound to Shn2 or Shn3 can be determined by detecting the labeled compound in a complex. For example, targets can be labeled with $^{125}I$, $^{35}S$, $^{14}C$, or $^{3}H$, either directly or indirectly, and the radioisotope detected by direct counting of radioemmission or by scintillation counting. Alternatively, compounds can be labeled with, for example, horseradish peroxidase, alkaline phosphatase, or luciferase, and the enzymatic label detected by determination of conversion of an appropriate substrate to product.

In another embodiment, the ability of Shn2 or Shn3 to be acted on by an enzyme or to act on a substrate can be measured. For example, in one embodiment, the effect of a compound on the phosphorylation of Shn2 or Shn3 can be measured using techniques that are known in the art.

It is also within the scope of this invention to determine the ability of a compound to interact with Shn2 or Shn3 without the labeling of any of the interactants. For example, a microphysiometer can be used to detect the interaction of a compound with a Shn2 or Shn3 molecule without the labeling of either the compound or the molecule (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Using such exemplary methods, changes in this acidification rate can be used as an indicator of the interaction between a compound and Shn2 or Shn3.

Exemplary target molecules of Shn2 include: NF-kB, SMAD4, SMAD1, Cebpa, and/or PPAR-gamma. Exemplary target molecules of Shn3 include CREB.

In another embodiment, a different (i.e., non-Shn2 or Shn3) molecule acting in a pathway involving Shn2 or Shn3 that acts upstream or downstream of Shn2 or Shn3 can be included in an indicator composition for use in a screening assay. Compounds identified in a screening assay employing such a molecule would also be useful in modulating Shn2 or Shn3 activity, albeit indirectly.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell.

The cells of the invention can express endogenous Shn2 or Shn3 or another protein in a signaling pathway involving Shn2 or Shn3 or can be engineered to do so. For example, a cell that has been engineered to express the Shn2 or Shn3 protein and/or a non protein which acts upstream or downstream of can be produced by introducing into the cell an expression vector encoding the protein.

Recombinant expression vectors that can be used for expression of Shn2 or Shn3 or a molecule in a signal transduction pathway involving Shn2 or Shn3 (e.g., a protein which acts upstream or downstream of Shn2 or Shn3) are known in the art. For example, the cDNA is first introduced into a recombinant expression vector using standard molecular biology techniques. A cDNA can be obtained, for example, by amplification using the polymerase chain reaction (PCR) or by screening an appropriate cDNA library. The nucleotide sequences of cDNAs for or a molecule in a signal transduction pathway involving (e.g., human, murine and yeast) are known in the art and can be used for the design of PCR primers that allow for amplification of a cDNA by standard PCR methods or for the design of a hybridization probe that can be used to screen a cDNA library using standard hybridization methods.

Following isolation or amplification of a cDNA molecule, the DNA fragment is introduced into an expression vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule in a form suitable for expression of the nucleic acid in a host cell, which means that the recombinant expression vectors include one or more regulatory sequences, selected on the basis of the host cells to be used for expression and the level of expression desired, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell, those which direct expression of the nucleotide sequence only in certain host cells (e.g., tissue-specific regulatory sequences) or those which direct expression of the nucleotide sequence only under certain conditions (e.g., inducible regulatory sequences).

When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDM8 (Seed, B., (1987) *Nature* 329:840) and pMT2PC (Kaufman et al. (1987), *EMBO J.* 6:187-195). A variety of mammalian expression vectors carrying different regulatory sequences are commercially available. For constitutive expression of the nucleic acid in a mammalian host cell, a preferred regulatory element is the cytomegalovirus promoter/enhancer. Moreover, inducible regulatory systems for use in mammalian cells are known in the art, for example, systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Still further, many tissue-specific regulatory sequences are known in the art, including the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916) and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Vector DNA can be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on a separate vector from that encoding Shn2 or, more preferably, on the same vector. Cells stably transfected with the introduced nucleic acid can be identified by drug selection (e.g., cells that have incorporated the selectable marker gene will survive, while the other cells die).

In one embodiment, within the expression vector coding sequences are operatively linked to regulatory sequences that allow for constitutive expression of the molecule in the indicator cell (e.g., viral regulatory sequences, such as a cytomegalovirus promoter/enhancer, can be used). Use of a recombinant expression vector that allows for constitutive expression of Shn2 or Shn3 or a molecule in a signal transduction pathway involving Shn2 or Shn3 in the indicator cell is preferred for identification of compounds that enhance or inhibit the activity of the molecule. In an alternative embodiment, within the expression vector the coding sequences are operatively linked to regulatory sequences of the endogenous gene for Shn2 or Shn3 or a molecule in a signal transduction pathway involving Shn2 or Shn3 (i.e., the promoter regulatory region derived from the endogenous gene). Use of a recombinant expression vector in which expression is controlled by the endogenous regulatory sequences is preferred for identification of compounds that enhance or inhibit the transcriptional expression of the molecule.

In yet another aspect of the invention, the Shn2 or Shn3 protein or fragments thereof can be used as "bait protein" e.g., in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with Shn2 or Shn3 ("binding proteins" or "bp") and are involved in Shn2 or Shn3 activity. Such Shn2 or Shn3-binding proteins are also likely to be involved in the propagation of signals by the Shn proteins or Shn targets such as, for example, downstream elements of an Shn2 or Shn3-mediated signaling pathway. Alternatively, such Shn2 or Shn3-binding proteins can be Shn2 or Shn3 inhibitors.

The two-hybrid system is based on the modular nature of most transcription factors, which consist of separable DNA-binding and activation domains. Briefly, the assay utilizes two different DNA constructs. In one construct, the gene that codes for an Shn protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an Shn2 or Shn3 dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Shn2 or Shn3 protein or a molecule in a signal transduction pathway involving Shn2 or Shn3.

B. Cell-Free Assays

In another embodiment, the indicator composition is a cell free composition. Shn2 or Shn3 or a non-Shn2 or Shn3 protein in a signal transduction pathway involving Shn2 or Shn3 expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies can be used to produce a purified or semi-purified protein that can be used in a cell free composition. Alternatively, a lysate or an extract of cells expressing the protein of interest can be prepared for use as cell-free composition.

In one embodiment, compounds that specifically modulate Shn2 or Shn3 activity are identified based on their ability to modulate the interaction of Shn2 or Shn3 with a target molecule to which Shn2 or Shn3 binds. The target molecule can be a DNA molecule, e.g., a Shn2 or Shn3-responsive element, such as the regulatory region of a chaperone gene, or a protein molecule. Suitable assays are known in the art that allow for the detection of protein-protein interactions (e.g., immunoprecipitations, two-hybrid assays and the like) or that allow for the detection of interactions between a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of Shn2 or Shn3 with a target molecule.

In one embodiment, the amount of binding of Shn2 or Shn3 to the target molecule in the presence of the test compound is greater than the amount of binding of Shn2 or Shn3 to the target molecule in the absence of the test compound, in which case the test compound is identified as a compound that enhances binding of Shn2 or Shn3 to a target. In another embodiment, the amount of binding of the Shn2 or Shn3 to the target molecule in the presence of the test compound is less than the amount of binding of the Shn2 or Shn3 to the target molecule in the absence of the test compound, in which case the test compound is identified as a compound that inhibits binding of Shn2 or Shn3 to the target. Binding of the test compound to Shn2 or Shn3 or a molecule in a signal transduction pathway involving Shn2 or Shn3 can be determined either directly or indirectly as described above. Determining the ability of Shn2 or Shn3 protein to bind to a test compound can also be accomplished using a technology such as real-time Biomolecular Interaction Analysis (BIA) (Sjolander, S. and Urbaniczky, C. (1991) Anal. Chem. 63:2338-2345; Szabo et al. (1995) Curr. Opin. Struct. Biol. 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In the methods of the invention for identifying test compounds that modulate an interaction between Shn2 or Shn3 protein and a target molecule, a polypeptide comprising the complete Shn2 or Shn3 amino acid sequence can be used in the method, or, alternatively, a polypeptide comprising only portions of the protein can be used. For example, an isolated Shn2 or Shn3 interacting domain can be used. An assay can be used to identify test compounds that either stimulate or inhibit the interaction between the Shn2 or Shn3 protein and a target molecule. A test compound that stimulates the interaction between the protein and a target molecule is identified based upon its ability to increase the degree of interaction between, e.g., Shn2 or Shn3 and a target molecule as compared to the degree of interaction in the absence of the test compound and such a compound would be expected to increase the activity of Shn2 or Shn3 in the cell. A test compound that inhibits the interaction between the protein and a target molecule is identified based upon its ability to decrease the degree of interaction between the protein and a target molecule as compared to the degree of interaction in the absence of the compound and such a compound would be expected to decrease Shn2 or Shn3 activity.

In one embodiment of the above assay methods of the present invention, it may be desirable to immobilize either Shn2 or Shn3 or a respective target molecule, for example, to facilitate separation of complexed from uncomplexed forms of one or both of the proteins, or to accommodate automation of the assay. Binding of a test compound to a Shn2 or Shn3, or interaction of a Shn2 or Shn3 protein with a target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided in which a domain that allows one or both of the proteins to be bound to a matrix is added to one or more of the molecules. For example, glutathione-S-transferase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or Shn2 or Shn3 protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either a Shn2 or Shn3 protein, or a target molecule can be immobilized utilizing conjugation of biotin and streptavidin. Biotinylated protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with protein or target molecules but which do not interfere with binding of the protein to its target molecule can be derivatized to the wells of the plate, and unbound target or Shn protein is trapped in the wells by antibody conjugation. Methods for detecting such complexes, in addition to those described above for the GST-immobilized complexes, include immunodetection of complexes using antibodies reactive with Shn2 or Shn3 or target molecule, as well as enzyme-linked assays which rely on detecting an enzymatic activity associated with the Shn2 or Shn3 protein or target molecule.

C. Assays Using Knock-Out Cells

In another embodiment, the invention provides methods for identifying compounds that modulate skeletal remodeling and/or patterning using cells deficient in Shn2, Shn3 or deficient in Shn2 and Shn3. As described in the Examples, inhibition of Shn2 activity and Shn3 activity (e.g., by disruption of the Shn2 and Shn3 gene) in cells results, e.g., in increased trabecular bone formation and mineralization in the diaphysis of a bone. Thus, cells deficient in Shn2 (or a molecule in a signal transduction pathway involving Shn2) or Shn2 and Shn3 can be used identify agents that modulate skeletal remodeling and patterning by means other than modulating Shn2 or Shn2 and Shn3 itself (i.e., compounds that "rescue" the deficient phenotype). In addition, mice deficient in Shn3 exhibit qualitative reductions in osteoclasts in calvariae and diaphyseal bone, but not in metaphyseal regions. Thus, cells deficient in Shn3 (or a molecule in a signal transduction pathway involving Shn3) can be used to identify agents that modulate osteoclast activity in calvariae and diaphyseal bone. Alternatively, a "conditional knockout" system, in which the gene is rendered non-functional in a conditional manner, can be used to create deficient cells for use in screening assays. For example, a tetracycline-regulated system for conditional disruption of a gene as described in WO 94/29442 and U.S. Pat. No. 5,650,298 can be used to create cells, or animals from which cells can be isolated, be rendered deficient in Shn2 (and/or Shn3) in a controlled manner through modulation of the tetracycline concentration in contact with the cells. Specific cell types, e.g., lymphoid cells (e.g., thymic, splenic and/or lymph node cells) or purified cells such as T cells, B cells, osteoblasts, osteoclasts, from such animals can be used in screening assays.

In the screening method, cells deficient in Shn2 and/or Shn3 can be contacted with a test compound and skeletal remodeling or patterning can be monitored. Modulation of the response in cells deficient in Shn2, Shn3, or Shn2 and Shn3 (as compared to an appropriate control such as, for example, untreated cells or cells treated with a control agent) identifies a test compound as a modulator of the readout.

In one embodiment, the test compound is administered directly to a non-human knock out animal, preferably a mouse (e.g., a mouse in which the Shn2, Shn3, or Shn2 and Shn3 gene is conditionally disrupted by means described above, or a chimeric mouse deficient in Shn2, Shn3, or Shn2 and Shn3 as described above), to identify a test compound that modulates the in vivo responses of cells deficient in Shn2 or Shn2 and Shn3. In another embodiment, cells deficient in Shn2, Shn3, or Shn2 and Shn3 are isolated from the non-human deficient animal and contacted with the test compound ex vivo to identify a test compound that modulates a response regulated by Shn2 or Shn3 in the cells Cells deficient in Shn2, Shn3, or Shn2 and Shn3 can be obtained from a non-human animals created to be deficient in one or more of these genes. Preferred non-human animals include monkeys, dogs, cats, mice, rats, cows, horses, goats and sheep. In preferred embodiments, the deficient animal is a mouse. Mice deficient in Shn2, Shn3, or Shn2 and Shn3 can be made using methods known in the art. One example of such a method and the resulting Shn2, Shn3, or Shn2 and Shn3 heterozygous and homozygous animals is described in the appended examples. Non-human animals deficient in a particular gene product typically are created by homologous recombination. In an exemplary embodiment, a vector is prepared which contains at least a portion of the gene into which a deletion, addition or substitution has been introduced to thereby alter, e.g., functionally disrupt, the endogenous Shn2, Shn3, or Shn2 and Shn3. The gene preferably is a mouse gene. For example, a mouse Shn gene can be isolated from a mouse genomic DNA library using the mouse Shn2 cDNA as a probe. The mouse Shn gene then can be used to construct a homologous recombination vector suitable for modulating an endogenous Shn gene in the mouse genome. In a preferred embodiment, the vector is designed such that, upon homologous recombination, the endogenous gene is functionally disrupted (i.e., no longer encodes a functional protein; also referred to as a "knock out" vector).

Alternatively, the vector can be designed such that, upon homologous recombination, the endogenous gene is mutated or otherwise altered but still encodes functional protein (e.g., the upstream regulatory region can be altered to thereby alter the expression of the endogenous Shn protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced gene has homologously recombined with the endogenous gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al. In one embodiment, Shn2 and Shn3 null mice are made by breeding single knock out animals.

In one embodiment of the screening assay, compounds are contacted with deficient cells by administering the test compound to a non-human deficient animal in vivo and evaluating the effect of the test compound on the response in the animal.

The test compound can be administered to a non-knock out animal as a pharmaceutical composition. Such compositions typically comprise the test compound and a pharmaceutically acceptable carrier. As used herein the term "pharmaceutically acceptable carrier" includes any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Except insofar as any conventional media or compound is incompatible with the active compound, use thereof in the compositions is contemplated. Supplementary active compounds can also be incorporated into the compositions. Pharmaceutical compositions are described in more detail below.

In another embodiment, compounds that modulate a biological response regulated by Shn2 or Shn3, are identified by contacting cells deficient in Shn2 and/or Shn3 ex vivo with one or more test compounds, and determining the effect of the test compound on a read-out. In one embodiment, Shn2 (and/or Shn3) deficient cells contacted with a test compound ex vivo can be readministered to a subject.

For practicing the screening method ex vivo, cells deficient, e.g., in Shn2, Shn3, can be isolated from a non-human deficient animal or embryo by standard methods and incubated (i.e., cultured) in vitro with a test compound. Cells (e.g., T cells, B cells, osteoclasts, and/or osteoblasts) can be isolated from deficient animals by standard techniques.

Following contact of the deficient cells with a test compound (either ex vivo or in vivo), the effect of the test compound on the biological response regulated by Shn2, Shn3, or Shn2 and Shn3 can be determined by any one of a variety of suitable methods, such as those set forth herein.

D. Test Compounds

A variety of test compounds can be evaluated using the screening assays described herein. The term "test compound" includes any reagent or test agent which is employed in the assays of the invention and assayed for its ability to influence the expression and/or activity of Shn2 or Shn3. More than one compound, e.g., a plurality of compounds, can be tested at the same time for their ability to modulate the expression and/or activity of, e.g., Shn2 or Shn3 in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening can be used to assay for the activity of a compound.

In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909), peptoids (Zuckermann. (1994). *J. Med. Chem.* 37:2678), oligocarbamates (Cho et al. (1993). *Science.* 261:1303-), and hydantoins (DeWitt et al. supra). An approach for the synthesis of molecular libraries of small organic molecules with a diversity of 104-105 has been described (Carell et al. (1994). *Angew. Chem. Int. Ed. Engl.* 33:2059-; Carell et al. (1994) *Angew. Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422-; Horwell et al. (1996) *Immunopharmacology* 33:68-; and in Gallop et al. (1994); *J. Med. Chem.* 37:1233-.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms of Shn2 (e.g., dominant negative mutant forms of the molecule).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. patent '409), plasmids (Cull et al.

(1992) *Proc Natl Acad Sci USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222: 301-310; Ladner supra.).

Computer-based analysis of a protein with a known structure can also be used to identify molecules which will bind to the protein. Such methods rank molecules based on their shape complementary to a receptor site. For example, using a 3-D database, a program such as DOCK can be used to identify molecules which will bind to Shn2 or a molecule in a signal transduction pathway involving Shn2. See DesJarlias et al. (1988) *J. Med. Chem.* 31:722; Meng et al. (1992) *J. Computer Chem.* 13:505; Meng et al. (1993) *Proteins* 17:266; Shoichet et al. (1993) Science 259:1445. In addition, the electronic complementarity of a molecule to a targeted protein can also be analyzed to identify molecules which bind to the target. This can be determined using, for example, a molecular mechanics force field as described in Meng et al. (1992) *J. Computer Chem.* 13:505 and Meng et al. (1993) *Proteins* 17:266. Other programs which can be used include CLIX which uses a GRID force field in docking of putative ligands. See Lawrence et al. (1992) *Proteins* 12:31; Goodford et al. (1985) *J. Med. Chem.* 28:849; Boobbyer et al. (1989) *J. Med. Chem.* 32:1083.

Compounds identified in the subject screening assays can be used in methods of modulating one or more of the biological responses regulated by Shn2. It will be understood that it may be desirable to formulate such compound(s) as pharmaceutical compositions (described supra) prior to contacting them with cells.

Once a test compound is identified that directly or indirectly modulates, e.g., Shn2 expression or activity, by one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

The instant invention also pertains to compounds identified in the subject screening assays.

Methods for Modulating Biological Responses Regulated by Shn2 or Shn3

The present invention provides for both prophylactic and therapeutic methods of treating a subject at risk of (or susceptible to) a disorder or having a disorder associated with aberrant Shn2 or Shn3 expression and/or activity. For example, a disease, disorder, condition or injury that would benefit from increased or decreased bone formation and mineralization, as described herein.

Subjects at risk for such disorders can be identified by, for example, any or a combination of diagnostic or prognostic assays known in the art. Administration of a prophylactic agent can occur prior to the manifestation of symptoms, such that a disease, disorder, condition, or injury is prevented or, alternatively, delayed in its progression. Depending on the type of aberrancy, for example, a Shn2 or Shn3 antagonist or agonist agent can be used for treating a subject. The appropriate agent can be determined based on screening assays described herein.

Another aspect of the invention pertains to methods of modulating Shn2 or Shn3 activity for therapeutic purposes. Shn2 activity can be modulated in order to modulate trabecular bone formation and mineralization in the diaphysis of a bone. Shn2 inhibits trabecular bone formation and mineralization in the diaphysis of a bone, therefore decreasing Shn2 expression and/or biological activity results in increasing trabecular bone formation and mineralization in the diaphysis of a bone. Conversely, increasing Shn2 expression and/or biological activity would result in decreased trabecular bone formation and mineralization in the diaphysis of a bone.

In another embodiment, Shn3 activity can be modulated in order to modulate osteoclast numbers and/or activity in calvariae and diaphyseal bone. For example, decreasing Shn3 expression and/or biological activity would result in decreased osteoclast activity in these regions, but not in metaphyseal regions.

Modulatory methods of the invention involve contacting a cell (e.g., an osteoblast, e.g., a mature osteoblast) with an agent that modulates the expression and/or biological activity of Shn2 or Shn3. An agent that modulates Shn2 or Shn3 activity can be an agent as described herein, such as a Shn2 peptide, a nucleic acid molecule encoding one of the aforementioned peptides, a Shn2 agonist or antagonist, a peptidomimetic of a Shn2 agonist or antagonist, a Shn2 peptidomimetic, or other small molecule identified using the screening methods described herein. Additional agents include, but are not limited to a nucleic acid molecule that is antisense to a Shn3 molecule, a Shn3 siRNA molecule, a dominant negative Shn3 molecule, a nucleic acid molecule encoding a Shn3 polypeptide, a Shn3 polypeptide, or combinations thereof.

These modulatory methods can be performed in vitro (e.g., by contacting the cell with the agent) or, alternatively, in vivo (e.g., by administering the agent to a subject). Furthermore, the modulatory methods of the invention can be performed on a surface, in vitro or in vivo. For example, the surface of a surgically implanted, rod, pin, plate, screw, or other implement implanted for the purpose of stabilizing, repairing a bone, e.g., a fracture, a joint, a tooth, or a joint replacement, or a tooth replacement, may be treated with an agent of the invention such that bone formation and mineralization is modulated, e.g., enhanced or increased. As such, the present invention provides methods of treating an individual afflicted with a disease, condition, disorder or injury that would benefit from up- or down-modulation of a Shn2 or Shn3 polypeptide, e.g., a disorder in which modulation of trabecular bone formation and mineralization in the diaphysis of a bone would be beneficial. In one embodiment, the method involves administering an agent (e.g., an agent identified by a screening assay described herein), or combination of agents that modulates (e.g., upregulates or downregulates) Shn2 or Shn3 expression or biological activity, as described herein.

Inhibition of Shn2 or Shn3 activity is desirable in situations in which Shn2 or Shn3 is abnormally upregulated and/or in which decreased Shn2 or Shn3 activity is likely to have a beneficial effect, for example in a situation when increased trabecular bone formation and mineralization in the diaphysis of a bone is desirable. Such situations include conditions, disorders, diseases, or injuries include but are not limited to, for example, osteoporosis, osteomalacia, skeletal changes of hyperparathyroidism and chronic renal failure (renal osteodystrophy) and osteitis deformans (Paget's disease of bone), osteopenia, osteoarthritis and inflammatory arthritides characterized by bone loss or excess bone formation including for example rheumatoid arthritis, ankylosing spondylitis, psoriatic arthritis.

Exemplary agents for use in upmodulating Shn2 (i.e., agonists) include, e.g., nucleic acid molecules encoding Shn2 and/or Shn3, Shn2 and/or Shn3 polypeptides, Shn2 and/or Shn3 peptides, and compounds that stimulate the interaction of Shn2 with Smad1, Smad4, Cebpa, PPAR-gamma, for example (e.g., compounds identified in the subject screening assays).

Exemplary agents for use in downmodulating Shn2 or Shn3 (i.e., antagonists) include agents that inhibit the activity of Shn2 or Shn3 in cell, for example, nucleic acid molecules that are antisense to a Shn2 and/or Shn3 molecule, a Shn2 and/or Shn3 siRNA molecule, a dominant negative Shn2 and/or Shn3 molecule, or combinations thereof (e.g., compounds identified in the subject screening assays).

A. Downregulation of Shn2 Biological Activities

There are numerous embodiments of the invention for downregulating the function of a Shn2 or Shn3 polypeptide to thereby upregulate or promote bone formation and mineralization. Downregulating the function of Shn2 or Shn3 can be in the form of promoting or increasing bone formation and mineralization prior to development of a condition or injury (e.g., in a subject diagnosed as likely to develop a condition that would benefit from increased trabecular bone formation and mineralization in the diaphysis of a bone, such as for example, a premenopausal woman) or may involve promoting the induction of trabecular bone formation and mineralization in the diaphysis of a bone to treat, for example, a bone fracture or break, a tooth replacement, either replacement of a subjects' own tooth or a prosthetic tooth, or ameliorate symptoms of an ongoing condition, such as for example, bone loss associated with, for example peri-menopause or menopause. The functions of osteoblasts can be modulated accordingly by upregulating trabecular bone formation and mineralization in the diaphysis of a bone.

For example, Shn2 or Shn3 activity can be inhibited by contacting a cell which expresses Shn2 or Shn3 with an agent that inhibits the expression or activity of Shn2 or Shn3. Such an agent can be a compound identified by the screening assays described herein. In another embodiment, the agent is a peptide.

In one aspect of the invention, agents that inhibit a Shn2 or Shn3 activity can be identified by their ability to increase trabecular bone formation and mineralization in the diaphysis of a bone. A number of art-recognized in vitro and in vivo assays of trabecular bone formation and mineralization in the diaphysis of a bone can be employed to measure, e.g., osteoblast and osteoclast function using assays known in the art and described in more detail herein.

In another embodiment, trabecular bone formation and mineralization in the diaphysis of a bone can be increased in a subject by removing osteoblasts, e.g., mature osteoblasts, from the patient, contacting the osteoblasts in vitro with an agent (e.g., a small molecule) that downregulates Shn2 or Shn3 activity, and reintroducing the in vitro-treated osteoblasts into the patient.

Increasing trabecular bone formation and mineralization in the diaphysis of a bone by inhibiting Shn2 or Shn3 activity is useful in situations in which increased trabecular bone formation and mineralization in the diaphysis of a bone would be beneficial. For example, osteoporosis, including idiopathic osteoporosis, secondary osteoporosis, transient osteoporosis of the hip, osteomalacia, Paget's disease of bone, and osteopenia in which there is progressive loss of bone density and thinning of bone tissue are conditions which would benefit from increased trabecular bone formation and mineralization in the diaphysis of a bone such that breaks and/or fractures would not occur. Osteoporosis and osteopenia can result not only from aging and reproductive status, but can also be secondary to numerous diseases and disorders, as well as due to prolonged use of numerous medications, e.g., anticonvulsants (e.g., for epilepsy), corticosteroids (e.g., for rheumatoid arthritis and asthma), and/or immunosuppressive agents (e.g., for cancer). For example, glucocorticoid-induced osteoporosis is a form of osteoporosis that is caused by taking glucocorticoid medications such as prednisone (Deltasone, Orasone, etc.), prednisolone (Prelone), dexamethasone (Decadron, Hexadrol), and cortisone (Cortone Acetate). These medications are frequently used to help control many rheumatic diseases, including rheumatoid arthritis, systemic lupus erythematosus, inflammatory bowel disease, and polymyalgia rheumatica. Other diseases in which osteoporosis may be secondary include, but are not limited to, juvenile rheumatoid arthritis, diabetes, osteogenesis imperfecta, hyperthyroidism, hyperparathyroidism, Cushing's syndrome, malabsorption syndromes, anorexia nervosa and/or kidney disease. In addition, numerous behaviors have been associated with osteoporosis, such as, prolonged inactivity or immobility, inadequate nutrition (especially calcium, vitamin D), excessive exercise leading to amenorrhea (absence of periods), smoking, and/or alcohol abuse.

The administration of a molecule which inhibits the activity of Shn2 or Shn3, e.g., by blocking the interaction of Shn2 with, for example, NF-kB, Smad1, Smad4, Cebpa, PPAR-gamma, in osteoblasts, e.g., mature osteoblasts (such as a Shn2 and/or Shn3 peptide or a small molecule) or the interaction of Shn3 with CREB alone or in conjunction with another downmodulatory agent can increase bone formation and mineralization.

Other modulatory methods and/or agents that can be used in connection with the downmodulatory methods of the invention to increase bone formation and mineralization, include for example, surgery, OP-1$^R$, also known as BMP-7, a member of the Bone Morphogenetic Protein superfamily, BMP-2, vitamin D, calcium, hormone replacement therapy, bisphosphonates, e.g., analogues of endogenous pyrophosphates which inhibit bone resorption, such as, for example, alendronate, etidronate, pamidronate, Calcitonin, Clodronate, selective estrogen receptor modulators (SERMs), e.g., raloxifene, parathyroid hormone, e.g., teriparatide, fluoride, strontium ranelate, TNF-alpha antibodies, osteoprotegerin, beta-Cryptoxanthin, and thiazides can decrease urinary calcium excretion and slow bone loss, tyrosine phosphatase inhibitors, e.g., sodium orthovanadate, alfacalcidol, menatetrenone, statins, e.g., simvastatin.

Exemplary Inhibitory Compounds

Since inhibition of Shn2 or Shn3 activity is associated with increased bone formation and mineralization, to increase bone formation and mineralization (e.g., osteoblasts or osteoclasts) are contacted with an agent that inhibits Shn2 or Shn3 activity. The cells may be contacted with the agent in vitro and then the cells can be administered to a subject or, alternatively, the agent may be administered to the subject (e.g., directly to an articular site at which bone growth and/or differentiation is desired). The methods of the invention using Shn2 or Shn3 inhibitory compounds can be used in the treatment of disorders in which increased bone formation and mineralization is beneficial.

Inhibitory compounds of the invention can be, for example, intracellular binding molecules that act to specifically inhibit the expression or activity of Shn2 or Shn3. As used herein, the term "intracellular binding molecule" is intended to include molecules that act intracellularly to inhibit the expression or activity of a protein by binding to the protein or to a nucleic acid (e.g., an mRNA molecule) that encodes the protein. Examples of intracellular binding molecules, described in further detail below, include antisense nucleic acids, siRNA molecules, intracellular antibodies, peptidic compounds that inhibit the interaction of Shn2 with a target molecule (e.g., Smad1, Smad4, Cebpa, PPAR-gamma), agents that inhibit the interaction of Shn3 with a target molecule, e.g., CREB, and chemical agents that specifically inhibit Shn2 or Shn3 activity.

i. Antisense or siRNA Nucleic Acid Molecules

In one embodiment, an inhibitory compound of the invention is an antisense nucleic acid molecule that is complementary to a gene encoding Shn2, a gene encoding Shn3, or a molecule in a signal transduction pathway involving Shn2, or to a portion of said genes, or a recombinant expression vector encoding said antisense nucleic acid molecules. For simplicity, the below-mentioned exemplary antisense and siRNA molecules will refer to Shn2 or Shn3 antisense and siRNA molecules. However, it is understood that exemplary antisense and siRNA molecules of the above-mentioned molecules, e.g., a molecule in a signal transduction pathway involving Shn2 or Shn3, or a portion of said genes, are also included in the invention. The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986; Askari, F. K. and McDonnell, W. M. (1996) N. Eng. J. Med. 334:316-318; Bennett, M. R. and Schwartz, S. M. (1995) Circulation 92:1981-1993; Mercola, D. and Cohen, J. S. (1995) Cancer Gene Ther. 2:47-59; Rossi, J. J. (1995) Br. Med. Bull. 51:217-225; Wagner, R. W. (1994) Nature 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the coding strand sequences encoding Shn2 or Shn3, antisense nucleic acids of the invention can be designed according to the rules of Watson and Crick base pairing. The antisense nucleic acid molecule can be complementary to the entire coding region of Shn2 or Shn3 mRNA, but more preferably is an oligonucleotide which is antisense to only a portion of the coding or noncoding region of Shn2 or Shn3 mRNA. For example, the antisense oligonucleotide can be complementary to the region surrounding the translation start site of Shn2 or Shn3 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. To inhibit expression in cells, one or more antisense oligonucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a Shn2 or Shn3 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215: 327-330). In another embodiment, an antisense nucleic acid of the invention is a compound that mediates RNAi. RNA interfering agents include, but are not limited to, nucleic acid molecules including RNA molecules which are homologous to the target gene or genomic sequence, e.g., Shn2, Shn3, or a fragment thereof, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs and Ambion. In one embodiment one or more of the chemistries described above for use in antisense RNA can be employed.

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, *Nature* 334:585-591)) can be used to catalytically cleave Shn2 mRNA transcripts to thereby inhibit translation of Shn2 mRNA. A ribozyme having specificity for a Shn2 or Shn3-encoding nucleic acid can be designed based upon the nucleotide sequence of Shn2 or Shn3. For example, a derivative of a *Tetrahymena* L-19 IVS RNA can be constructed in which the nucleotide sequence of the active site is complementary to the nucleotide sequence to be cleaved in a Shn2-encoding mRNA. See, e.g., Cech et al. U.S. Pat. No. 4,987,071; and Cech et al. U.S. Pat. No. 5,116,742. Alternatively, Shn2 or Shn3 mRNA can be used to select a catalytic RNA having a specific ribonuclease activity from a pool of RNA molecules. See, e.g., Bartel, D. and Szostak, J. W., 1993, *Science* 261:1411-1418.

Alternatively, gene expression can be inhibited by targeting nucleotide sequences complementary to the regulatory region of Shn2 or Shn3 (e.g., the Shn2 or Shn3 promoter and/or enhancers) to form triple helical structures that prevent transcription of the Shn gene in target cells. See generally, Helene, C., 1991, *Anticancer Drug Des.* 6(6):569-84; Helene, C. et al., 1992, *Ann. N.Y. Acad. Sci.* 660:27-36; and Maher, L. J., 1992, *Bioassays* 14(12):807-15.

In yet another embodiment, the Shn2 or Shn3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., 1996, *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al., 1996, supra; Perry-O'Keefe et al., 1996, *Proc. Natl. Acad. Sci. USA* 93: 14670-675.

PNAs of Shn nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of Shn nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B., 1996, supra)); or as probes or primers for DNA sequencing or hybridization (Hyrup B. et al., 1996, supra; Perry-O'Keefe supra).

In another embodiment, PNAs of Shn2 or Shn3 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of Shn2 or Shn3 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B., 1996, supra). The synthesis of PNA-DNA chimeras can be performed as described in Hyrup B., 1996, supra and Finn P. J. et al., 1996, *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al., 1989, *Nucleic Acid Res.* 17: 5973-88). PNA monomers are then coupled in a stepwise manner to produce a chimeric molecule with a 5' PNA segment and a 3' DNA segment (Finn P. J. et al., 1996, supra). Alternatively, chimeric molecules can be synthesized with a 5' DNA segment and a 3' PNA segment (Peterser, K. H. et al., 1975, *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. US.* 86:6553-6556; Lemaitre et al., 1987, *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., 1988, *Bio-Techniques* 6:958-976) or intercalating agents. (See, e.g., Zon, 1988, *Pharm. Res.* 5:539-549). To this end, the oligonucleotide may be conjugated to another molecule, (e.g., a peptide, hybridization triggered cross-linking agent, transport agent, or hybridization-triggered cleavage agent).

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

In another embodiment, a compound that promotes RNAi can be used to inhibit expression of Shn2 or Shn3. RNA interference (RNAi is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000); Tuschl, T. et al. Genes Dev. 13, 3191-3197 (1999); Cottrell T R, and Doering T L. (2003) Trends Microbiol. 11:37-43; Bushman F. (2003) Mol. Therapy. 7:9-10; McManus M T and Sharp P A. (2002) Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described above for use in antisense RNA can be employed in molecules that mediate RNAi. Non-limiting exemplary siRNA molecules of the invention are listed below.

Exemplary siRNA molecules specific for human Shn2 are shown below:

```
Beginning at position 987:
Sense strand siRNA: GCAAUAUCCACCGCAUCGUtt

Antisense strand siRNA: ACGAUGCGGUGGAUAUUGCtt:

Beginning at position: 6079
Sense strand siRNA: GGAGGGUACAAAUCGAAUGtt

Antisense strand siRNA: CAUUCGAUUUGUACCCUCCtt

Beginning at position: 8917
Sense strand siRNA: GUAUUUGGUCUUAUGUGAAtt

Antisense strand siRNA: UUCACAUAAGACCAAAUACtt
```

Exemplary siRNA molecules specific for human Shn3 are shown below:

```
Beginning at position 1576:
Sense strand siRNA: GACCAAGAGUAAUCUCUACtt

Antisense strand siRNA: GUAGAGAUUACUCUUGGUCtt

Beginning at position 3310:
Sense strand siRNA: AUCUGAUUCUCUCGAGCAGtt

Antisense strand siRNA: CUGCUCGAGAGAAUCAGAUtt

Beginning at position 5725:
Sense strand siRNA: GCCAAAUCACAUCCAGCAUtt

Antisense strand siRNA: AUGCUGGAUGUGAUUUGGCtt
```

Other exemplary siRNA molecules specific for Shn3 include:

```
Sense strand siRNA: UAAUUCAUGAAGAAGGGGCtt

Antisense strand siRNA: GCCCCUUCUUCAUGAAUUAtt

Sense strand siRNA: UUCAUGAAGAAGGGGCUGGtt

Antisense strand siRNA: CCAGCCCCUUCUUCAUGAAtt

Sense strand siRNA: GAAGGGGCUGGAUCCGUGGtt

Antisense strand siRNA: CCACGGAUCCAGCCCCUUCtt
``` ii. Intracellular Antibodies

Another type of inhibitory compound that can be used to inhibit the expression and/or activity of Shn2 or Shn3 protein in a cell is an intracellular antibody specific for Shn2 interacting polypeptides discussed herein. As stated above, for simplicity, the below-mentioned exemplary intracellular antibodies will refer to Shn2 intracellular antibodies. However, it is understood that exemplary intracellular antibodies of the above-mentioned molecules, e.g., Shn3, a molecule in a signal transduction pathway involving Shn2, or a portion of said genes, are also included in the invention. The use of intracellular antibodies to inhibit protein function in a cell is known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Letters* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Bio/Technology* 12:396-399; Chen, S-Y. et al. (1994) *Human Gene Therapy* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of transcription factor activity according to the inhibitory methods of the invention, preferably an intracellular antibody that specifically binds the transcription factor is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g., Biocca, S. et al. (1990) *EMBO J.* 9:101-108; Mhashilkar, A. M. et al. (1995) *EMBO J.* 14:1542-1551). A preferred nuclear localization signal to be used for nuclear targeting of the intracellular antibody chains is the nuclear localization signal of SV40 Large T antigen (see Biocca, S. et al. (1990) *EMBO J.* 9:101-108; Mhashilkar, A. M. et al. (1995) *EMBO J.* 14:1542-1551).

To prepare an intracellular antibody expression vector, antibody light and heavy chain cDNAs encoding antibody chains specific for the target protein of interest, e.g., Shn2 protein, is isolated, typically from a hybridoma that secretes a monoclonal antibody specific for Shn2 protein. Preparation of antisera against Shn2 protein has been described in the art (see e.g., Rao et al, U.S. Pat. No. 5,656,452). Anti-Shn2 protein antibodies can be prepared by immunizing a suitable subject, (e.g., rabbit, goat, mouse or other mammal) with a Shn2 protein immunogen. An appropriate immunogenic preparation can contain, for example, recombinantly expressed Shn2 protein or a chemically synthesized Shn2 peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J. Immunol.* 127:539-46; Brown et al. (1980) *J Biol Chem* 255:4980-83; Yeh et al. (1976) *PNAS* 76:2927-31; and Yeh et al. (1982) *Int. J. Cancer* 29:269-75). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes) from a mammal immunized with a Shn2 protein immunogen as described above, and the culture supernatants of the resulting hybridoma cells are screened to identify a hybridoma producing a monoclonal antibody that binds specifically to the Shn2 protein. Any of the many well known protocols used for fusing lymphocytes and immortalized cell lines can be applied for the purpose of generating an anti-Shn2 protein monoclonal antibody (see, e.g., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the maf protein are identified by screening the hybridoma culture supernatants for such antibodies, e.g., using a standard ELISA assay.

Alternative to preparing monoclonal antibody-secreting hybridomas, a monoclonal antibody that binds to a Shn2 can be identified and isolated by screening a recombinant combinatorial immunoglobulin library (e.g., an antibody phage display library) with the protein, or a peptide thereof, to thereby isolate immunoglobulin library members that bind specifically to the protein. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and compounds particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; and McCafferty et al. *Nature* (1990) 348: 552-554.

Once a monoclonal antibody of interest specific for Shn2 has been identified (e.g., either a hybridoma-derived monoclonal antibody or a recombinant antibody from a combinatorial library, including monoclonal antibodies to Shn2 that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g., from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., (Gly$_4$Ser)$_3$) and expressed as a single chain molecule. To inhibit transcription factor activity in a cell, the expression vector encoding the Shn2-specific intracellular antibody is introduced into the cell by standard transfection methods as described hereinbefore.

iii. Shn2 and Shn3-Derived Peptidic Compounds

In another embodiment, an inhibitory compound of the invention is a peptidic compound derived from the Shn2 or Shn3 amino acid sequence. As stated above, for simplicity, the below-mentioned exemplary peptidic compounds will refer to peptidic compound derived from the Shn2 amino acid sequence. However, it is understood that exemplary peptidic compounds of the above-mentioned molecules, e.g., Shn2, Shn3, or a molecule in a signal transduction pathway involving Shn2, or a portion of said genes, are also included in the invention. In particular, the inhibitory compound comprises a portion of Shn2 (or a mimetic thereof) that mediates interaction of Shn2 with a target molecule such that contact of Shn2 with this peptidic compound competitively inhibits the interaction of Shn2 with the target molecule. In an exemplary embodiment, the peptide compound is designed based on the region of Shn2 that mediates interaction of Shn2 with, for example, NF-kB, Smad1, Smad4, Cebpa, PPAR-gamma.

The peptidic compounds of the invention can be made intracellularly in osteoblasts and/or immune cells by introducing into the cells an expression vector encoding the peptide. Such expression vectors can be made by standard techniques, using, for example, oligonucleotides that encode the amino acid sequences of Shn2. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

Other inhibitory agents that can be used to specifically inhibit the activity of an Shn2 protein are chemical compounds that directly inhibit Shn2 activity or inhibit the interaction between Shn2 and target molecules. Such compounds can be identified using screening assays that select for such compounds, as described in detail above.

B. Upregulation of Shn2 or Shn3 Biological Activities

Stimulation of Shn2 or Shn3 activity as a means of downmodulating bone formation and mineralization is also useful in therapy. For example, decreasing or inhibiting bone formation and mineralization by enhancing Shn2 or Shn3 is beneficial in diseases, disorders, conditions or injuries in which there is premature fusing of two or more bones, or bone density is too high, such as for example, craniosynostosis (synostosis), osteopetrosis (including malignant infantile form, intermediate form, and adult form), primary extraskeletal bone formation, e.g., multiple miliary osteoma cutis of the face, and osteitis condensans.

Alternatively, bone formation and mineralization decreased in a patient by removing cells from the patient, contacting cells in vitro with an agent (e.g., a small molecule) that enhances Shn2 or Shn3 activity, and reintroducing the in vitro-stimulated cells into the patient. In another embodiment, a method of enhancing immune responses or decreasing bone formation and mineralization involves isolating cells from a patient, transfecting them with a nucleic acid molecule encoding a Shn2 molecule and reintroducing the transfected cells into the patient.

In an additional embodiment, in performing any of the methods described herein, it is within the scope of the invention to inhibit bone formation and mineralization by administering one or more additional agents.

In another embodiment, a method of decreasing bone formation and mineralization involves transfecting them with a nucleic acid molecule encoding a Shn2 molecule with a mutation or a peptide that enhances, for example, Shn2-PPAR-gamma interaction, such that the cells express the Shn2 molecule (e.g., in the cell membrane) or the peptide (e.g., in the cytoplasm), and reintroducing the transfected cells into the patient. The ability of the transfected cells to be activated can thus be increased.

In an additional embodiment, in performing any of the methods described herein, it is within the scope of the invention to downregulate bone formation and mineralization by administering one or more additional agents. For example, surgical repair, surgical implantation of biodegradable devices, rosiglitazone, RANKL, tretinoin, enoxaparin can be used in conjunction with an agent that enhances Shn2 or Shn3 activity.

i. Exemplary Stimulatory Compounds

Since upregulation of Shn2 or Shn3 activity is associated with decreased bone formation and mineralization, a compound that specifically stimulates Shn2 activity and/or expression can be used to inhibit bone formation and mineralization. An agent that stimulates Shn3 activity can be used to increase osteoclast function in calvariae and diaphyseal bone. In the stimulatory methods of the invention, a subject is treated with a stimulatory compound that stimulates expression and/or activity of a Shn2 or Shn3 molecule. The methods of the invention using Shn2 or Shn3 stimulatory compounds can be used in the treatment of disorders in which the enhancement of bone formation and mineralization is desirable.

Examples of stimulatory compounds include active Shn2 or Shn3 protein or a molecule in a signal transduction pathway involving Shn2 or Shn3, expression vectors encoding Shn2 or Shn3 and chemical agents that specifically stimulate Shn2 or Shn3 activity.

As stated above, for simplicity, the below-mentioned exemplary stimulatory compounds will refer to Shn2 stimulatory compounds. However, it is understood that exemplary stimulatory compounds of the above-mentioned molecules, e.g., Shn3, a molecule in a signal transduction pathway involving Shn2, or a portion of said genes, are also included in the invention.

A preferred stimulatory compound is a nucleic acid molecule encoding Shn2, wherein the nucleic acid molecule is introduced into the subject (e.g., osteoblasts of the subject) in a form suitable for expression of the Shn2 protein in the cells of the subject. For example, a Shn2 cDNA (full length or partial Shn2 cDNA sequence) is cloned into a recombinant expression vector and the vector is transfected into the immune cell using standard molecular biology techniques. The Shn2 cDNA can be obtained, for example, by amplification using the polymerase chain reaction (PCR) or by screening an appropriate cDNA library. The nucleotide sequences of Shn2 cDNA is known in the art and can be used for the design of PCR primers that allow for amplification of a cDNA by standard PCR methods or for the design of a hybridization probe that can be used to screen a cDNA library using standard hybridization methods.

Following isolation or amplification of Shn2 cDNA, the DNA fragment is introduced into a suitable expression vector, as described above. Nucleic acid molecules encoding Shn2 in the form suitable for expression of the Shn2 in a host cell, can be prepared as described above using nucleotide sequences known in the art. The nucleotide sequences can be used for the design of PCR primers that allow for amplification of a cDNA by standard PCR methods or for the design of a hybridization probe that can be used to screen a cDNA library using standard hybridization methods.

Another form of a stimulatory compound for stimulating expression of Shn2 in a cell is a chemical compound that specifically stimulates the expression or activity of endogenous Shn2 in the cell. Such compounds can be identified using screening assays that select for compounds that stimulate the expression or activity of Shn2 as described herein.

The method of the invention for modulating Shn2 activity in a subject can be practiced either in vitro or in vivo (the latter is discussed further in the following subsection). For practicing the method in vitro, cells (e.g., osteoblasts) can be obtained from a subject by standard methods and incubated (i.e., cultured) in vitro with a stimulatory or inhibitory compound of the invention to stimulate or inhibit, respectively, the activity of Shn2. Methods for isolating osteoblasts are known in the art.

Cells treated in vitro with either a stimulatory or inhibitory compound can be administered to a subject to influence the growth and/or differentiation of cells in the subject.

In other embodiments, a stimulatory or inhibitory compound is administered to a subject in vivo, such as directly to an articulation site of a subject. For stimulatory or inhibitory agents that comprise nucleic acids (e.g., recombinant expression vectors encoding Shn2, antisense RNA, intracellular antibodies or Shn2-derived peptides), the compounds can be introduced into cells of a subject using methods known in the art for introducing nucleic acids (e.g., DNA) into cells in vivo. Examples of such methods include:

Direct Injection:

Naked DNA can be introduced into cells in vivo by directly injecting the DNA into the cells (see e.g., Acsadi et al. (1991) *Nature* 332:815-818; Wolff et al. (1990) *Science* 247:1465-1468). For example, a delivery apparatus (e.g., a "gene gun") for injecting DNA into cells in vivo can be used. Such an apparatus is commercially available (e.g., from BioRad).

Receptor-Mediated DNA Uptake:

Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126).

Retroviruses:

Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψ Crip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254: 1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. No. 4,868,116; U.S. Pat. No. 4,980, 286; PCT Pulication No. WO 89/07136; PCT Application WO 89/02468; PCT Publication No. WO 89/05345; and PCT Publication No. WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses:

The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252: 431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses:

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39;

Tratschin et al. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay.

III. Diagnostic Assays

In another aspect, the invention features a method of diagnosing a subject for a disorder associated with aberrant skeletal remodeling or patterning e.g., that would benefit from modulation of, e.g., modulation of bone growth, modulation of trabecular bone formation, modulation of bone mineralization, modulation of trabecular bone mineralization, modulation of trabecular bone formation in the diaphysis of a bone, modulation of trabecular bone mineralization in the diaphysis of a bone, modulation of osteoclastogenesis, modulation of osteoblast versus osteoclast activity.

For example, in one embodiment, expression of Shn2 or Shn2 and Shn3 can be detected in cells of a subject suspected of having a disorder associated with skeletal remodeling or patterning. The expression of Shn2 or Shn2 and Shn3 in cells of said subject could then be compared to a control and a difference in expression of Shn2 or Shn2 and Shn3 in cells of the subject as compared to the control could be used to diagnose the subject as one that would benefit from modulation of skeletal remodeling or patterning The "change in expression" or "difference in expression" of Shn2 or Shn2 and Shn3 in cells of the subject can be, for example, a change in the level of expression of Shn2 or Shn2 and Shn3 in cells of the subject as compared to a previous sample taken from the subject or as compared to a control, which can be detected by assaying levels of, e.g., Shn2 or Shn3 mRNA, for example, by isolating cells from the subject and determining the level of Shn2 or Shn3 mRNA expression in the cells by standard methods known in the art, including Northern blot analysis, microarray analysis, reverse-transcriptase PCR analysis and in situ hybridizations. For example, a biological specimen can be obtained from the patient and assayed for, e.g., expression or activity of Shn2 or Shn2 and Shn3. For instance, a PCR assay could be used to measure the level of Shn2 in a cell of the subject. A level of Shn2 or Shn2 and Shn3 higher or lower than that seen in a control or higher or lower than that previously observed in the patient indicates that the patient would benefit from modulation of Shn2 or Shn2 and Shn3. Alternatively, the level of expression of Shn2 or Shn2 and Shn3 in cells of the subject can be detected by assaying levels of, e.g., Shn2, for example, by isolating cells from the subject and determining the level of Shn2 or Shn2 and Shn3 protein expression by standard methods known in the art, including Western blot analysis, immunoprecipitations, enzyme linked immunosorbent assays (ELISAs) and immunofluorescence. Antibodies for use in such assays can be made using techniques known in the art and/or as described herein for making intracellular antibodies.

In another embodiment, a change in expression of Shn2 or Shn2 and Shn3 in cells of the subject results from one or more mutations (i.e., alterations from wildtype), e.g., the Shn2 gene and mRNA leading to one or more mutations (i.e., alterations from wildtype) in the amino acid sequence of the protein. In one embodiment, the mutation(s) leads to a form of the molecule with increased activity (e.g., partial or complete constitutive activity). In another embodiment, the mutation(s) leads to a form of the molecule with decreased activity (e.g., partial or complete inactivity). The mutation(s) may change the level of expression of the molecule for example, increasing or decreasing the level of expression of the molecule in a subject with a disorder. Alternatively, the mutation(s) may change the regulation of the protein, for example, by modulating the interaction of the mutant protein with one or more targets e.g., resulting in a form of Shn2 or Shn3 that cannot interact with a binding partner. Mutations in the nucleotide sequence or amino acid sequences of proteins can be determined using standard techniques for analysis of DNA or protein sequences, for example for DNA or protein sequencing, RFLP analysis, and analysis of single nucleotide or amino acid polymorphisms. For example, in one embodiment, mutations can be detected using highly sensitive PCR approaches using specific primers flanking the nucleic acid sequence of interest. In one embodiment, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *PNAS* 91:360-364). This method can include the steps of collecting a sample of cells from a patient, isolating nucleic acid (e.g., genomic, DNA) from the cells of the sample, contacting the nucleic acid sample with one or more primers which specifically amplify a sequence under conditions such that hybridization and amplification of the sequence (if present) occurs, and detecting the presence or absence of an amplification product, or detecting the size of the amplification product and comparing the length to a control sample.

In one embodiment, the complete nucleotide sequence for Shn2 or Shn2 and Shn3 can be determined. Particular techniques have been developed for determining actual sequences in order to study polymorphism in human genes. See, for example, Proc. Natl. Acad. Sci. U.S.A. 85, 544-548 (1988) and Nature 330, 384-386 (1987); Maxim and Gilbert. 1977. PNAS 74:560; Sanger 1977. *PNAS* 74:5463. In addition, any of a variety of automated sequencing procedures can be utilized when performing diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Restriction fragment length polymorphism mappings (RFLPS) are based on changes at a restriction enzyme site. In one embodiment, polymorphisms from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Moreover, the use of sequence specific ribozymes (see, for example, U.S. Pat. No. 5,498,531) can be used to score for the presence of a specific ribozyme cleavage site.

Another technique for detecting specific polymorphisms in particular DNA segment involves hybridizing DNA segments which are being analyzed (target DNA) with a complimentary, labeled oligonucleotide probe. See Nucl. Acids Res. 9, 879-894 (1981). Since DNA duplexes containing even a single base pair mismatch exhibit high thermal instability, the differential melting temperature can be used to distinguish target DNAs that are perfectly complimentary to the probe from target DNAs that only differ by a single nucleotide. This method has been adapted to detect the presence or absence of a specific restriction site, U.S. Pat. No. 4,683,194. The method involves using an end-labeled oligonucleotide probe spanning a restriction site which is hybridized to a target DNA. The hybridized duplex of DNA is then incubated with the restriction enzyme appropriate for that site. Reformed restriction sites will be cleaved by digestion in the pair of duplexes between the probe and target by using the restriction endonuclease. The specific restriction site is present in the target DNA if shortened probe molecules are detected.

Other methods for detecting polymorphisms in nucleic acid sequences include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the polymorphic sequence with potentially polymorphic RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels. See, for example, Cotton et al. (1988) *Proc. Natl. Acad Sci USA* 85:4397; Saleeba et al. (1992) *Methods Enzymol.* 217:286-295. In a preferred embodiment, the control DNA or RNA can be labeled for detection.

In another embodiment, alterations in electrophoretic mobility can be used to identify polymorphisms. For example, single strand conformation polymorphism (SSCP) may be used to detect differences in electrophoretic mobility between mutant and wild type nucleic acids (Orita et al. (1989) *Proc Natl. Acad. Sci. USA:* 86:2766, see also Cotton (1993) *Mutat Res* 285:125-144; and Hayashi (1992) *Genet Anal Tech Appl* 9:73-79). Single-stranded DNA fragments of sample and control nucleic acids can be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of nucleic acid molecule comprising polymorphic sequences in polyacrylamide gels containing a gradient of denaturant is assayed using denaturing gradient gel electrophoresis (DGGE) (Myers et al. (1985) *Nature* 313:495). When DGGE is used as the method of analysis, DNA can be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265: 12753).

Examples of other techniques for detecting polymorphisms include, but are not limited to, selective oligonucleotide hybridization, selective amplification, or selective primer extension. For example, oligonucleotide primers may be prepared in which the polymorphic region is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different polymorphisms when the oligonucleotides are attached to the hybridizing membrane and hybridized with labeled target DNA.

Another process for studying differences in DNA structure is the primer extension process which consists of hybridizing a labeled oligonucleotide primer to a template RNA or DNA and then using a DNA polymerase and deoxynucleoside triphosphates to extend the primer to the 5' end of the template. Resolution of the labeled primer extension product is then done by fractionating on the basis of size, e.g., by electrophoresis via a denaturing polyacrylamide gel. This process is often used to compare homologous DNA segments and to detect differences due to nucleotide insertion or deletion. Differences due to nucleotide substitution are not detected since size is the sole criterion used to characterize the primer extension product.

Another process exploits the fact that the incorporation of some nucleotide analogs into DNA causes an incremental shift of mobility when the DNA is subjected to a size fractionation process, such as electrophoresis. Nucleotide analogs can be used to identify changes since they can cause an electrophoretic mobility shift. See, U.S. Pat. No. 4,879, 214.

Many other techniques for identifying and detecting polymorphisms are known to those skilled in the art, including those described in "DNA Markers: Protocols, Applications and Overview," G. Caetano-Anolles and P. Gresshoff ed., (Wiley-VCH, New York) 1997, which is incorporated herein by reference as if fully set forth.

In addition, many approaches have also been used to specifically detect SNPs. Such techniques are known in the art and many are described e.g., in DNA Markers: Protocols, Applications, and Overviews. 1997. Caetano-Anolles and Gresshoff, Eds. Wiley-VCH, New York, pp 199-211 and the references contained therein). For example, in one embodiment, a solid phase approach to detecting polymorphisms such as SNPs can be used. For example an oligonucleotide ligation assay (OLA) can be used. This assay is based on the ability of DNA ligase to distinguish single nucleotide differences at positions complementary to the termini of co-terminal probing oligonucleotides (see, e.g., Nickerson et al. 1990. *Proc. Natl. Acad. Sci. USA* 87:8923. A modification of this approach, termed coupled amplification and oligonucleotide ligation (CAL) analysis, has been used for multiplexed genetic typing (see, e.g., Eggerding 1995 *PCR Methods Appl.* 4:337); Eggerding et al. 1995 Hum. Mutat. 5:153).

In another embodiment, genetic bit analysis (GBA) can be used to detect a SNP (see, e.g., Nikiforov et al. 1994. Nucleic Acids Res. 22:4167; Nikiforov et al. 1994. PCR Methods Appl. 3:285; Nikiforov et al. 1995. Anal Biochem. 227:201). In another embodiment, microchip electrophoresis can be used for high-speed SNP detection (see e.g., Schmalzing et al. 2000. *Nucleic Acids Research*, 28). In another embodiment, matrix-assisted laser desorption/ionization time-of-flight mass (MALDI TOF) mass spectrometry can be used to detect SNPs (see, e.g., Stoerker et al. Nature Biotechnology 18:1213).

In another embodiment, a difference in a biological activity of Shn2 or Shn2 and Shn3 between a subject and a control can be detected. For example, an activity of Shn2 or Shn2 and Shn3 can be detected in cells of a subject suspected of having a disorder associated with aberrant skeletal remodeling or patterning. The activity of Shn2 or Shn2 and Shn3 in cells of the subject could then be compared to a control and a difference in activity of Shn2 or Shn2 and Shn3 in cells of the subject as compared to the control could be used to diagnose the subject as one that would benefit from modulation of bone formation. Activities of Shn2 or Shn2 and Shn3 can be detected using methods described herein or known in the art.

In preferred embodiments, the diagnostic assay is conducted on a biological sample from the subject, such as a cell sample or a tissue section (for example, a freeze-dried or fresh frozen section of tissue removed from a subject). In another embodiment, the level of expression of Shn2 or Shn2 and Shn3 in cells of the subject can be detected in vivo, using an appropriate imaging method, such as using a radiolabeled antibody.

In one embodiment, the level of expression of Shn2 or Shn2 and Shn3 in cells of the test subject may be elevated (i.e., increased) relative to the control not associated with the disorder or the subject may express a constitutively active (partially or completely) form of the molecule. This elevated expression level of, e.g., Shn2 or expression of a constitutively active form of Shn2, can be used to diagnose a subject for a disorder associated with increased Shn2 activity.

In another embodiment, the level of expression of Shn2 or Shn2 and Shn3 in cells of the subject may be reduced (i.e., decreased) relative to the control not associated with the disorder or the subject may express an inactive (partially or completely) mutant form of Shn2. This reduced expression level of Shn2 or expression of an inactive mutant form of Shn2 can be used to diagnose a subject for a disorder, such as immunodeficiency disorders characterized by insufficient cytokine production.

In one embodiment, the level of expression of gene whose expression is regulated by Shn2 can be measured (e.g., osterix, osteocalcin, GATA3, PPAR-gamma).

In another embodiment, an assay diagnosing a subject as one that would benefit from modulation of Shn2 expression, post-translational modification, and/or activity (or a molecule in a signal transduction pathway involving Shn2) is performed prior to treatment of the subject.

The methods described herein may be performed, for example, by utilizing pre-packaged diagnostic kits comprising at least one probe/primer nucleic acid or other reagent (e.g., antibody), which may be conveniently used, e.g., in clinical settings to diagnose patients exhibiting symptoms or family history of a disease or illness involving Shn2 or Shn2 and Shn3.

IV. Administration of Modulating Agents

Modulating agents of the invention are administered to subjects in a biologically compatible form suitable for pharmaceutical administration in vivo or on a surface to increase or decrease bone formation and mineralization. By "biologically compatible form suitable for administration in vivo" is meant a form of the protein to be administered in which any toxic effects are outweighed by the therapeutic effects of the modulating agent. The term subject is intended to include living organisms in which bone formation and mineralization can be elicited, e.g., mammals. Examples of subjects include humans, dogs, cats, mice, rats, and transgenic species thereof, including but not limited to the transgenic mouse described herein. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a modulating agent may vary according to factors such as the disease state, age, sex, reproductive state, and weight of the individual, and the ability of the agent to elicit a desired response in the individual. Dosage regimen may be adjusted to provide the optimum therapeutic response. For example, several divided doses may be administered daily or the dose may be proportionally reduced as indicated by the exigencies of the therapeutic situation.

The therapeutic or pharmaceutical compositions of the present invention can be administered by any suitable route known in the art including for example intravenous, subcutaneous, intramuscular, transdermal, intrathecal or intracerebral or administration to cells in ex vivo treatment protocols, or delivered on a surface, e.g., a biocompatible surface, for example on the surface of a surgically implanted device, e.g., as, for example, a putty, for the stabilization, replacement, etc., of a bone, joint, tooth, etc. Administration can be either rapid as by injection or over a period of time as by slow infusion or administration of slow release formulation.

The Shn2 or Shn3 or Shn2 and Shn3 modulator can also be linked or conjugated with agents that provide desirable pharmaceutical or pharmacodynamic properties. For example, it can be stably linked to a polymer such as polyethylene glycol to obtain desirable properties of solubility, stability, half-life and other pharmaceutically advantageous properties. (See for example Davis et al., 1978, *Enzyme Eng* 4: 169-73; Burnham, 1994, *Am J Hosp Pharm* 51: 210-218, which are incorporated by reference).

Furthermore, the Shn2 or Shn3 or Shn2 and Shn3 modulator can be in a composition which aids in delivery into the cytosol of a cell. For example, the agent may be conjugated with a carrier moiety such as a liposome that is capable of delivering the peptide into the cytosol of a cell. Such methods are well known in the art (for example, see Amselem et al., 1993, *Chem Phys Lipids* 64: 219-237, which is incorporated by reference). Alternatively, the modulator can be modified to include specific transit peptides or fused to such transit peptides which are capable of delivering the modulator into a cell. In addition, the agent can be delivered directly into a cell by microinjection.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. Shn2 can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used. It is also provided that certain formulations containing the Shn2 modulator are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, olyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method for the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment of this invention, a modulator may be therapeutically administered by implanting into patients vectors or cells capable of producing a biologically-active form of Shn2 or Shn2 and Shn3. In one approach cells that secrete Shn2 may be encapsulated into semipermeable membranes for implantation into a patient. The cells can be cells that normally express Shn2 or Shn2 and Shn3 or the cells can be transformed to express Shn2 or Shn2 and Shn3 or a biologically active fragment thereof or a precursor thereof. It is preferred that the cell be of human origin and that the Shn2 polypeptide be human Shn2 when the patient is human. However, the formulations and methods herein can be used for veterinary as well as human applications and the term "patient" or "subject" as used herein is intended to include human and veterinary patients.

Monitoring the influence of agents (e.g., drugs or compounds) on the expression or activity of a Shn2 or Shn2 and Shn3 protein can be applied not only in basic drug screening, but also in clinical trials. For example, the effectiveness of an agent determined by a screening assay as described herein to increase gene expression, protein levels, or upregulate biological activity, can be monitored in clinical trials of subjects exhibiting decreased gene expression, protein levels, or downregulated activity. Alternatively, the effectiveness of an agent determined by a screening assay to decrease gene expression, protein levels, or downregulate biological activity, can be monitored in clinical trials of subjects exhibiting increased gene expression, protein levels, or upregulated activity. In such clinical trials, the expression or activity of a Shn2 or Shn2 and Shn3 gene, and preferably, other genes that have been implicated in a disorder can be used as a "read out" or markers of the phenotype of a particular cell.

For example, and not by way of limitation, levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Shn2 or Shn2 and Shn3. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a Shn2 or Shn2 and Shn3 protein, mRNA, or genomic DNA in the pre-administration sample; (iii) obtaining one or more post-administration samples from the subject; (iv) detecting the level of expression or activity of the Shn2 or Shn2 and Shn3 protein, mRNA, or genomic DNA in the post-administration samples; (v) comparing the level of expression or activity of the Shn2 or Shn2 and Shn3 protein, mRNA, or genomic DNA in the pre-administration sample with the Shn2 or Shn2 and Shn3 protein, mRNA, or genomic DNA in the post administration sample or samples; and (vi) altering the administration of the agent to the subject accordingly. For example, increased administration of the agent may be desirable to increase the expression or activity of Shn2 or Shn2 and Shn3 to higher levels than detected, i.e., to increase the effectiveness of the agent. Alternatively, decreased administration of the agent may be desirable to decrease expression or activity of Shn2 to lower levels than detected, i.e. to decrease the effectiveness of the agent. According to such an embodiment, Shn2 or Shn2 and Shn3 expression or activity may be used as an indicator of the effectiveness of an agent, even in the absence of an observable phenotypic response.

In a preferred embodiment, the ability of a modulating agent to modulate bone formation and mineralization in a cell can be measured by detecting an improvement in the condition of the patient after the administration of the agent. Such improvement can be readily measured by one of ordinary skill in the art using indicators appropriate for the specific condition of the patient. Monitoring the response of the patient by measuring changes in the condition of the patient is preferred in situations were the collection of biopsy materials would pose an increased risk and/or detriment to the patient.

Furthermore, in the treatment of disease conditions, compositions containing Shn2 or Shn2 and Shn3 can be administered exogenously and it would likely be desirable to achieve certain target levels of Shn2 or Shn2 and Shn3 in any desired tissue compartment or in the affected tissue. It would, therefore, be advantageous to be able to monitor the levels of Shn2 or Shn2 and Shn3 polypeptide in a patient or in a biological sample including a tissue biopsy sample, e.g. bone. Accordingly, the present invention also provides methods for detecting the presence of Shn2 or Shn2 and Shn3 in a sample from a patient.

VI. Pharmaceutical Compositions

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition will preferably be sterile and should be fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freezedrying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the test compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

VII. Kits of the Invention

Another aspect of the invention pertains to kits for carrying out the screening assays, modulatory methods or diagnostic assays of the invention. For example, a kit for carrying out a screening assay of the invention can include an indicator composition comprising Shn2 or Shn3 or Shn2 and Shn3, means for measuring a readout (e.g., protein secretion) and instructions for using the kit to identify modulators of biological effects of Shn2 or Shn2 and Shn3. In another embodiment, a kit for carrying out a screening assay of the invention can include cells deficient in Shn2 or Shn2 and Shn3, means for measuring the readout and instructions for using the kit to identify modulators of skeletal remodeling and/or patterning.

In another embodiment, the invention provides a kit for carrying out a modulatory method of the invention. The kit can include, for example, a modulatory agent of the invention (e.g., Shn2 inhibitory or stimulatory agent) in a suitable carrier and packaged in a suitable container with instructions for use of the modulator to modulate a biological effect of Shn2 or Shn3 or Shn2 and Shn3.

Another aspect of the invention pertains to a kit for diagnosing a disorder associated with a biological activity of Shn2 or Shn2 and Shn3 in a subject. The kit can include a reagent for determining expression of Shn2 or Shn2 and Shn3 (e.g., a nucleic acid probe for detecting Shn2 or Shn2 and Shn3 mRNA or an antibody for detection of protein), a control to which the results of the subject are compared, and instructions for using the kit for diagnostic purposes.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

This invention is further illustrated by the following examples which should not be construed as limiting. The contents of all references, patents, and published patent applications cited throughout this application, as well as the figures and the sequence listing, are hereby incorporated by reference.

The following materials and methods were used throughout the following Examples:

Animals

Compound Shn2/3-mutant mice were generated using the previously described strains of Shn3−/− mice. Animals were maintained in accordance with the NIH Guide for the Care and Use of Laboratory Animals and were handled according to protocols approved by the institution's subcommittee on animal care (IACUC).

Skeletal Preparation

Mice were skinned, eviscerated and dehydrated in 95% ETOH overnight. The samples were then transferred into acetone for an additional forty-eight hour incubation. Skeletal preparations were stained for four days using alcian blue and alizarin red as described previously (McLeod, 1980). Following staining, the samples were washed for thirty minutes three times in 95% ETOH. The soft tissue was then cleared in 1% KOH.

uCT Imaging and Analysis

Proximal femurs were isolated from WT and Shn2/3-compound mutant mice and fixed in 70% ethanol. Samples were scanned using a Scanco Medical i_tCT 35 system (Scanco). Images were reconstructed into three-dimensional (3-D) volumes using true Feldkamp reconstruction with 16-bit gray levels. Unbiased, 3-D microstructural properties of trabecular bone, including bone volume fraction (BV/TV), trabecular thickness (Tb.Th), trabecular number (Tb.N.), trabecular separation (Tb.Sp.) were then calculated for the trabecular region of the metaphysis of the distal femur.

Histology and In Situ Hybridization.

Generation and preparation of skeletal tissue for histological analysis and in situ hybridization were performed as described previously (Shim et al., 2009). In situ probes for Collagen X, Collagen I and Osteocalcin were kindly provided by Dr. Beate Lanske. Transcript specific probes for Schnurri-2 and Schnurri-3 were generated by subcloning cDNA fragments into pBluescript. Digoxigenine (DIG)-labelled RNA probes were then generated by T7 or T3 RNA polymerase according to manufacturer's protocol.

Figure 1A:
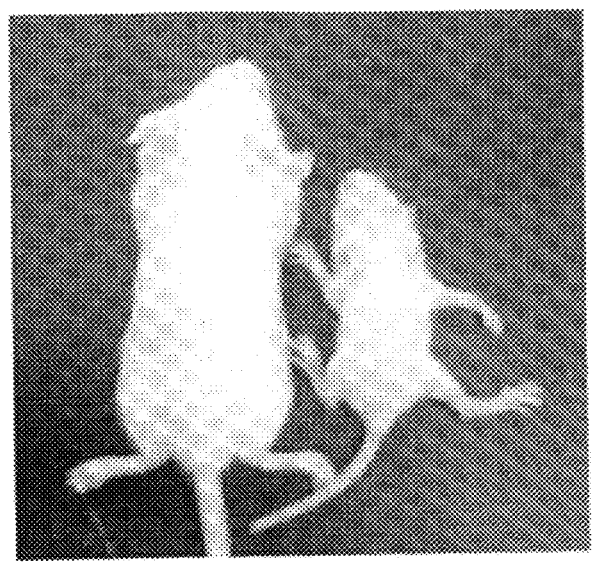
FIG. 1. Skeletal patterning defects in mice lacking Shn2 and Shn3. (A) Dwarfed phenotype of Shn2/3-DKO mouse (Right) when compared to WT control (Left). (B) Growth curve of WT (filled circle) and Shn2/3-DKO mice (open circle) from P0 to P14 (C) Alizarin red and alcian blue stained skeletal preps of two-week old WT and Shn2/3-DKO mice. Comparison of (D) lumbar and (E) thoracic vertebrae isolated from Shn2/3-DKO mice and WT mice. (F) Irregular sternalcostal junctions are also observed in Shn2/3-DKO mice.
Figure 1B:
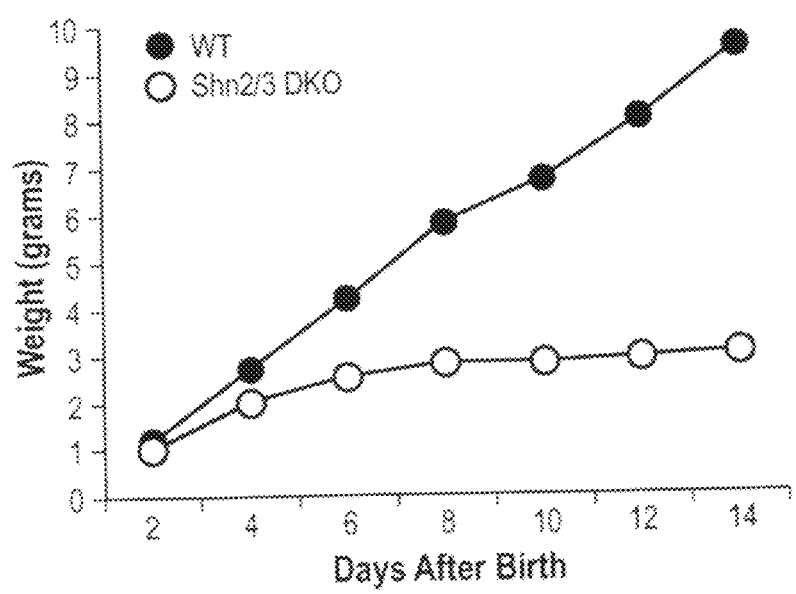
Figure 1C:
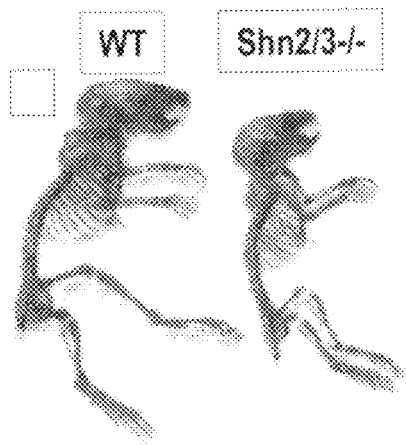
Figure 1F:
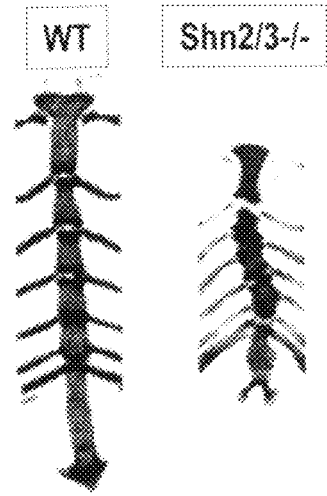
Figure 1D:
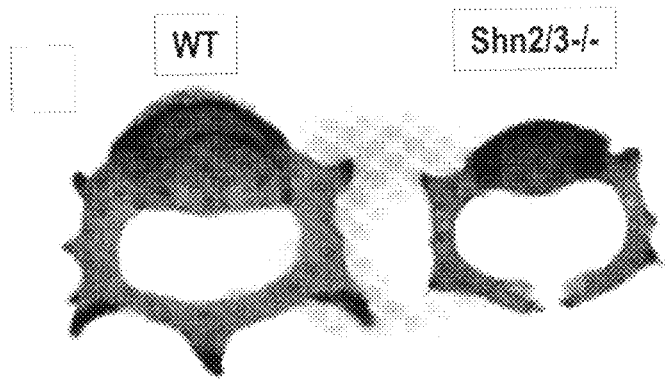
Figure 1E:
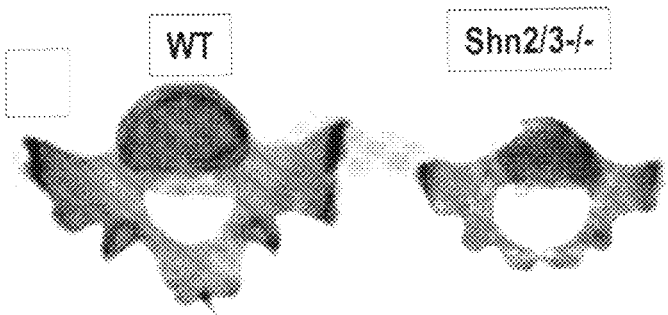

Example 1. Deletion of Shn2 and Shn3 Results in Growth Defects and Skeletal Pathology We hypothesized that compensatory functions may exist between Shn2 and Shn3 in tissues where expression of these two genes overlaps. To address this, we utilized previously characterized Shn2−/− mice and Shn3−/− mice to generate compound mutant mice deficient in both Shn2 and Shn3 (Shn2/3-DKO) (Jin et al., 2006; Jones et al., 2006; Kimura et al., 2005; Kimura et al., 2007; Saita et al., 2007; Takagi et al., 2001). Shn2/3-DKO mice are indistinguishable from control littermates at birth but thereafter display a severe growth retardation that results in a dwarfed phenotype (FIG. 1A-B). Examination of skeletal preparations revealed that the dwarfism in Shn2/3-DKO mice arises from shortening of both axial and appendicular skeletons (FIG. 1C). Our subsequent analysis of the axial skeleton uncovered patterning defects in the Shn2/3-DKO vertebrae and sternum. As shown in FIG. 1D-E, spinous processes were absent from lumbar and thoracic vertebrae of Shn2/3-DKO mice. The incomplete formation of these vertebrae also resulted in a non-ossified gap being present along the vertebral dorsal midline (FIG. 1D-E). The absence of Shn2 and Shn3 also resulted in impaired sternum development as abnormal sternocostal junctions were commonly observed in Shn2/3-DKO mice (FIG. 1F). These results further expand the previously established role for Shn2 and Shn3 in skeletal remodeling by describing an unknown function for Shn2 and Shn3 in skeletal patterning.

Example 2. Growth Plate Abnormalities in Mice Deficient for Shn2 and Shn3

Figure 2A:
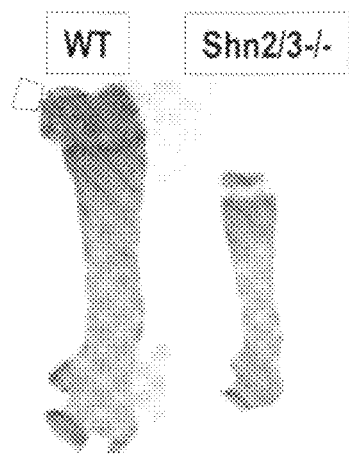
FIG. 2. Histological analysis of the growth plates from Shn2/3-DKO mice. (A) Alizarin red and alcian blue staining of femurs isolated from two-week old WT and Shn2/3-DKO mice. In situ hybridization depicting the expression of (B) Shn2 and (C) Shn3 in the growth plate of the distal femur. Safranin 0 stained histological sections from the distal femur of (D, F) WT and (E, G) Shn2/3-DK0 mice. Detection of Col X expression by in situ hybridization in the distal femur of (H) WT and (I) Shn2/3-DKO mice. Detection of BrdU labeled chondrocytes in the distal femoral growth plate of (J, L) WT and (K, M) Shn2/3-DKO mice. (L, M) Higher magnifications of the growth plate. Haemotoxylin and Eosin staining of limbs isolated from (N) WT and (O) Shn2/3-DKO mice at E16.5.
Figure 2B:
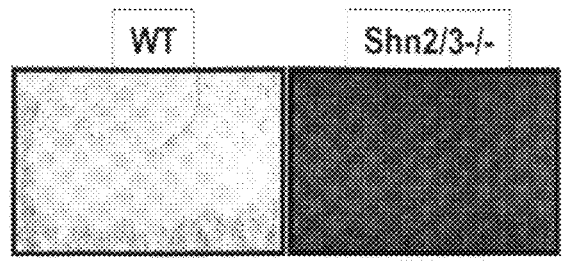
Figure 2C:
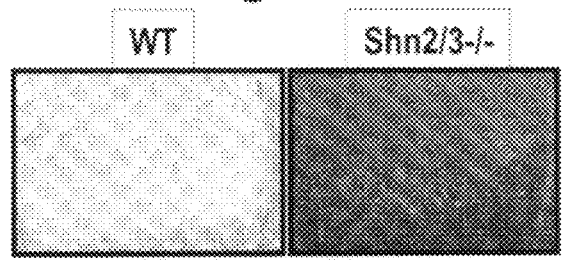
Figure 2D:
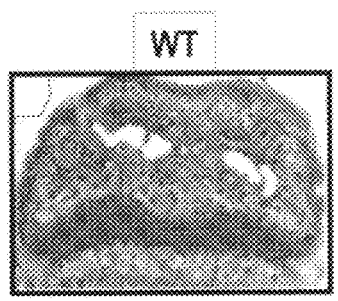
Figure 2E:
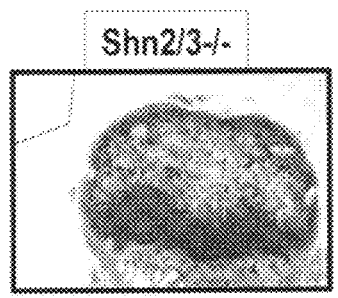
Figure 2F:
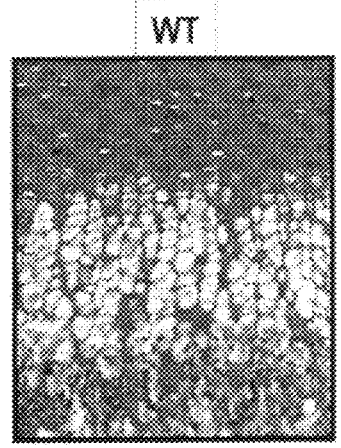
Figure 2G:
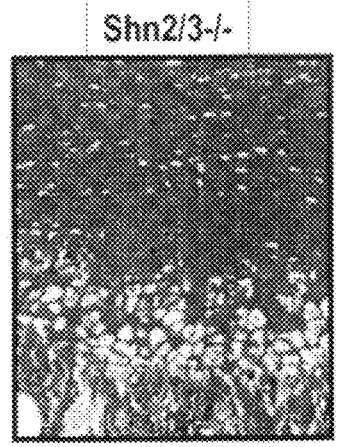
Figure 2H:
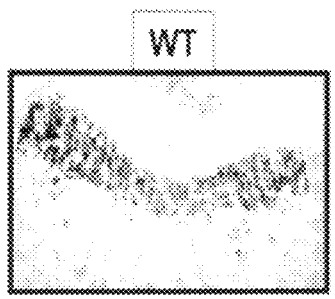
Figure 2I:
Figure 2J:
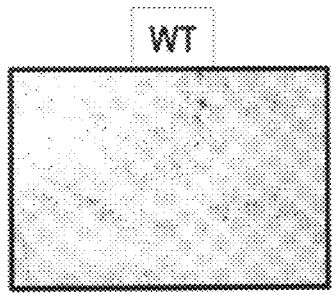
Figure 2K:
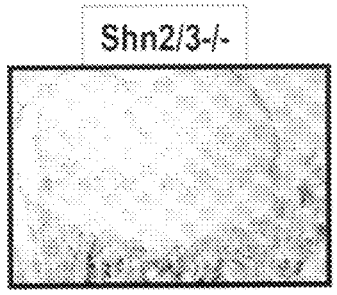
Figure 2L:
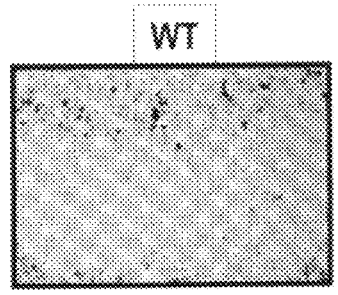
Figure 2M:
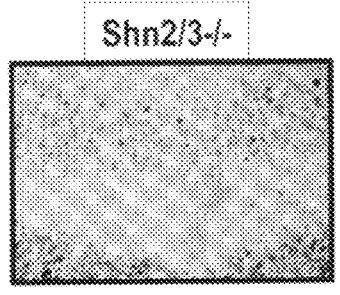

Analysis of proximal and distal bones isolated from the limbs of Shn2/3-DKO mice revealed a remarkable shortening when compared to WT bones (FIG. 2A). Given the central role of chondrocyte proliferation and differentiation in dictating the growth of long bones, we analyzed femurs isolated from WT neonatal mice for expression of Shn2 and Shn3 by in situ hybridization. As shown in FIGS. 2B-C, expression of Shn2 and Shn3 in the growth plate was detected in both proliferating and hypertrophic chondrocyte populations. Based on the overlapping expression of Shn2 and Shn3 in the different chondrocyte populations, we next asked if there was any discernable pathology at the growth plate of the Shn2/3-DKO mice. Histological examination of the distal femoral growth plates revealed the hypertrophic zone of the Shn2/3-DKO mice to be disorganized and smaller when compared to the hypertrophic zone of WT mice (FIG. 2D-G). A reduction in the size of the Shn2/3-DKO hypertrophic zone was further confirmed by in situ hybridization for type X collagen (ColX), a marker specific for hypertrophic chondrocytes (FIG. 2H-I).

In other murine models of chondrodysplasia, reductions in chondrocyte proliferation often are observed in concert with defects in chondrocyte maturation (Naski et al., 1998). To determine if chondrocyte proliferation was altered in Shn2/3-DKO mice, we assessed BrdU incorporation into the growth plates of Shn2/3-DKO mice and littermate controls. As shown in FIG. 2J-M, the epiphyseal growth plate of femurs isolated from Shn2/3-DKO mice 6 hrs after BrdU injection showed a marked reduction in the number of BrdU positive cells within the proliferative zone when compared to the growth plates of control littermates.

Figure 2N:
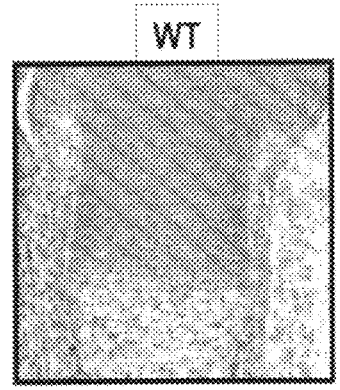
Figure 2O:
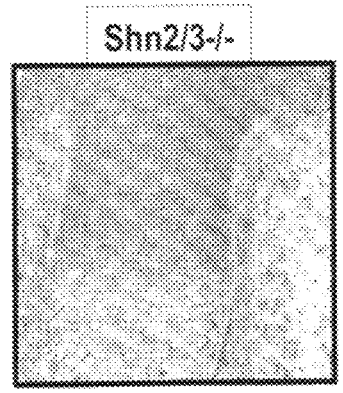

Reductions in chondrocyte proliferation coupled to alterations in differentiation that are observed in the Shn2/3-DKO mice are consistent with other dwarfism phenotypes that arise in mice through chondrodysplasia. Defects in chondrocyte biology also result in delayed formation of the secondary ossification center that is often observed in chondrodysplastic phenotypes (Chen et al., 2008; Lee and Behringer, 2007; Naski et al., 1998). Indeed, the formation of the secondary ossification center in the epiphysis of the Shn2/3-DKO femurs was also delayed (FIG. 2D-E). To address whether the appearance of the primary ossification center was also delayed, we isolated limbs from E16.5 Shn2/3-DKO and control littermates. Histological analysis of the E16.5 limbs revealed an established primary ossification center in both Shn213-DKO and control littermates with no discernable difference observed in limb size and morphology between these two groups (FIG. 2N-O). The postnatal onset of the chondrodysplasia demonstrates a previously uncharacterized function for Shn2 and Shn3 in regulating chondrocyte proliferation and maturation and further expands the significant role of this protein family in skeletal biology.

Example 3. Persistence of High Bone Mass Phenotype in Shn2/3-DKO Mice

Figure 3A:
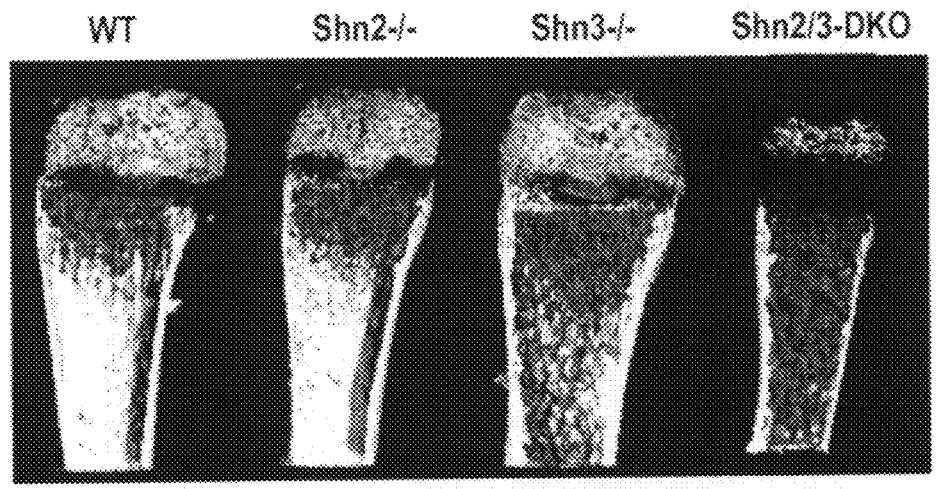
FIG. 3. Shn2/3-DKO mice exhibit elevated trabecular bone mass. (A) False colored three-dimensional u-QCT image demonstrating the various degrees of trabecular bone in the distal femurs isolated from WT, Shn2-/-, Shn3-/- and Shn2/3-DKO mice. Additional false-colored, CT image of diaphysial region of (B) WT and (C) Shn2/3-DKO femurs showing trabecular bone are shown. In situ hybridization detecting the presence of (D) osteocalcin (OCN) and (E) type 1 collagen (Col1 a1) positive cells lining the trabeculae in the diaphysis of Shn2/3-DKO femurs. Toluidine blue stained tissue sections from (F) WT and (G) Shn2/3-DKO femurs. (H) High magnification of the midshaft region of Shn2/3-DKO femur. Detection of TRAP-positive osteoclasts at the growth plate of (I) WT and (J) Shn2/3-DKO mice.
Figure 3B:
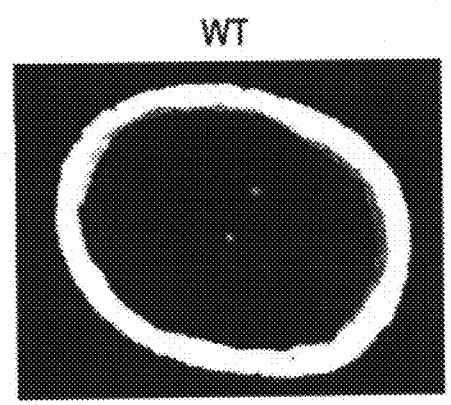
Figure 3C:
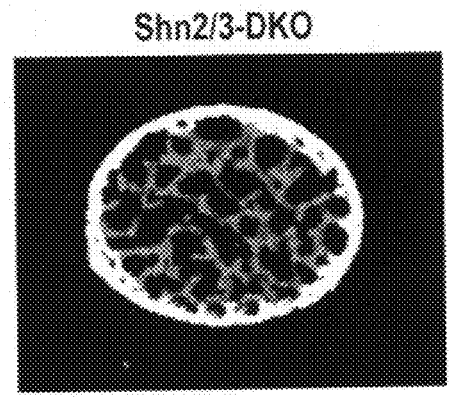
Figure 3D:
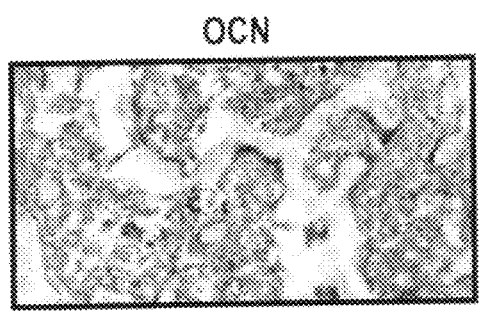
Figure 3E:
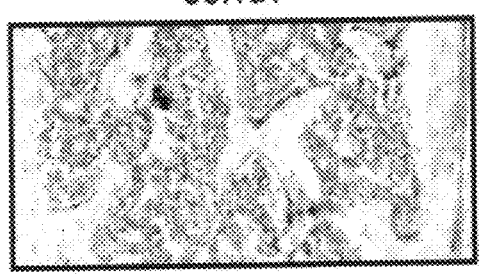

Skeletal elements formed through endochondral ossification are derived from cartilaginous templates that are replaced by osteoblast derived bone matrix. Decreases in bone mass are therefore frequently observed in mice with genetic mutations that impede the formation of the cartilaginous template through a disruption in chondrocyte biology (Bonaventure et al., 1992; Forlino et al., 2005; Maeda et al., 2007). Accordingly, we anticipated that the osteosclerotic phenotype that we previously reported to be present in the Shn3−/− strain would not be preserved in the chondrodysplastic Shn2/3-DKO mice (Jones et al., 2006). However, examination of long bones harvested from two-week old WT, Shn2−/−, Shn3−/− and Shn2/3-DKO mice revealed, unexpectedly, that a high bone mass phenotype was still present in the Shn2/3-DKO mice (FIG. 3A). Additionally, the onset of this skeletal phenotype was accelerated in the Shn2/3-DKO mice. Long bones isolated from two-week old Shn2/3-DKO mice already exhibited markedly increased trabecular bone volume in comparison to age-matched Shn3−/− mice which displayed only a modest increase in trabecular bone volume at that age (FIG. 3A). Further analysis of the femurs isolated from Shn2/3-DKO mice revealed that the extensive trabecular network extended well into the diaphyseal region where it appeared to be emanating from the endosteal surface (FIG. 3B-C). In situ hybridization revealed that the trabecular bones in this distal region of the Shn2/3-DKO femurs were lined with cells expressing canonical osteoblast markers such as osteocalcin and type I collagen suggesting that the increased bone mass arose from augmented osteoblast activity (FIG. 3D-E) and similar to what we had previously observed in single Shn3−/− mice (Jones et al., 2006).

The extensive trabecular network present in the long bones of the Shn2/3-DKO mice could also arise through a failure of osteoclasts to resorb the primary spongiosa. Decreased osteoclast differentiation and/or function may result in trabecular bones consisting of calcified cartilage. To address this, we analyzed histological tissue sections of WT and Shn2/3-DKO femurs that were stained with toluidine blue to detect the presence of calcified cartilage. As shown in FIG. 3F, trabecular bone in the femurs of WT mice is located in close proximity to the growth plate where it was extensively stained for toluidine blue. In contrast, the numerous trabeculae that are located in the diaphyseal regions of the Shn2/3-DKO femurs are toluidine blue negative suggesting that the cartilaginous template has been effectively resorbed in the Shn2/3-DKO femurs and replaced with osteoblast-derived lamellar bone (FIG. 3G-H). To further address whether osteoclastogenesis was impaired in the Shn2/3-DKO mice, we analyzed femurs from age-matched WT and Shn2/3-DKO mice for the presence of tartrate-resistant acid phosphatase-positive (TRAP-positive) osteoclasts. In comparison to age-matched WT controls, Shn2/3-DKO mice showed similar numbers of TRAP-positive cells providing additional evidence that the increased trabecular bone mass in the Shn2/3-DKO mice does not arise from a perturbation of osteoclast activity (FIG. 3I-J). Collectively, these results provide a unique demonstration of endochondral bone formation where the formation of trabecular bones can occur in skeletal elements that also exhibit impaired growth plate maturation.

Figure 4A:
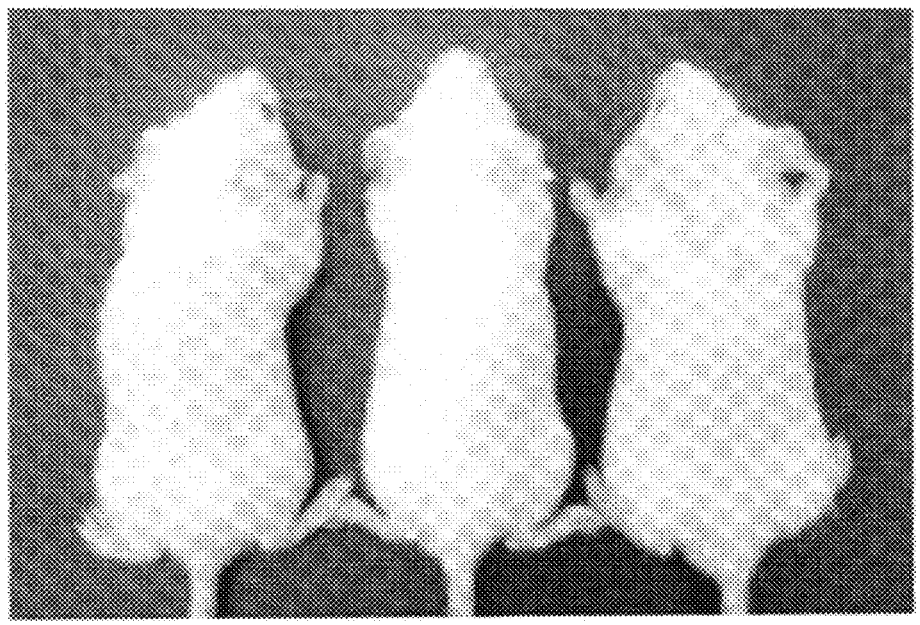
FIG. 4. Effects of Schnurri gene dosage on growth plate and trabecular bone formation. (A) Photograph of five-week old WT, Shn2-/-Shn3+/- and Shn2+/-Shn3-/- mice. (B) Hematoxylin and Eosin (H&E) staining of distal femoral growth plate of WT, Shn2-/-Shn3+/- and Shn2+/-Shn3-/- mice. (C) Three-dimensional u-QCT images of the distal femurs isolated from the various Shn2/3-compound mutant mice. Analysis of the u-QCT images for bone volume per tissue volume (BV/TV), trabecular number (Tb.N.) and trabecular thickness (Tb.Th.) is shown below panel C. (D) von Kossa staining of bone marrow stromal cultures generated from Shn3+/-, Shn2+/-Shn3+/-, Shn3-/- and Shn2+/-Shn3-/- mice.
Figure 4B:
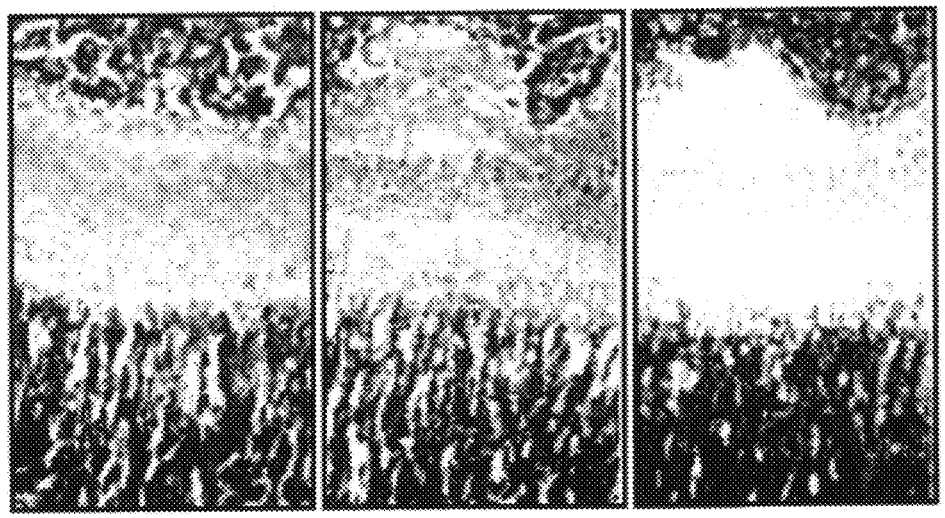
Figure 4C:
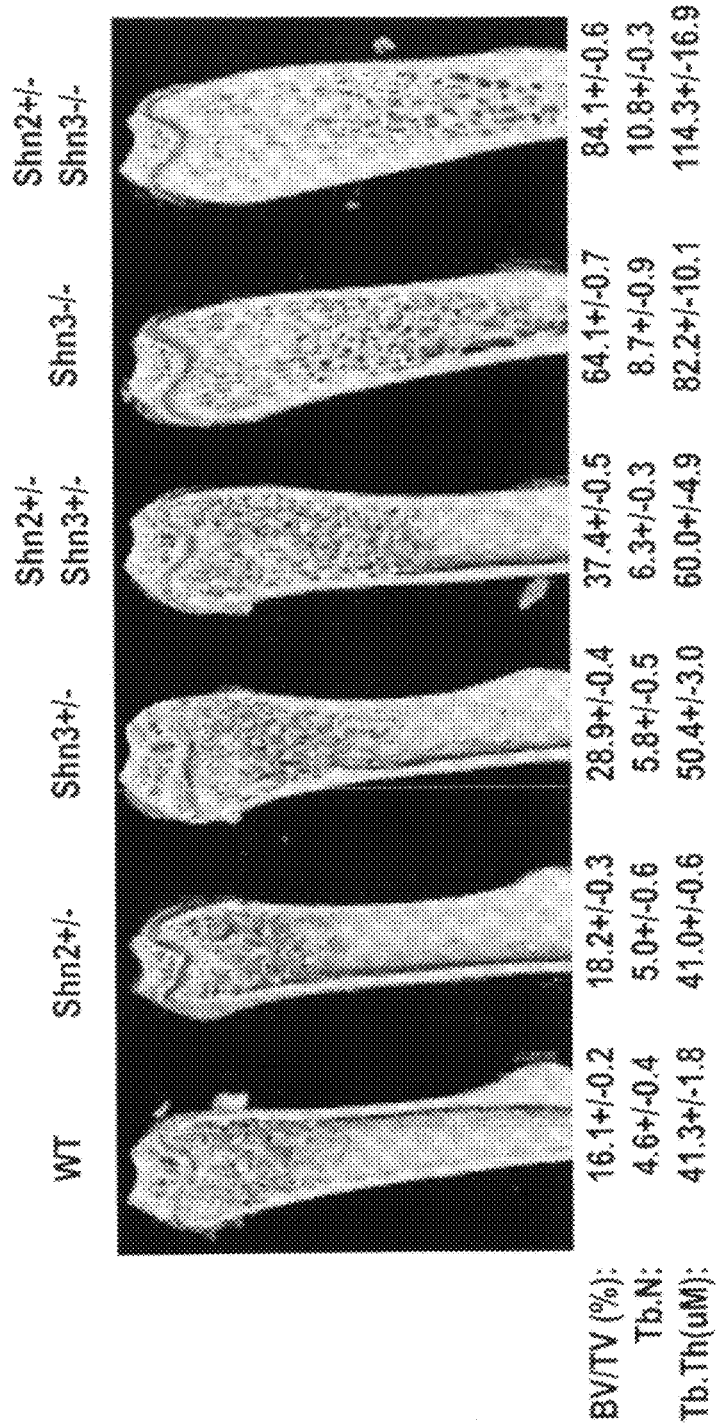

Example 4. Onset of Chondrodysplasia and Elevated Bone Mass Exhibit Differing Sensitivities to Schnurri Gene Dosage We observed during the generation and characterization of the Shn2/3-compound mutant mice that the growth defects identified in the Shn2/3-DKO mice were not present in mice containing only a single copy of Shn2 (Shn2+/−Shn3−/−) or a single copy of Shn3 (Shn2−/−Shn3+/−) (FIG. 4A). Accordingly, the growth plate architecture of the Shn2+/−Shn3−/− and Shn2−/−Shn3+/− mice was comparable to that of WT mice and did not display any of the pathological characteristics seen in the Shn2/3-DKO mice (FIG. 4B). These findings indicate that complete ablation of both Shn2 and Shn3 is necessary to perturb growth plate maturation. In contrast, deletion of a single Shn3 allele (Shn3+/−) was sufficient to cause an increase in bone mass. Moreover, deletion of a single copy of Shn2 in parallel with a single copy of Shn3 (Shn2+/−Shn3+/−) resulted in a further augmentation of this bone mass phenotype (FIG. 4C). Analysis of the femurs isolated from Shn2+/−Shn3−/− mice revealed a BV/TV that was 5-fold that of the WT controls (FIG. 4C). These data demonstrate that bone formation is highly sensitive to Schnurri gene dosage in vivo.

Figure 4D:
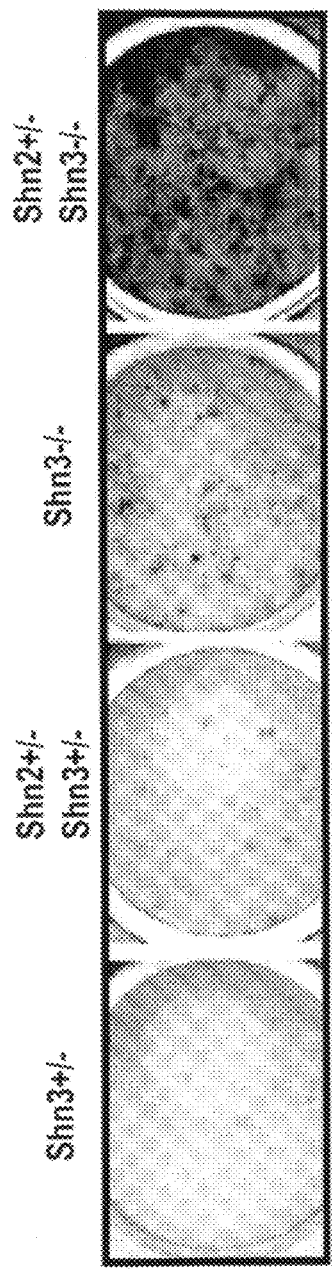

To determine if differences in Schnurri gene dosage could also alter osteoblast function in vitro, we generated bone marrow stromal cultures from 5-week old Shn3+/−, Shn2+/−Shn3+/−, Shn3−/− and Shn2+/−Shn3−/− mice. Kinetic analysis of matrix production by von Kossa staining over a 14-day period revealed that stromal cultures generated from Shn2+/−Shn3−/− mice produced the highest levels of mineralized matrix (FIG. 4D). Further reflecting the in vivo findings, we also observed that Shn2+/−Shn3+/− stromal cultures produced elevated levels of mineralized matrix when compared to the Shn3+/− cultures. These data reveal gradients of skeletal remodeling that are exquisitely sensitive to Shn2 and Shn3 gene expression. A fifty percent reduction in expression of either gene can impact both osteoblast function in vitro and bone formation in vivo.

Example 5. Reduced Osteoclastic Activity in Shn3-Deficient Mice In Vivo

Figure 5A:
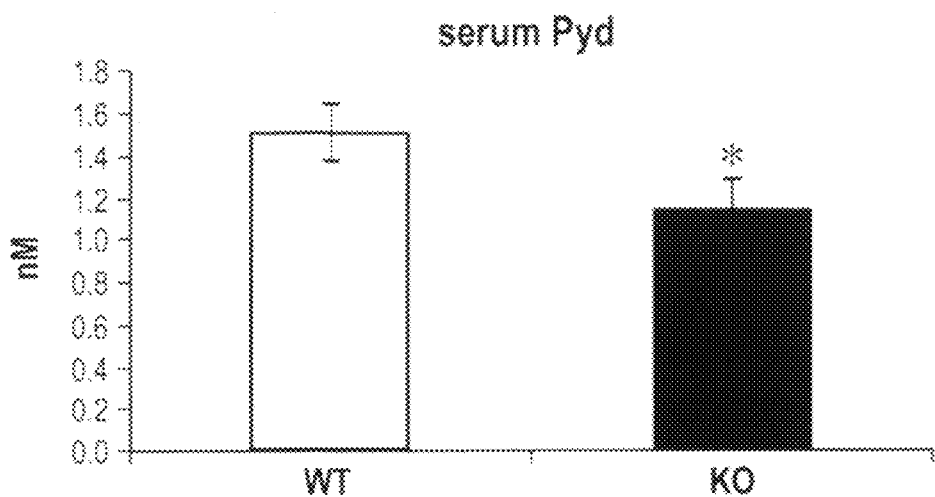
FIG. 5. Decreased bone resorption in Shn3-deficient mice. (A) Serum Pyd levels in 6 week old WT and Shn3-/- (KO) animals, n=6/group, * denotes p<0.05 comparing WT to KO. (B). Serum CTX levels in 6 week old WT and KO animals, n=10/group. (C) Representative photograph of whole mount TRAP stain (arrowheads highlight prominent staining near sutures) of WT (top row) and KO 8 week old skull preps. (D) Representative photomicrograph of 8 week old Shn3-/- femur section stained for TRAP at growth plate (GP, top), distal metaphyseal (Met, middle), and diaphyseal (Dia, bottom) section levels FIG. 6. Shn3-deficient osteoblasts are defective in driving osteoclastogenesis. (A) WT or Shn3-/- osteoblasts were cocultured with WT BM osteoclast precursors in the presence of the indicated calcitropic agents (final concentrations: vitamin D 10 nM, PGE2 10 μM, PTH 10 nM, isoproterenol 10 p.M). After 5 days, tissue culture supernatants were assayed for TRAP activity via colorimetric readout (A405). Error bars represent s.d. of absorbances from 3 independent wells. * denotes p<0.05. This experiment was repeated 4 independent times with similar results. (B) Representative photomicrographs of cocultures. (C) RNA was harvested from cocultures and expression of calcitonin receptor and cathepsin K was determined by quantitative real time PCR. Levels of the indicated genes were normalized to actin and expressed as relative to levels obtained with WT osteoblasts. Error bars represent s.d. of values obtained from PCR triplicates. * denotes p<0.05. This experiment was repeated 3 independent times with similar results.
Figure 5B:
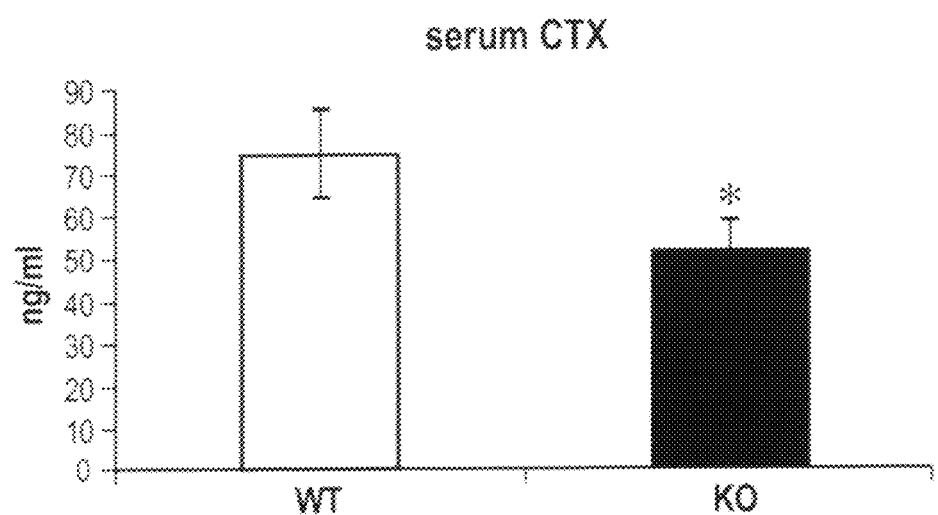

The osteoclastic activity in Shn3−/− mice was characterized in vivo. Since these animals show dramatic elevations in osteoblast behavior as assayed by dynamic histomorphometry (Jones, Wein et al. 2006) it was predicted that these mice should show a compensatory increase in serum markers of bone turnover. Surprisingly, this was not the case. As shown in FIG. 5A and FIG. 5B, serum markers of CTX and Pyd were significantly reduced in young (6 week old) Shn3−/− animals compared to WT littermates.

Figure 5C:
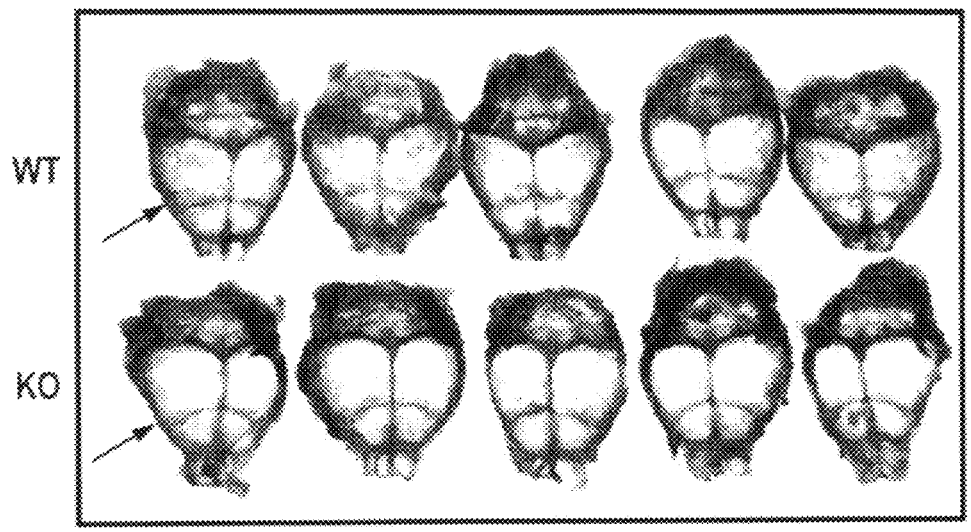
Figure 5D:
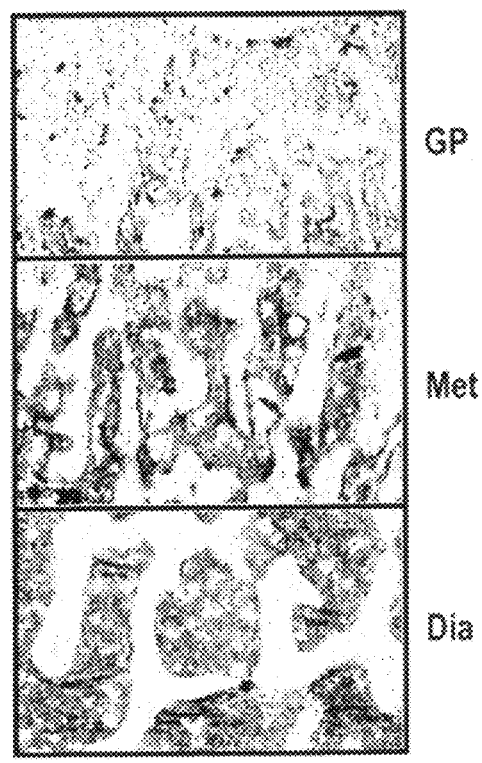

Previously reports have indicated comparable numbers of osteoclasts in WT and Shn3−/− skeletal tissue as assessed by static histomorphometric analysis just below the growth plate in the proximal tibia (Jones, Wein et al. 2006). Given the unexpected decrease in markers of bone resorption, a more extensive histochemical investigation of osteoclasts was performed and qualitative reductions in osteoclast numbers in whole mount skull preps (FIG. 5C) and along the surfaces of ectopic diaphyseal bone (FIG. 5D) in Shn3−/− animals were observed. Interestingly, this analysis again confirmed normal numbers of osteoclasts just below the growth plate in the tibiae and femurs of Shn3−/− animals, suggesting that Shn3 may control osteoclast numbers and/or activity in a skeletal region-selective manner.

Taken together, these data suggest the hypothesis that Shn3 expression in non-osteoclastic cells may regulate osteoclast development and/or activity. Radio-resistant cells of the osteoblastic lineage are known to support osteoclast development in vitro in response to calcitropic stimuli (Takahashi, Akatsu et al. 1988). Since then, a plethora of additional stimuli have been shown to drive osteoblast-mediated osteoclastogenesis including prostaglandins, inflammatory mediators, sympathomimetics, and tumor cells (O'Brien 2009).

Figure 6A:
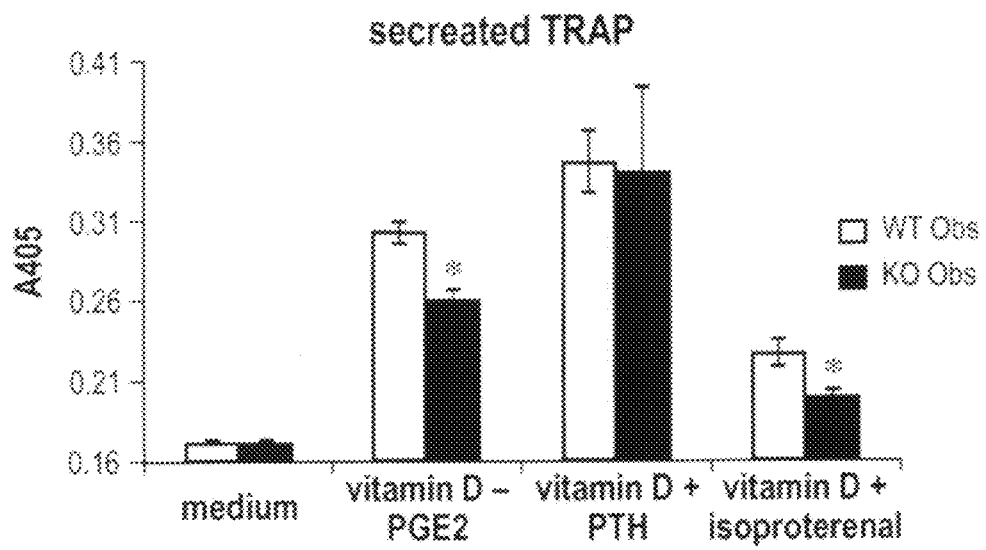
Figure 6B:
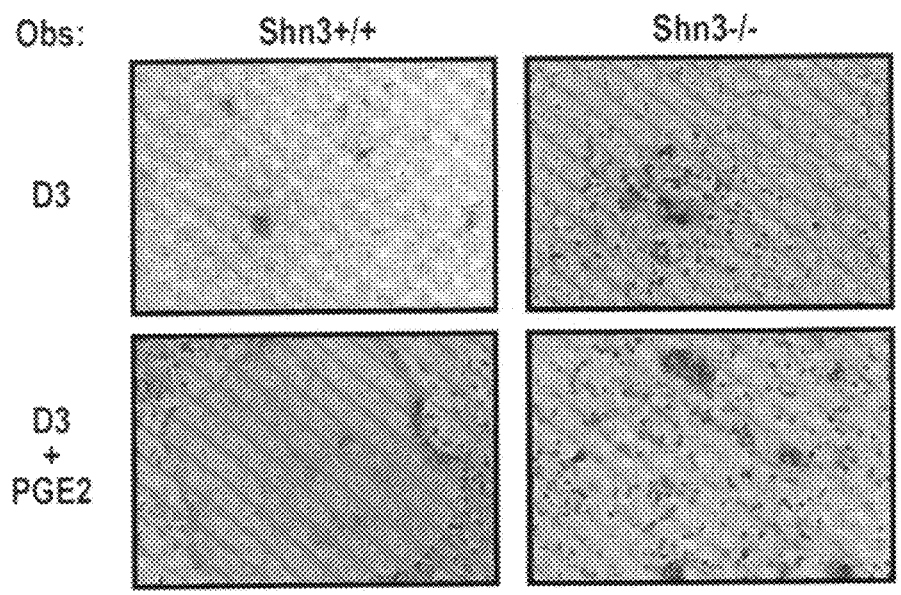
Figure 6C:
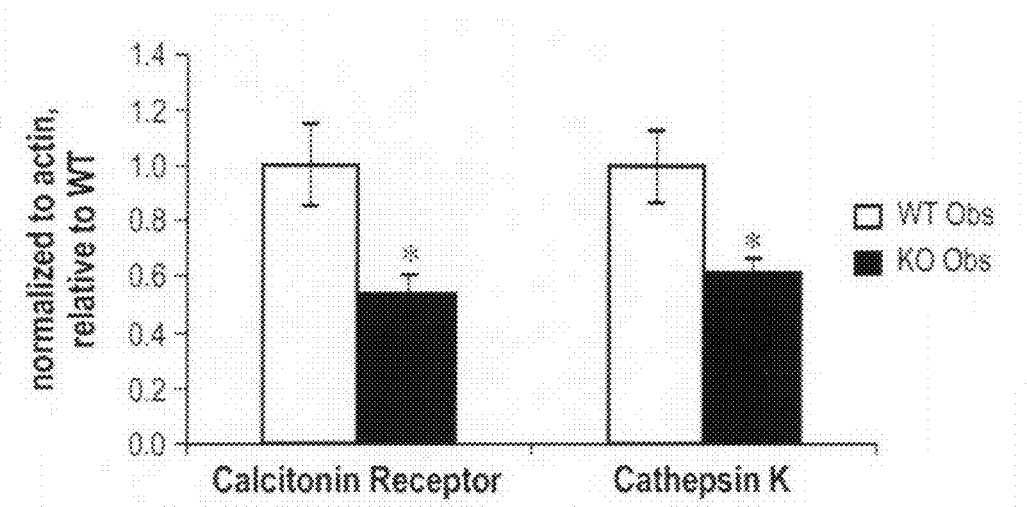

Example 6. Osteoblasts Lacking Shn3 are Defective in Driving Osteoclastogenesis To interrogate the ability of Shn3-deficient osteoblasts to support osteoclastogenesis, co-culture experiments were performed. In these assays, it was observed that osteoblastic/stromal cells lacking Shn3 were defective in driving osteoclastogenesis in response to prostaglandin PGE2 and the beta2-adrenergic receptor agonist isoproterenol, but not in response to parathyroid hormone (FIG. 6A). Morphologic analysis of osteoclasts from these co-culture assays revealed a consistent lack of giant multinucleated cells in the presence of Shn3−/− stromal cells (a representative photomicrograph is shown in FIG. 6B). Consistent with this, RNA obtained from these co-cultures showed reduced expression of terminal markers of osteoclast differentiation (Cathepsin K, Calcitonin Receptor) comparing WT to Shn3−/− osteoblasts (FIG. 6C).

Example 7. Reduced Levels of RANKL in the Absence of Shn3 In Vivo

Figure 7A:
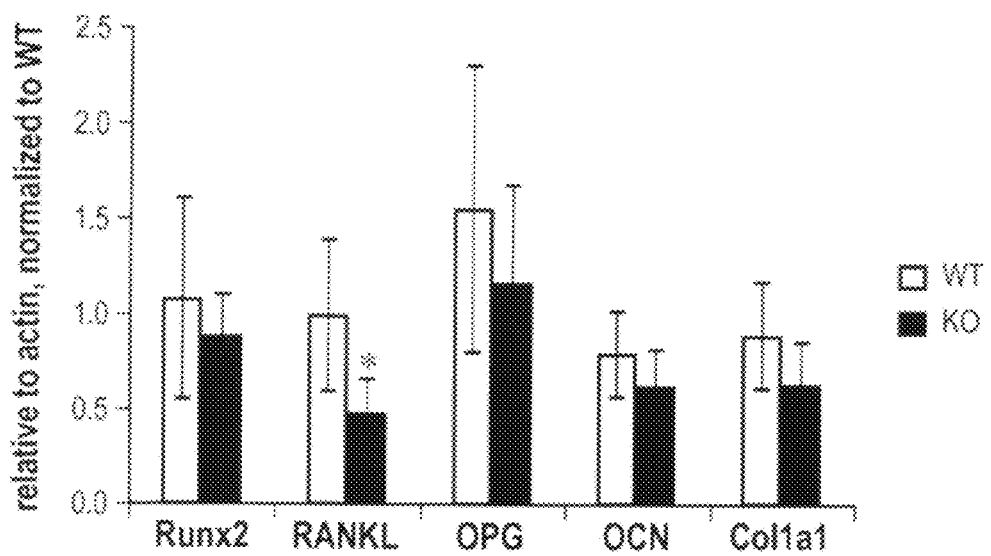
FIG. 7. Decreased RANKL in Shn3-deficient mice. (A) RNA was isolated from calvariae of WT and Shn3-/- (KO) 8 week old mice, n=5 mice per genotype. Transcript levels of the indicated genes were determined relative to actin by quantitative real time PCR and expressed as normalized to WT. Error bars represent s.d. values, * denotes p<0.05. The only gene showing significant change between WT and KO was RANKL. (B) Serum RANKL was determined from 8 week old WT and Shn3-/- (KO) mice, n=10 mice per genotype. * denotes p<0.01. (C) Representative photomicrograph from femurs from 8 week old WT and Shn3-/- which were co-stained for RANKL immunohistochemistry and TRAP at the level of the distal metaphysis. (D) Representative photomicrograph processed as in (C) at the level of the diaphysis. Note the paucity of TRAP-reactivity and RANKL immunoreactive cells at this level.
Figure 7B:
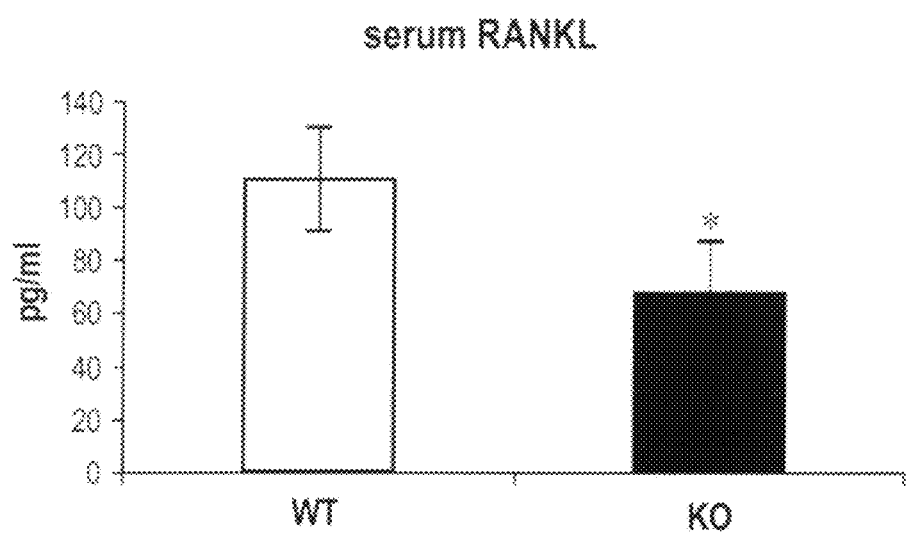

The mechanism(s) whereby Shn3 expression in osteoblastic stromal cells might control osteoclast differentiation was investigated. To this end, extensive RNA profiling was performed to determine, in an unbiased manner, genes controlled by Shn3. In doing so, we found that the critical osteoclastogenic cytokine TNFSF11 (RANKL) is one such gene whose levels are decreased in Shn3−/− bone tissue (FIG. 7A and data not shown). Consistent with this, serum analysis showed reductions in circulating levels of RANKL in Shn3– deficient animals (FIG. 7B).

Figure 7C:
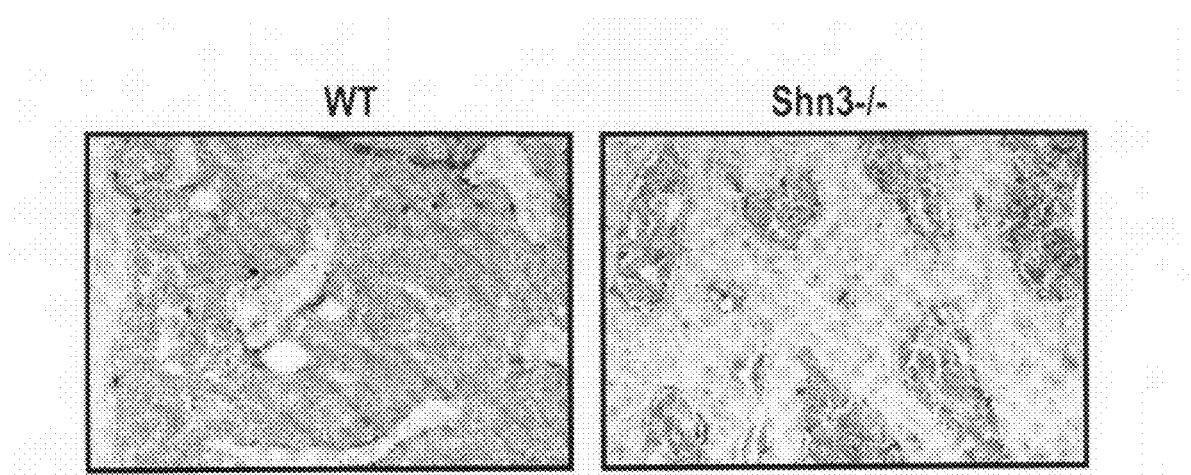
Figure 7D:
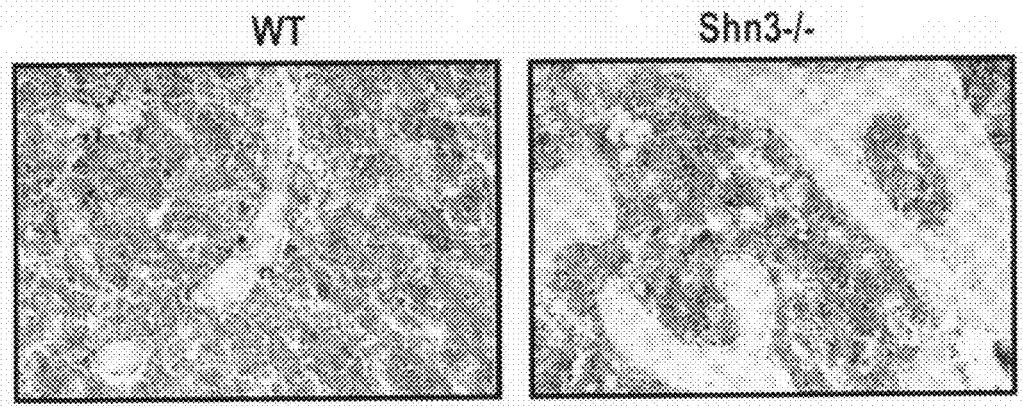

To further explore the expression pattern of RANKL in bone tissue lacking Shn3, immunohistochemistry for RANKL and histochemical labeling for the osteoclast marker TRAP were performed. Interestingly, these studies demonstrated comparable levels of RANKL in growth plate hypertrophic chondrocytes and p10 proximal metaphyseal bone lining cells, but qualitatively reduced levels of RANKL and TRAP in bone lining cells more distant from the growth plate (FIG. 7C metaphyseal region, FIG. 7D diaphyseal region). Of note, quantitative comparison of TRAP-positive cells along diaphyseal trabecular bone between WT and Shn3–/– animals is difficult due to dramatic qualitative differences in bone architecture at this site. Another cell type known to express RANKL is the Th17 cell (Sato, Suematsu et al. 2006). Shn3 is dispensible for both Th17 cell generation and Th17 cell RANKL expression. Taken together, these data indicate that Shn3 controls RANKL expression by osteoblastic stromal cells in vivo, but not in hypertrophic chondrocytes and Th17 cells.

Example 8. Reduced Expression of RANKL by Osteoblastic/Stromal Cells Lacking Shn3

Figure 8A:
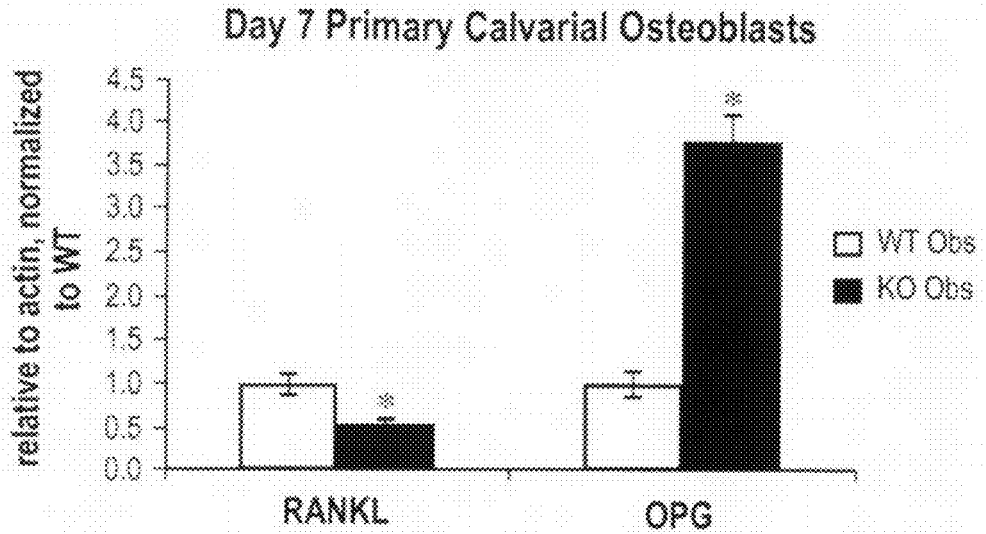
FIG. 8. Decreased RANKL in Shn3-deficient cells. (A) Primary calvarial-derived osteoblasts from WT and Shn3-/- (KO) mice were grown in culture for 7 days. RNA was isolated and transcript levels of RANKL and OPG were determined relative to actin. Error bars represent s.d. of values obtained from PCR triplicates. * denotes p<0.05. All experiments in this figure were repeated at least 3 independent times with similar results. (B) An SV40-transformed WT calvarial osteoblast cell line was infected with either control lentivirus, Shn3 shRNA lentivirus, or Shn3 overexpression (N3557) lentivirus. Infected cells were selected with puromycin. 4 days later, RNA was isolated and RANKL and OPG levels were determined relative to actin. (C) SV40-transformed WT (clone 20) and Shn3-/- (clone 13) cells were treated with the indicated calcitropic agents for 90 minutes and RANKL RNA levels were determined. (D) Day 0 primary calvarial osteoblasts were treated with the indicated agents for 3 hours and RANKL levels were determined.
Figure 8B:
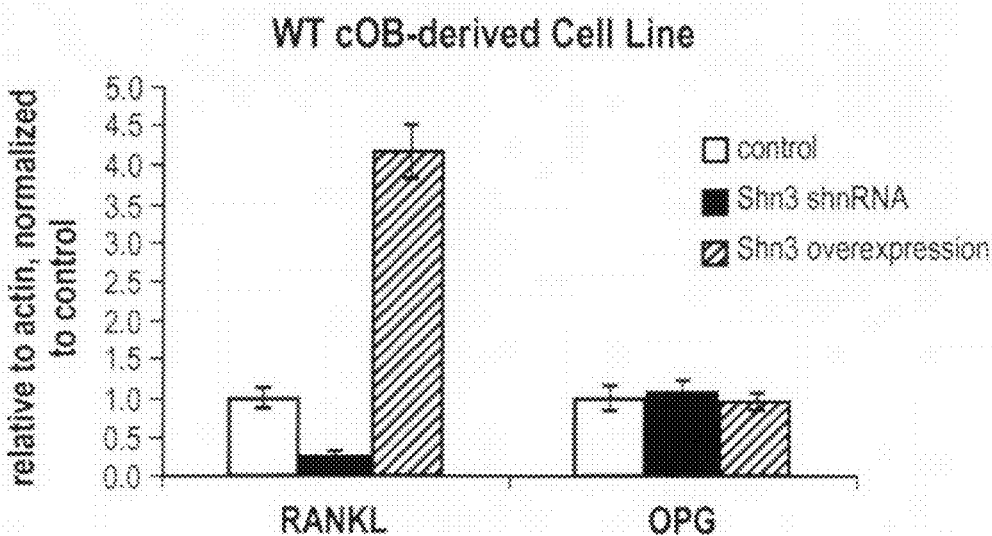

As expected, primary calvarial osteoblasts lacking Shn3 show reduced levels of RANKL mRNA after a 7 day in vitro culture period. Unexpectedly, these cells also display increased levels of the anti-osteoclastogenic factor OPG compared to WT cells (FIG. 8A). However, RANKL levels are known to decrease, and OPG levels to increase, during the course of osteoblast differentiation using this in vitro system (Thomas, Baker et al. 2001). To circumvent the possibility that the differences observed reflect disparate differentiation states, we acutely altered Shn3 levels in transformed osteoblast cell lines using lentivirus-based shRNA-mediated gene silencing and overexpression. As shown in FIG. 8B, these manipulations led to the previously observed alterations in RANKL, but not OPG, levels.

Figure 8C:
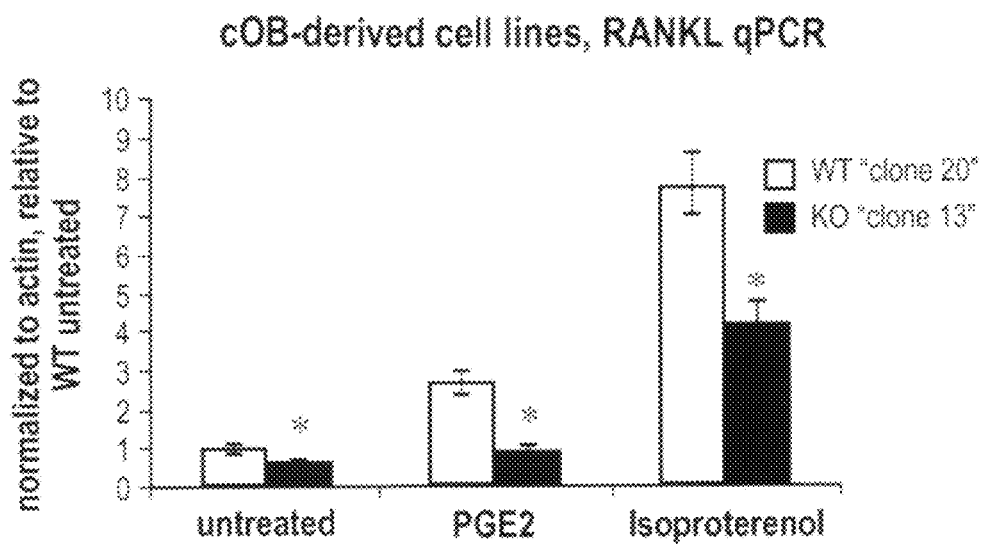
Figure 8D:
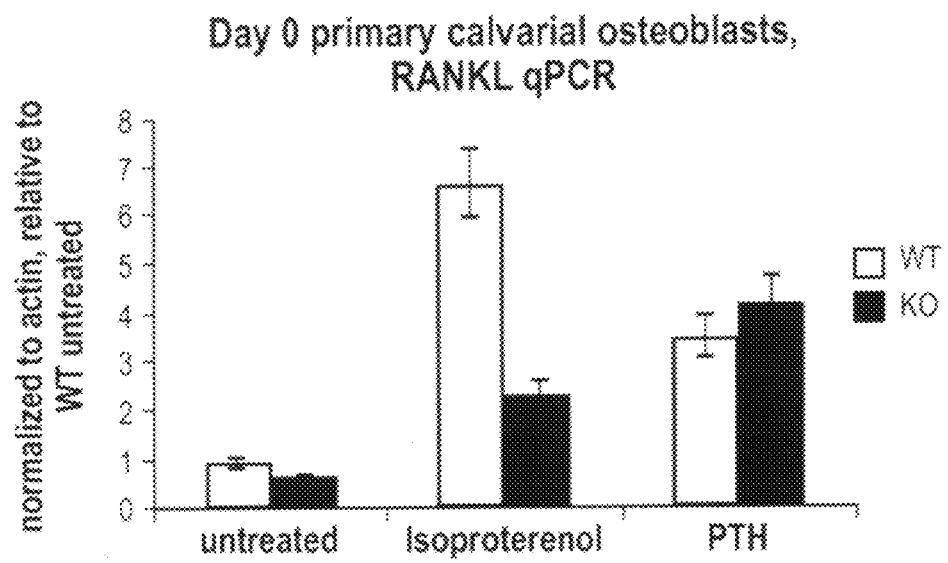

As shown in FIG. 6A, Shn3-deficient osteoblastic cells fully support osteoclastogenesis in response to PTH, but not in response to isoproterenol and PGE2. Accordingly, Shn3–/– osteoblastic cells are defective in upregulating RANKL in response to isoproterenol and PGE2, but not to PTH (FIG. 8C and FIG. 8D). Additionally, acute reductions in Shn3 levels by shRNA-mediated gene silencing reduced responsiveness to PGE2 as expected (Not shown). A combination of primary calvarial osteoblasts and SV40-transformed osteoblastic cells were used in these experiments due to different expression levels of receptors for these calcitropic agents in various cell types. Finally, when coculture experiments were performed in the presence of a neutralizing anti-OPG antibody, the defect in the ability of Shn3–/– osteoblasts to drive osteoclastogenesis was reversed (not shown), suggesting that reduced RANKL expression by these cells contributes in part to their inability to support osteoclast differentiation.

Figure 9A:
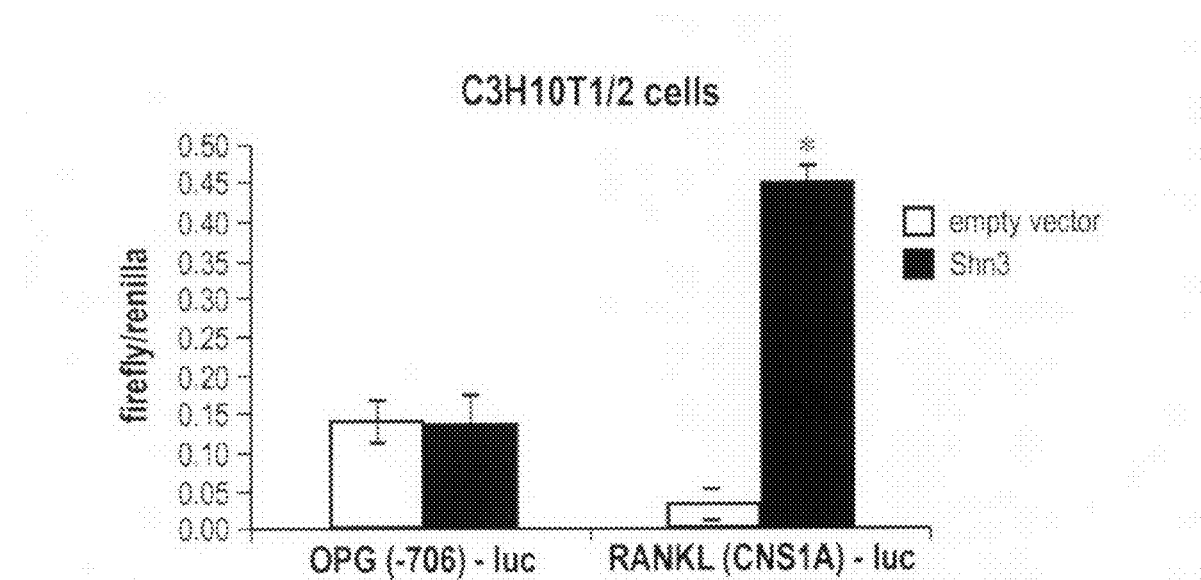
FIG. 9. Shn3 can regulate RANKL gene expression through upstream regulatory region and CREB. (A) C3H10T1/2 cells were transiently transfected with a luciferase reporter element containing either the proximal OPG promoter or the RANKL upstream regulatory element CNS 1A with either empty vector or Shn3. Firefly and renilla luciferase activities were determined after 48 hours. Error bars represent firefly/renilla ratio from triplicate experimental wells, * denotes p<0.05. This experiment was performed 3 independent times with similar results. (B) C3H10T1/2 cells were transfected as in (A) with the indicated CNS1A- luciferase reporter constructs. (C) 293T cells were transfected with the indicated combinations of Shn3 and HA-tagged versions of either CREB or Runx2. Shn3 precipitates with CREB with or without forskolin treatment.

Example 8. Shn3 Controls Expression of RANKL Through CREB and an Upstream Regulatory Element We next sought to determine the mechanism whereby Shn3 controls RANKL expression. TNFSF11 gene expression is controlled by a variety of distal and proximal regulatory regions (Fu, Manolagas et al. 2006; Kim, Yamazaki et al. 2006; O'Brien 2009). These experiments focused on a conserved regulatory region located 76 kB upstream of the transcriptional start site that had been described by two independent groups as important for calcitropic agent responsiveness. Moreover, when this non-coding sequence is deleted, mice show a mild high bone mass phenotype associated with decreased serum markers of bone turnover (Galli, Zella et al. 2008). Shn3 overexpression can enhance activity of this upstream promoter element, but not that of the proximal RANKL and OPG gene regulatory regions (FIG. 9A and data not shown).

Figure 9B:
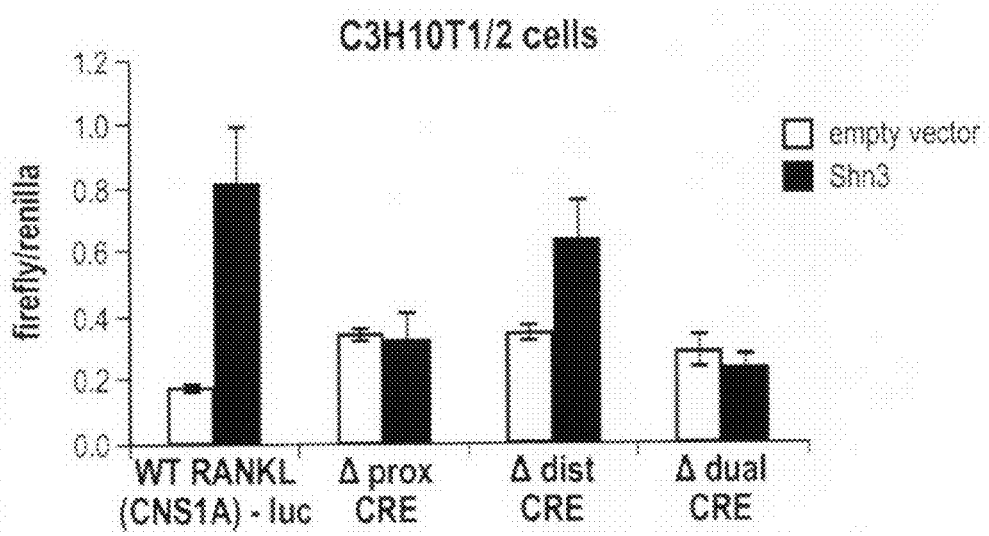
Figure 9C:
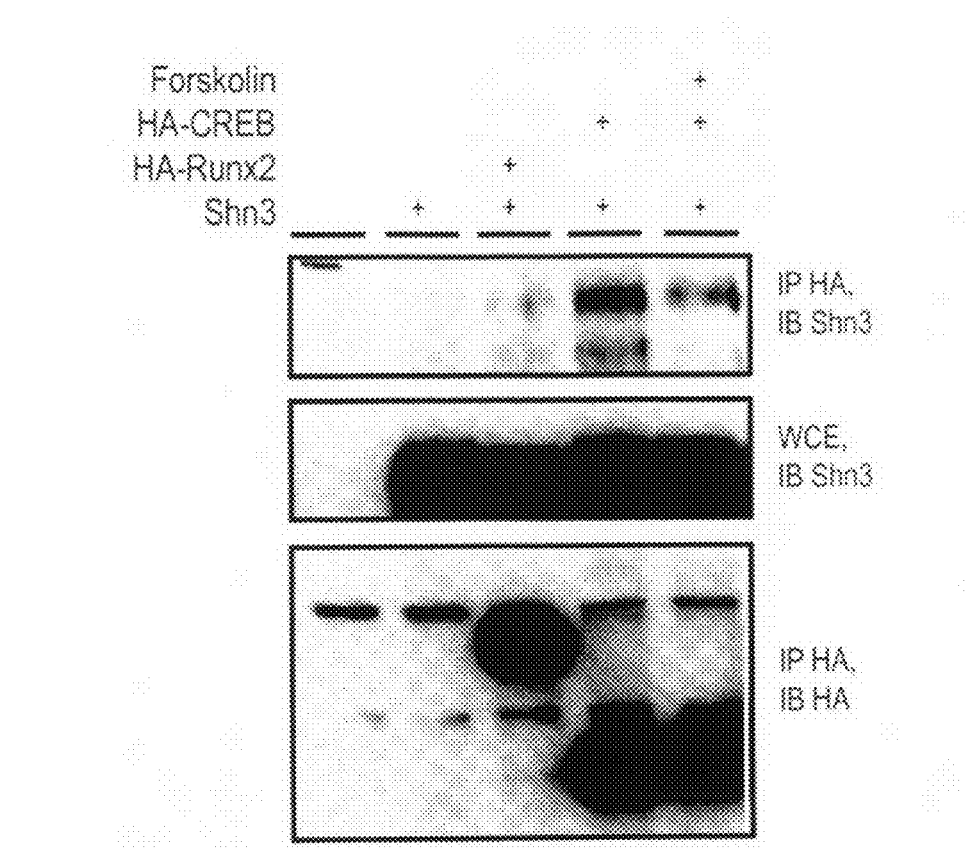

Transcription factors such as VDR, Runx2, CREB, and STAT3 are known to associate with this RANKL gene regulatory region (Kim, Yamazaki et al. 2006; Kim, Yamazaki et al. 2007). We found that Shn3 does not activate transcription from this reporter when the CREB binding sites are deleted (FIG. 9B). It had been previously demonstrated that Shn3 physically associates with Runx2 and regulates its activity (Jones, Wein et al. 2006). In overexpression studies, Shn3 can also bind CREB (FIG. 10C) and directly regulate its transcriptional activity (FIG. 10D). Finally, we performed chromatin immunoprecipitation experiments to determine whether Shn3 can associate with the RANKL gene regulatory elements. In these studies, Shn3 selectively associates with the previously described regulatory region (FIG. 10E). Taken together, these data suggest that Shn3 controls RANKL expression in osteoblastic cells in vivo and in vitro at least in part through a mechanism that involves binding to CREB in the context of a conserved upstream regulatory region.

Example 9. Shn3-Deficient Animals are Protected from Bone Loss Due to Aging and Disuse The physiological significance of these findings was explored in three models of stimulated bone resorption: aging, dietary-induced hypocalcemia, and disuse osteopenia. Young (8 week old) Shn3–/– mice show high bone mass associated with an increased rate of bone formation and decreased resorptive markers (Jones et al and FIGS. 5B and 5C). Aged (>3 months old) Shn3–/– animals display an enhanced osteosclerotic phenotype associated with extramedullary hematopoiesis (not shown), decreased histomorphometric indices of bone formation (FIG. 10A), and reduced serum levels of the resorptive markers Pyd and CTX (data not shown) and RANKL (Not shown). All told, these parameters are most consistent with an osteopetrotic phenotype due to an osteoclast-extrinsic defect.

One possibility to explain the age-dependent severe osteosclerosis observed in these animals is that their bone matrix becomes 'unresorbable' over time. To test this notion, aged (11 week old) WT and Shn3–/– animals were placed on a control or a low calcium diet for 2 weeks. In a well-described pathway involving release of PTH, animals are known to liberate skeletal calcium stores to maintain normocalcemia in this model (Aoki, Saito et al. 2006). Shn3–/– mice showed reductions in trabecular BV/TV (FIG. 10B), increases in serum markers of bone resorption (not shown), and were able to maintain normocalcemia (not shown) in this model. These data are not particularly surprising in light of our observations that Shn3 is dispensable for PTH-mediated induction of osteoclastogenesis in co-culture models (FIG. 6A) and RANKL upregulation in osteoblastic cells (FIG. 8D). Moreover, these data demonstrate that the Shn3–/– bone matrix is not unresorbable, thereby discounting the idea that biomechanical properties alone cause the high bone mass phenotype observed in these mice.

Figure 10C:
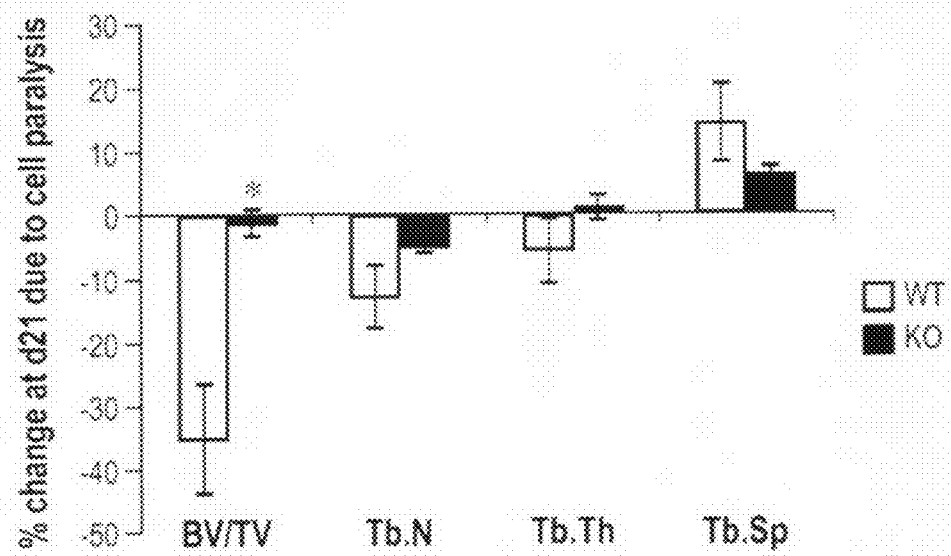

An osteoclast-driven model of disuse osteopenia was also employed (Warner, Sanford et al. 2006) to further test the physiologic relevance of our findings. In this model, botulinum toxin is injected into the calf muscle, which leads to muscle denervation and subsequent disuse osteopenia of the ipsilateral, but not contralateral, tibia. We subjected aged (6 month old) WT and Shn3−/− animals to this protocol. Both genotypes showed similar muscle atrophy and lack of changes of the contralateral limb (not shown) during the 21-day study period. While WT animals showed expected ipsilateral bone loss following this manipulation, Shn3−/− animals were protected at multiple time points (FIGS. 10C and 10D). This observation further solidifies a model in which Shn3 expression in osteoblastic/stromal cells plays an important role in regulating RANKL expression and thus, osteoclastic bone resorption in response to a variety of physiological stimuli.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for increasing trabecular bone formation and mineralization in the diaphysis of a bone, comprising contacting an osteoblast with a first agent that decreases expression of Schnurri-2 (Shn2) in the osteoblast wherein the first agent is selected from the group consisting of: a nucleic acid molecule that is antisense to a Shn2 molecule, a Shn2 small interfering RNA (siRNA) molecule, a dominant negative Shn2 molecule, or combinations thereof, and contacting the osteoblast with a second agent that decreases expression of Schnurri-3 (Shn3) in the osteoblast, wherein the second agent is selected from the group consisting of: a nucleic acid molecule that is antisense to a Shn3 molecule, a Shn3 siRNA molecule, a dominant negative Shn3 molecule, or combinations thereof, wherein decreased expression of both Shn2 and Shn3 increases trabecular bone formation and mineralization in the diaphysis of the bone relative to decreased expression of Shn3 alone.

2. A method for treating a disease, disorder, condition, or injury that would benefit from increased trabecular bone formation and mineralization in the diaphysis of a bone in a subject in need thereof, comprising contacting an osteoblast from the subject with a first agent that decreases the expression of Schnurri-2 (Shn2) in the osteoblast wherein the first agent is selected from the group consisting of: a nucleic acid molecule that is antisense to a Shn2 molecule, a Shn2 small interfering RNA (siRNA) molecule, a dominant negative Shn2 molecule, or combinations thereof, and contacting the osteoblast with a second agent that decreases expression of Schnurri-3 (Shn3) in the osteoblast, wherein the second agent is selected from the group consisting of: a nucleic acid molecule that is antisense to a Shn3 molecule, a Shn3 siRNA molecule, a dominant negative Shn3 molecule, or combinations thereof, wherein decreased expression of both Shn2 and Shn3 increases trabecular bone formation and mineralization in the diaphysis of the bone in the subject relative to decreased expression of Shn3 alone.

3. The method of claim 2, wherein the step of contacting the osteoblast with an agent that decreases the expression of Shn3 in the osteoblast occurs in vitro.

4. The method of claim 2, wherein the step of contacting the osteoblast with an agent that decreases the expression of Shn3 in the osteoblast occurs in vivo.

5. The method of claim 3 or 4, wherein the agent is present on a surface.

6. The method of claim 2, wherein the disease, disorder, condition, or injury is selected from the group consisting of: osteoporosis, osteopenia, osteomalacia, and osteitis deformans (Paget's disease of bone), osteoarthritis and inflammatory arthritides characterized by bone loss or excess bone formation including for example rheumatoid arthritis, ankylosing spondylitis, psoriatic arthritis.

7. The method of claim 2, wherein the step of contacting the osteoblast with an agent that decreases the expression of Shn2 in the osteoblast occurs in vitro.

8. The method of claim 2, wherein the step of contacting the osteoblast with an agent that decreases the expression of Shn2 in the osteoblast occurs in vivo.

* * * * *

UNITED STATES PATENT AND TRADEMARK OFFICE
CERTIFICATE OF CORRECTION

PATENT NO. : 9,745,589 B2
APPLICATION NO. : 13/521709
DATED : August 29, 2017
INVENTOR(S) : Glimcher et al.

Page 1 of 2

It is certified that error appears in the above-identified patent and that said Letters Patent is hereby corrected as shown below:

On the Title Page
In Column 2, item (56), under "Foreign Patent Documents", Line 9, delete "20051042726" and insert --2005/042726-- therefor In Column 2, item (56), under "Foreign Patent Documents", Line 10, delete "20051113588" and insert --2005/113588-- therefor In Column 2, item (56), under "Foreign Patent Documents", Line 11, delete "20051124343" and insert --2005/124343-- therefor In Column 2, item (56), under "Foreign Patent Documents", Line 13, delete "20061132248" and insert --2006/132248-- therefor In Column 2, item (56), under "Foreign Patent Documents", Line 14, delete "20081103314" and insert --2008/103314-- therefor In Column 2, item (56), under "Foreign Patent Documents", Line 15, delete "20081133936" and insert --2008/1133936-- therefor In Column 2, item (56), under "Foreign Patent Documents", Line 16, delete "20081153814" and insert --2008/153814-- therefor In Column 2, item (56), under "Foreign Patent Documents", Line 18, delete "20131119893" and insert --2013/119893-- therefor In Column 2, item (56), under "Other Publications", Line 5, delete "C2H2" and insert --$C_2H_2$-- therefor On page 2, in Column 1, item (56), under "Other Publications", Line 1, delete "JOnes" and insert --Jones-- therefor Signed and Sealed this
Sixteenth Day of October, 2018

Andrei Iancu
*Director of the United States Patent and Trademark Office*

CERTIFICATE OF CORRECTION (continued)
U.S. Pat. No. 9,745,589 B2

On page 2, in Column 1, item (56), under "Other Publications", Line 1, delete "theZinc" and insert --the Zinc-- therefor On page 2, in Column 2, item (56), under "Other Publications", Line 31, delete "V (D)J" and insert --V(D)J-- therefor On page 3, in Column 1, item (56), under "Other Publications", Line 46-47, delete "is is" and insert --is-- therefor On page 3, in Column 2, item (56), under "Other Publications", Line 7, delete "Rimes," and insert --Himes,-- therefor On page 3, in Column 2, item (56), under "Other Publications", Line 13, delete "S100A41mts1,"" and insert --S100A4/mts1,"-- therefor On page 4, in Column 2, item (56), under "Other Publications", Line 20, delete "at.," and insert --al.,-- therefor On page 4, in Column 2, item (56), under "Other Publications", Line 23, delete "at.," and insert --al.,-- therefor On page 4, in Column 2, item (56), under "Other Publications", Line 43, delete "at.," and insert --al.,-- therefor On page 4, in Column 2, item (56), under "Other Publications", Line 46, delete "at.," and insert --al.,-- therefor On page 4, in Column 2, item (56), under "Other Publications", Line 51, delete "at.," and insert --al.,-- therefor On page 4, in Column 2, item (56), under "Other Publications", Line 52, delete "lifferentiation" and insert --differentiation-- therefor On page 5, in Column 1, item (56), under "Other Publications", Line 9, delete "C 2 H 2" and insert --$C_2H_2$-- therefor On page 5, in Column 2, item (56), under "Other Publications", Line 45, delete "V (D)J" and insert --V(D)J-- therefor In the Claims
In Column 71, Line 2, in Claim 1, after "comprising", insert --:--

In Column 71, Line 26, in Claim 2, after "comprising", insert --:--